(12) United States Patent
Bond et al.

(10) Patent No.: US 7,785,903 B2
(45) Date of Patent: Aug. 31, 2010

(54) VARIABLE DOMAIN LIBRARY AND USES

(75) Inventors: Christopher J. Bond, San Francisco, CA (US); Sachdev Sidhu, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 524 days.

(21) Appl. No.: 11/102,502

(22) Filed: Apr. 8, 2005

(65) Prior Publication Data

US 2005/0266000 A1   Dec. 1, 2005

Related U.S. Application Data

(60) Provisional application No. 60/560,949, filed on Apr. 9, 2004.

(51) Int. Cl.
  G01N 33/536   (2006.01)
  G01N 33/543   (2006.01)
  C12P 21/08    (2006.01)
  C12P 21/04    (2006.01)

(52) U.S. Cl. .................... 436/536; 436/518; 530/387.3; 435/69.6

(58) Field of Classification Search ........................ None
  See application file for complete search history.

(56) References Cited

U.S. PATENT DOCUMENTS

| | | |
|---|---|---|
| 4,816,567 A | 3/1989 | Cabilly et al. |
| 5,223,409 A | 6/1993 | Ladner et al. |
| 5,403,484 A | 4/1995 | Ladner et al. |
| 5,427,908 A | 6/1995 | Dower et al. |
| 5,432,018 A | 7/1995 | Dower et al. |
| 5,498,530 A | 3/1996 | Schatz et al. |
| 5,534,615 A | 7/1996 | Baker et al. |
| 5,565,332 A | 10/1996 | Hoogenboom et al. |
| 5,580,717 A | 12/1996 | Dower et al. |
| 5,580,723 A | 12/1996 | Wells et al. |
| 5,591,828 A | 1/1997 | Bosslet et al. |
| 5,658,727 A | 8/1997 | Barbas et al. |
| 5,667,780 A | 9/1997 | Ho et al. |
| 5,667,988 A | 9/1997 | Barbas et al. |
| 5,702,892 A | 12/1997 | Mulligan-Kehoe |
| 5,723,286 A | 3/1998 | Dower et al. |
| 5,723,323 A | 3/1998 | Kauffman et al. |
| 5,733,743 A | 3/1998 | Johnson et al. |
| 5,750,373 A | 5/1998 | Garrard et al. |
| 5,759,817 A | 6/1998 | Barbas |
| 5,763,192 A | 6/1998 | Kauffman et al. |
| 5,770,434 A | 6/1998 | Huse |
| 5,780,279 A | 7/1998 | Matthews et al. |
| 5,821,337 A | 10/1998 | Carter et al. |
| 5,824,520 A | 10/1998 | Mulligan-Kehoe |
| 5,834,250 A | 11/1998 | Wells et al. |
| 5,837,242 A | 11/1998 | Holliger et al. |
| 5,962,255 A | 10/1999 | Griffiths et al. |
| 5,965,371 A | 10/1999 | Marasco et al. |
| 5,969,108 A | 10/1999 | McCafferty et al. |
| 6,037,454 A | 3/2000 | Jardieu et al. |
| 6,040,136 A | 3/2000 | Garrard et al. |
| 6,054,297 A | 4/2000 | Carter et al. |
| 6,057,098 A | 5/2000 | Buechler et al. |
| 6,096,551 A | 8/2000 | Barbas et al. |
| 6,140,471 A | 10/2000 | Johnson et al. |
| 6,172,197 B1 | 1/2001 | McCafferty et al. |
| 6,248,516 B1 | 6/2001 | Winter et al. |
| 6,399,763 B1 | 6/2002 | Frenken et al. |
| 6,627,196 B1 | 9/2003 | Baughman et al. |
| 6,696,245 B2 | 2/2004 | Winter et al. |
| 6,838,254 B1 | 1/2005 | Hamers et al. |
| 6,846,634 B1 | 1/2005 | Tomlinson et al. |
| 2004/0071696 A1 | 4/2004 | Adams et al. |

(Continued)

FOREIGN PATENT DOCUMENTS

EP     266032     4/1988

(Continued)

OTHER PUBLICATIONS

Paul, Fundamental Immunology, 3rd Edition, 1993, pp. 292-295.*

(Continued)

*Primary Examiner*—Larry R. Helms
*Assistant Examiner*—Anne M. Gussow
(74) *Attorney, Agent, or Firm*—Jones Day

(57) ABSTRACT

The invention provides polypeptides comprising a variant heavy chain variable framework domain (VFR). In some embodiments, the amino acids defining the VFR form a loop of an antigen binding pocket. In an embodiment, the polypeptide is a variable domain of a monobody and has a variant VFR. The polypeptide may optionally comprise one or more complementary determining regions (CDRs) of antibody variable domains. In an embodiment, the polypeptide is a variable domain of a monobody and has a variant VFR and one or more variant CDRs. Libraries of polypeptides that include a plurality of different antibody variable domains generated by creating diversity in a VFR, and optionally, one or more CDRs are provided and may be used as a source for identifying novel antigen binding polypeptides that can be used therapeutically or as reagents. The invention also provides fusion polypeptides, compositions, and methods for generating and using the polypeptides and libraries.

23 Claims, 4 Drawing Sheets

U.S. PATENT DOCUMENTS

| | | |
|---|---|---|
| 2004/0123343 A1 | 6/2004 | La Rosa et al. |
| 2004/0236078 A1 | 11/2004 | Carter et al. |
| 2005/0037420 A1 | 2/2005 | Zhang et al. |
| 2005/0069955 A1 | 3/2005 | Plaskin et al. |
| 2005/0119455 A1 | 6/2005 | Fuh et al. |
| 2005/0266000 A1 | 12/2005 | Bond et al. |

FOREIGN PATENT DOCUMENTS

| | | |
|---|---|---|
| EP | 368684 | 5/1990 |
| EP | 0584421 A1 | 3/1994 |
| EP | 0 628 639 | 12/1994 |
| EP | 1403367 A1 | 3/2004 |
| WO | WO 92/01047 | 1/1992 |
| WO | WO 92/03461 | 3/1992 |
| WO | WO 92/20791 | 11/1992 |
| WO | WO 93/06213 | 4/1993 |
| WO | WO 93/11161 | 6/1993 |
| WO | WO 93/11236 | 6/1993 |
| WO | WO 93/19172 | 9/1993 |
| WO | WO 94/04678 | 3/1994 |
| WO | WO 94/25591 | 11/1994 |
| WO | WO 97/35196 | 9/1997 |
| WO | WO 97/49805 | 12/1997 |
| WO | WO 98/15833 | 4/1998 |
| WO | WO 99/06587 | 2/1999 |
| WO | WO 99/46284 | 9/1999 |
| WO | WO 00/02909 | 1/2000 |
| WO | WO 00/24884 | 5/2000 |
| WO | WO 00/29004 | 5/2000 |
| WO | WO 00/43507 | 7/2000 |
| WO | WO 00/77194 A1 | 12/2000 |
| WO | WO 01/44463 | 6/2001 |
| WO | WO 01/90190 A2 | 11/2001 |
| WO | WO 02/061071 A2 | 8/2002 |
| WO | WO 03/102157 | 6/2003 |
| WO | WO 2004/058821 A2 | 7/2004 |
| WO | WO 2004/101790 | 11/2004 |
| WO | WO 2005/012531 A2 | 2/2005 |

OTHER PUBLICATIONS

Rudikoff et al Proc. Natl. Acad. Sci. USA, 79:1979-1983, Mar. 1982.*
Bendig M. M. Methods: A Companion to Methods in Enzymology, 1995; 8:83-93.*
Harmen et al. Molecular Immunology, 2000. 37:579-590).*
Bond et al. J. Molecular Biology, 2003. 332:643-655.*
Muyldermans. Review of Molecular Microbiology, 2001. 74:277-302.*
Saerens et al. J. Molecular Biology, 2005. 23:597-607.*
Rader, Cheresh, and Barbas III. A phage display approach for rapid antibody humanization: Designed combinatorial V gene libraries. Proceedings of the National Academy of Sciences, 1998. vol. 95, pp. 8910-8915.*
Barbas III et al., 1991, Proc. Natl. Acad. Sci. USA, 88:7978-7982 "Assembly of combinatorial antibody libraries on phage surfaces: The gene III site".
Barbas III et al., 1992, Proc. Natl. Acad. Sci. USA, 89:4457-4461 "Semisynthetic combinatoral antibody libraries: A chemical solution to the diversity problem".
Casset et al., 2003, Biochemical and Biophysical Research Communications, 307:198-205 "A peptide mimetic of an anti-CD4 monoclonal antibody by rational design".
De Pascalis et al., 2002, The Journal of Immunology, 169:3076-3084 "Grafting of "Abbreviated" Complementarity-Determining Regions Containing Specificity-Determining Residues Essential for Ligand Contact to Engineer a Less Immunogenic Humanized Monoclonal Antibody".
Fuh, G., 2007, Expert Opin. Boil. Ther., 7(1):73-87 "Synthetic antibodies as therapeutics".

Glockshuber et al., 1991, Biochemistry, 30(12):3049-3054 "Mapping and Modification of an Antibody Hapten Binding Site: A Site-Directed Mutagenesis Study of McPC603".
Holm et al., 2007, Molecular Immunology, 44:1075-1084 "Functional mapping and single chain construction of the anti-cytokeratin 8 monoclonal antibody TS1".
Kelley et al., 1992, Biochemistry, 31(24):5434-5441 "Antigen Binding Thermodynamics and Antiproliferative Effects of Chimeric and Humanized anti-p185HER2 Antibody Fab Fragments".
MacCallum et al., 1996, J. Mol. Biol., 262:732-745 "Antibody-antigen Interactions: Contact Analysis and Binding Site Topography".
Marks et al., 1991, J. Mol. Biol., 222:581-597 "By-passing Immunization—Human Antibodies from V-gene Libraries Displayed on Phage".
Morea et al., 1998, J. Mol. Biol., 275:269-294 "Conformations of the Third Hypervariable Region in the VH Domain of Immunoglobulins".
Muyldermans et al., TIBS, 26:230-235 (2001) "Recognition of antigens by single-domain antibody fragments: the superfluous luxury of paired domains".
Padlan et al., 1995, The FASEB Journal, 9:133-139 "Identification of specificity-determining residues in antibodies".
Pini et al., 1998, J. Biol. Chem., 273(34):21769-21776 "Design and Use of a Phage Display Library".
Radley et al., 2003, J. Mol. Biol., 332(3)529-758 "Allosteric Switching by Mutually Exclusive Folding of Protein Domains".
Randen et al., 1993, Eur. J. Immunol., 23:2692-2686 "Complementarity-determining region 2 is implicated in the binding of staphylococcal protein A to human immunoglobulin VHIII variable regions".
Spinelli et al., Biochemistry, 39:1217-1222 (2000) "Camelid heavy-chain variable domains provide efficient combining sites to haptens".
Verhoeyen et al., 1988, Science, 239:1534-1536 "Reshaping Human Antibodies: Grafting an Antilysozyme Activity".
Wu et al., 1998, Proc. Natl. Acad. Sci. USA, 95:6037-6042 "Stepwise in vitro affinity maturation of Vitaxin, an αv β3-specific humanized mAB".
Wu et al., 1999, J. Mol. Biol., 294:151-162 "Humanization of a Murine Monoclonal Antibody by Simultaneous Optimization of Framework and CDR Residues".
Supplementary European Search Report dated May 13, 2008.
Supplementary Partial European Search Report dated Jul. 4, 2005.
Aujame et al., 1997, "High Affinity Human Antibodies By Phage Display," Human Antibodies, 8(4):155-168.
Chan, 1999, "Folding Alphabets," Nat. Struct. Biol., 6(11):994-996.
Cho et al., 2003, "Structure Of The Extracellular Region Of HER2 Alone And In Complex With The Herceptin Fab," Nature, 421:756-760.
Conrath et al., 2001, "Camel Single-Domain Antibodies As Modular Building Units In Bispecific And Bivalent Antibody Constructs," J. Biol. Chem., 276(10):7346-7350.
Davies et al., 1995, "Antibody VH Domains As Small Recognition Units," Biotechnology 13:475-479.
Davies et al., 1995, "An Antibody VH Domain With A Lox-Cre Site Integrated Into Its Coding Region: Bacterial Recombination Within A Single Polypeptide Chain," FEBS Letters, 377:92-96.
Davies et al., 1996, "Affinity Improvement Of Single Antibody VH Domains: Residues In All Three Hypervariable Regions Affect Antigen Binding," Immunotechnology, 2(3):169-179.
Davies et al., 1996, "Single Antibody Domains As Small Recognition Units: Design And In Vitro Antigen Selection Of Camelized, Human VH Domains With Improved Protein Stability," Protein Engineering, 9(6):531-537.
Fellouse et al., 2004, "Synthetic Antibodies From Four-Amino-Acid Code: A Dominant Role For Tyrosine In Antigen Recognition," Proceedings of the National Academy of Sciences, 101(34):12467-12472.
Ghahroudi et, al., 1997, "Selection And Identification Of Single Domain Antibody Fragments From Camel Heavy-Chain Antibodies," FEBS Letters, 414:521-526.
Hendershot et al., 1987, "Assembly And Secretion Of Heavy Chains That Do Not Associate Posttranslationally With Immunoglobulin Heavy Chain-Binding Protein," Journey of Cell Biol., 104:761-767.

Jespers et al., 2004, "Crystal Structure Of HEL4, A Soluble, Refoldable Human $V_H$ Single Domain With A Germ-Line Scaffold," J. Mol. Biol., 337:893-903.

Lauwereys et al., 1998, "Potent Enzyme Inhibitors Derived From Dromedary Heavy-Chain Antibodies," EMBO Journal, 17(13):3512-3520.

Lee et al., 2004, "High-Affinity Human Antibodies From Phage-Displayed Synthetic Fab Libraries With A Single Framework Scaffold," J. Mol. Biol., 340(5):1073-1093.

Nguyen et al., 1998, "The Specific Variable Domain Of Camel Heavy-Chain Antibodies Is Encoded In The Germline," J. Mol. Biol., 275:413-418.

Nguyen et al., 2003, "Heavy-Chain Only Antibodies Derived From Dromedary Are Secreted And Displayed By Mouse B Cells," Immunol., 109:93-101.

Reiter et al., 1999, "An Antibody Single-Domain Phage Display Library Of A Native Heavy Chain Variable Region: Isolation Of Functional Single-Domain VH Molecules With A Unique Interface," J. Mol. Biol., 290:685-698.

Spinelli et al., 2004, "Domain Swapping Of A Llama VHH Domain Builds A Crystal-Wide β-Sheet Structure," FEBS Letters, 564:35-40.

Ueda et al., 2004, "Stabilization Of Antibody $V_H$-Domains By Proteolytic Selection," J. Mol. Catalysis B: Enzymatic, 28:173-179.

Vu et al., 1997, "Comparison Of Llama $V_H$ Sequences From Conventional And Heavy Chain Antibodies," Mol. Immunol., 34(16-17):1121-1131.

Ward et al., 1989, "Binding Activities Of A Repertoire Of Single Immunoglobulin Variable Domains Secreted From *Escherichia coli*," Nature, 341:544-546.

Willuda et al., 1999, "High Thermal Stability Is Essential For Tumor Targeting Of Antibody Fragments: Engineering Of A Humanized Anti-Epithelial Glycoprotein-2 (Epithelial Cell Adhesion Molecule) Single-Chain Fv Fragment," Cancer Research, 59:5758-5767.

Arbabi Ghahroudi, M. et al., "Selection and identification of single domain antibody fragments from camel heavy-chain antibodies", FEBS Letter, 414:521-526 (1997).

Arndt, K. et al., "Factors Influencing the Dimer to Monomer Transition of an Antibody Single-Chain Fv Fragment", Biochemistry, 37:12918-12926 (1998).

Barbas, C. et al., "In Vitro evolution of a neutralizing human antibody to human immunodeficiency virus type 1 to enhance affinity and broaden strain cross-reactivity", Proc. Natl. Acad. Sci. USA, 91:3809-3813 (1994).

Barbas, C. et al., "Selection and evolution of high-affinity human anti-viral antibodies", Trends Biotech, 14:230-234 (1996).

Bass, S. et al., "Hormone Phage: An Enrichment Method for Variant Proteins with Altered Binding Properties", Proteins, 8:309-314 (1990).

Bond, C. et al., "Contributions of CDR3 to $V_HH$ Domain Stability and the Design of Monobody Scaffolds for Naïve Antibody Libraries", J. Mol. Biol., 332:649-655 (2003).

Braunagel, M. et al., "Construction of a semisynthetic antibody library using trinucleotide oligos", Nucleic Acids Research, 25(22):4690-4691 (1997).

Carter et al., "Humanization of an anti-p185$^{HER2}$ antibody for human cancer therapy", Proc. Natl. Acad. Sci. USA, 89:4285-4289 (1992).

Chen, Y. et al., "Selection and Analysis of an Optimized Anti-VEGF Antibody: Crystal Structure of an Affinity-matured Fab in Complex with Antigen", J. Mol. Biol., 293:865-881 (1999).

Clackson, T. et al., "Making antibody fragments using phage display libraries", Nature, 352:624-628 (1991).

Connolly, J., "Analytical Molecular Surface Calculation", J. Appl. Cryst., 16:548-558 (1983).

Cunningham, B. et al., "High-Resolution Epitope Mapping of hGH-Receptor Interactions by Alanine-Scanning Mutagenesis", Science, 244(4908):1081-1085 (1989).

Dall'Acqua, W. et al., "Antibody Engineering", Current Opinion in Structural Biology, 8:443-450 (1998).

Davis, B. et al., Microbiology Including Immunology and Molecular Genetics, pp. 237, 245-247, 374 (1980).

de Kruif, J. et al., "Selection and application of human single chain Fv antibody fragments from a semi-synthetic phage antibody display library with designed CDR3 regions", J. Mol. Biol., 248:97-105 (1995).

de Kruif, J. et al., "Leucine Zipper Dimerized Bivalent and Bispecific scFv Antibodies from a Semi-synthetic Antibody Phage Display Library", The Journal of Biological Chemistry, 271(13):7630-7634 (1996).

de Wildt, R. et al., "Antibody arrays for high-throughput screening of antibody-antigen interactions", Nature Biotechnology, 18:989-994 (2000).

Decanniere, K. et al., "A single-domain antibody fragment in complex with RNase A: non-canonical loop structures and nanomolar affinity using two CDR loops", Structure, 7:361-370 (1999).

Decanniere, K. et al., "Canonical antigen-binding loop structures in immunoglobulins: More structures, more canonical classes?", J. Mol. Bio., 300:83-91 (2000).

Decanniere, K. et al., "Degenerate interfaces in antigen-antibody complexes", J. Mol. Bio., 313:473-478 (2001).

Deng, S. et al., "Selection of Antibody Single-chain Variable Fragments with Improved Carbohydrate Binding by Phage Display", J. Biol. Chem., 269:9533-9538 (1994).

Desmyter, A. et al., "Antigen specificity and high affinity binding provided by one single loop of a camel single-domain antibody", J. Biol. Chem., 276:26285-26290 (2001).

Desmyter, A. et al., "Crystal structure of a camel single-domain $V_H$ antibody fragment in complex with lysozyme", Nat. Struct. Biol., 3:803-811 (1996).

Desmyter, A. et al., "Three camelid VHH domains in complex with porcine pancreatic α-amylase: Inhibition and versatility of binding topology" The Journal of Biological Chemistry, 277:23645-23650 (2002).

Distenfano, M. et al., "Quantifying β-Sheet Stability by Phage Display", J. Mol. Biol., 322:179-188 (2002).

Dubaquié, Y. et al., "Total Alanine-Scanning Mutagenesis of Insulin-like Growth Factor 1 (IGF-1) Identifies Differential Binding Epitopes for IGFBP-1 and IGFBP-3", Biochemistry, 38:6386-6396 (1999).

Dumoulin, M. et al., "A camelid antibody fragment inhibits the formation of amyloid fibrils by human lysozyme", Nature, 424:783-788 (2003).

Dumoulin, M. et al., "Single-domain antibody fragments with high conformational stability", Nat. Struct. Biol., 11:500-515 (2002).

Eigenbrot et al., "X-ray Structures of the Antigen-binding Domains from Three Variants of Humanized anti-p185$^{HER2}$ Antibody 4D5 and Comparison with Molecular Modeling," J. Mol. Biol., 229:969-995 (1993).

Els Conrath, K. et al., "Camel single-domain antibodies as modular building units in bispecific and bivalent antibody constructs", J. Biol. Chem., 276:7346-7350 (2001).

Engels et al., "Gene Synthesis", Agnew. Chem. Int. Ed. Engl., 28:716-734 (1989).

Ewert, S. et al., "Biophysical properties of camelid $V_{HH}$ domains compared to those of human $V_H$3 domains", Biochemistry, 41:3628-3636 (2002).

Ewert, S. et al., "Biophysical properties of human antibody variable domains", J. Mol. Bio., 325:531-553 (2003).

Ferrat, G. et al., "A peptide mimic of an antigenic loop of α-human chorionic gonadotropin hormone: solution structure and interaction with a llama $V_{HH}$ domain", Biochem. J., 366:415-422 (2002).

Forsberg, G. et al., "Identification of Framework Residues in a Secreted Recombinant Antibody Fragment that Control Production Level and Localization in *Escherichia coli*", J. Biol. Chem., 272:12430-12436 (1997).

Froehler, B. et al., "Synthesis of DNA via deoxynucleoside H-phosphonate intermediates", Nucl. Acids Res., 14(13):5399-5407 (1986).

Fuh, G. et al., "Requirements for Binding and Signaling of the Kinase Domain Receptor for Vascular Endothelial Growth Factor", J. Biol. Chem., 273:11197-11204 (1998).

Garrard, L. et al., "Selection of an anti-IGF-1 Fab from a Fab phage library created by mutagenesis of multiple CDR loops", Gene, 128:103-109 (1993).

Glockshuber, R. et al., "A Comparison of Strategies to Stabilize Immunoglobulin $F_v$-Fragments", *Biochemistry*, 29:1362-1367 (1990).

Gregoret, L. et al., "Additivity of mutant effects assessed by binomial mutagenesis", *Proc. Natl. Acad. Sci. USA*, 90:4246-4250 (1993).

Griffiths et al., "Isolation of high affinity human antibodies directly from large synthetic repertoires", *The EMBO Journal*, 13(14):3245-3260 (1994).

Hamers-Casterman, C. et al., "Naturally occuring antibodies devoid of light chains", *Nature*, 363:446-448 (1993).

Harmsen, M. et al., "Llama heavy-chain V regions consist of at least four distinct subfamilies revealing novel sequence features", *Molecular Immunology*, 37:579-590 (2000).

Hawkins, R. et al., "Selection of Phage Antibodies by Binding Affinity: Mimicking Affinity Maturation", *J. Mol. Biol.*, 226:889-896 (1992).

Hollinger, P. et al., "Diabodies: Small bivalent and bispecific antibody fragments", *Proc. Natl. Acad. Sci. USA*, 90:6444-6448 (1993).

Honegger, A. et al., "Yet Another Numbering Scheme for Immunoglobulin Variable Domains: An Automatic Modeling and Analysis Tool", *J. Mol. Biol.*, 309:657-670 (2001).

Hoogenboom, "Antibody phage display technology and its applications", *Immunotechnology*, 4:1-20 (1988).

Hoogenboom, H., "Designing and optimizing library selection strategies for generating high-affinity antibodies", *Trends in Biotechnology*, 15:62-70, 1997.

Hoogenboom, H., "Overview of antibody phage-display technology and its applications", *Methods Mol. Biol.*, 178: 1-37 (2002).

Hoogenboom, H. et al., "By-passing Immunisation: Human Antibodies from Synthetic Repertoires of Germline $V_H$ Gene Segments Rearranged in Vitro", *J. Mol. Biol.*, 227:381-388 (1992).

Jackson, J. et al., "In Vitro Antibody Mutation: Improvement of a High Affinity, Neutralizing Antibody Against IL-1β", *The Journal of Immunology*, 154:3310-3319 (1995).

Jung, S. et al., "Selection for Improved Protein Stability by Phage Display", *J. Mol. Biol.*, 294:163-180 (1999).

Knappik, A. et al., "Fully Synthetic Human Combinatorial Antibody Libraries (HuCAL) Based on Modular Consensus Frameworks and CDRs Randomized with Trinucleotides", *J. Mol. Biol.*, 296:57-86 (2000).

Kostelny, S. et al., "Formation of a Bispecific Antibody by the Use of Leucine Zippers", *The Journal of Immunology*, 148(5):1547-1553 (1992).

Kunkel, T. et al., "Rapid and Efficient Site-Specific Mutagenesis without Phenotypic Selection", *Methods in Enzymology*, 154:367-382 (1987).

Ladner, R. et al., "Novel frameworks as a source of high-affinity ligands", *Curr. Opin. Biotechnol.*, 12:406-410 (2001).

Lee et al., "The Interpretation of Protein Structures: Estimation of Static Accessibility", *J. Mol. Biol.*, 55:379-400 (1971).

Lowman, H. et al., "Monovalent Phage Display: A Method for Selecting Variant Proteins from Random Libraries", *Methods: A Companion to Methods in Enzymology*, 3:205-216 (1991).

Lowman, H. et al., "Selecting High-Affinity Binding Proteins by Monovalent Phage Display", *Biochemistry*, 30:10832-10838 (1991).

Morrison, K. et al., "Combinatorial alanine-scanning", *Current Opinion in Chemical Biology*, 5:302-307 (2001).

Muyldermans, S. et al., "Sequence and structure of $V_H$ domain from naturally occuring camel heavy chain immunoglobulins lacking light chains", *Protein Eng.*, 7:1129-35 (1994).

Muyldermans, S., "Single domain camel antibodies: current status", *Journal of Biotechnology*, 74(4):277-302 (2001).

Nieba, L. et al., "Disrupting the hydrophobic patches at the antibody variable/constant domain interface: improved in vivo folding and physical characterization of an engineered scFv fragment", *Protein Engineering*, 10(4):435-444 (1997).

O'Neil, K. et al., "Phage display: protein engineering by directed evolution", *Current Opinion in Structural Biology*, 5:443-449 (1995).

Pacios, L. et al., "Arvomol/Contour: molecular surface areas and volumes on personal computers," *Computers Chem.*, 18(4):377-386 (1994).

Pacios, L., "Variations of Surface Areas and Volumes in Distinct Molecular Surfaces of Biomolecules", *Journal of Molecular Modeling*, 1: 46-53 (1995).

Pack, P. et al., "Miniantibodies: Use of Amphipathic Helices to Produce Functional, Flexibly Linked Dimeric $F_v$ Fragments with High Avidity in *Escherichia coli*", *Biochemistry*, 31(6):1579-1584 (1992).

Plückthun, A., "Antibodies from *Escherichia coli*", *The Pharmacology of Monoclonal Antibodies*, vol. 113, Rosenburg and Moore eds. Springer-Verlag, New York, pp. 269-315 (1994).

Presta, L. et al., "Humanization of an Anti-Vascular Endothelial Growth Factor Monoclonal Antibody for the Therapy of Solid Tumors and Other Disorders," *Cancer Research*, vol. 57, pp. 4593-4599 (Oct. 15, 1997).

Rader, C. et al., "Phage display of combinatorial antibody libraries", *Curr. Opin. Biotechnol.*, 8:503-508 (1997).

Renislo, J. et al., "Solution Structure and Backbone Dynamics of an Antigen-Free Heavy Chain Variable Domain (VHH) from *Llama*", *Proteins*, 47(4)546-555 (2002).

Sheriff, S. et al., "Redefining the minimal antigen-binding fragment", *Nat. Struct. Biol.*, 3:733-736 (1996).

Sidhu, S. et al., "Phage-displayed Antibody Libraries of Synthetic Heavy Chain Complementarity Determining Regions," *J. Mol. Biol.*, vol. 338, pp. 299-310 (2004).

Sidhu, S. et al., "High Copy Display of Large Proteins on Phage for Functional Selections", *J. Mol. Biol.*, 296:487-495 (2000).

Sidhu, S. et al., "Phage Display for Selection of Novel Binding Peptides", *Methods in Enzymology*, 328:333-363 (2000).

Sidhu, S., Phage Display in Pharmaceutical Biotechnology, *Curr. Opin. Biotechnol.*, 11:610-616 (2000).

Skerra, A. et al., "Assembly of a Functional Immunoglobulin $F_v$ Fragment in *Escherichia coli*", *Science*, 240:1038-1041 (1988).

Skerra, A., "Engineered protein scaffolds for molecular recognition", *Journal of Molecular Recognition*, 13:167-187 (2000).

Smith, G. et al., "Filamentous Fusion Phage: Novel Expression Vectors that Display Cloned Antigens on the Virion Surface", *Science*, 228:1315-1317 (1985).

Spinelli, S. et al., "Lateral recognition of a dye hapten by a llama VHH domain", *J. Mol. Bio.*, 311:123-129 (2001).

Spinelli, S. et al., "The crystal structure of a llama heavy chain variable domain", *Nature Structural Biology*, 3(9):752-757 (1996).

Tanha, J. et al., "Optimal Design Features of Camelized Human Single-domain Antibody Libraries," *The Journal of Biological Chemistry*, vol. 276, No. 27, Issue of Jul. 6, pp. 24774-24780 (2001).

Tanha, J. et al., "Selection by phage display of llama conventional V(H) fragments with heavy chain antibody V(H)H properties", *J. Imm. Meth.*, 263:97-109 (2002).

Ulrich, H. et al., "Expression studies of catalytic antibodies", *Proc. Nat'l Acad. Sci. USA*, 92:11907-11911 (1995).

Vajdos, F. et al., "Comprehensive functional maps of the antigen-binding site of an anti-ErbB2 antibody obtained with shotgun scanning mutagenesis", *J. Mol. Bio.*, 320:415-428 (2002).

van der Linden, R. et al., "Induction of immune responses and molecular cloning of the heavy chain antibody repertoire of *Lama glama*", *J. Imm. Meth.*, 240:185-195 (2000).

Vaughan et al., "Human Antibodies with Sub-nanomolar Affinities Isolated from a Large Non-immunized Phage Display Library", *Nat. Biotech*, 14:309-314 (1996).

Vranken, W. et al., "Solution structure of a llama single-domain antibody with hydrophobic residues typical of the VH/VL interface", *Biochemistry*, 41:8570-8579 (2002).

Weiss, G. et al., "Rapid mapping of protein functional epitopes by combinatorial alanine scanning", *Proc. Natl. Acad. Sci. USA*, 97(16):8950-8954 (2000).

Wells et al., "Rapid evolution of peptide and protein binding properties in vitro", *Curr. Opin. Struct. Biol.*, 3:355-362 (1992).

Wiesmann, C. et al., "Crystal Structure at 1.7 Å Resolution of VEGF in Complex with Domain 2 of the Flt-1 Receptor", *Cell*, 91:695-704 (1997).

Wu, T. et al., "Length distribution of CDRH3 in antibodies", *Proteins*, 16, 1-7 (1993).

Yelton, D. et al., "Affinity Maturation of the BR96 Anti-Carcinoma Antibody by Codon-Based Mutagenesis", *J. Immunol.*, 155:1994-2004 (1995).

Zapata, G. et al., "Engineering linear F(ab')₂ fragments for efficient production in *Escherichia coli* and enhanced antiproliferative activity", *Protein Eng.*, 8(10):1057-1062 (1995).

Zhu, Z. et al., "Remodeling domain interfaces to enhance heterodimer formation", *Protein Science*, 6:781-788 (1997).

International Search Report dated Nov. 18, 2004.

Amit, A. et al., "Three-Dimensional Structure of an Antigen-Antibody Complex at 2.8 Å Resolution", *Science*, 233:747-753 (1986).

Baca, M. et al., "Antibody Humanization Using Monovalent Phage Display", *J. Biol. Chem.*, 272:10678-10684 (1997).

Bassing, C. et al., "The Mechanism and Regulation of Chromosomal V(D)J Recombination", *Cell*, 109:S45-S55 (2002).

Bond, C. et al., "A Structure-Based Database of Antibody Variable Domain Diversity", *J. Mol. Biol.*, 348:699-709 (2005).

Bullock, W. et al., "XLI-Blue: A High Efficiency Plasmid Transforming recA *Escherichia coli* Strain With Beta-Galactosidase Selection", *BioTechniques*, 5:376-379 (1987).

Chang, C. et al., "High-Level Secretion of Human Growth Hormone by *Escherichia coli*", *Gene*, 55:189-196 (1987).

Chothia, C. et al., "Canonical Structures for the Hypervariable Regions of Immunoglobulins", *J. Mol. Biol.*, 196:901-917 (1987).

Chothia, C. et al., "Structural Repertoire of the Human $V_H$ Segments", *J. Mol. Biol.*, 227:799-817 (1992).

Crea, R. et al., "Chemical synthesis of genes for human insulin", *Proc. Natl. Sci. USA*, 75(12):5765-4769 (1978).

Davies, D. et al., "Interactions of protein antigens with antibodies", *Proc. Natl. Sci. USA*, 93:7-12 (1996).

Davis, B. et al., *Microbiology Including Immunology and Molecular Genetics*, Third Ed., pp. 237, 245-247, 374, 1981.

Enshell-Seijffers, D. et al., "The rational design of a 'type 88' genetically stable peptide display vector in the filamentous bacteriophage fd", *Nucleic Acids Research*, 29(10):1-13 (2001).

Ferrat et al., "A peptide mimic of an antigenic loop of α-human chorionic gonadotropin hormone: solution structure and interaction with a llama $V_{HH}$ domain", *Biochem. J.*, 366:415-422 (2002).

Graille, M. et al., "Crystal structure of a *Staphylococcus aureus* protein A domain complexed with the Fab fragment of a human IgM antibody: Structural basis for recognition of B-cell receptors and superantigen activity", *PNAS*, 97(10):5399-5404 (2000).

Harmsen, M. et al., "Llama heavy-chain V regions consist of at least four distinct subfamilies revealing novel sequence features", *Mol. Immunol.*, 37:579-590 (2000).

Harris, W., "Therapeutic Monoclonals", *Biochem. Soc. Transactions*, 23:1035-1038 (1995).

Hufton, S. et al., "Phage display of cDNA repertoires: the pVI display system and its applications for the selection of immunogenic ligands", *Journal of Immunological Methods*, 231:39-51 (1999).

Hurle, M. et al., "Protein engineering techniques for antibody humanization", *Curr. Op. Biotech.*, 5:428-433 (1994).

Jones, P. et al., "Replacing the complementarity-determining regions in a human antibody with those from a mouse", *Nature*, 321:522-525 (1986).

Kabat, E. et al., "Unusual Distributions of Amino Acids in Complementarity-determining (Hypervariable) Segments of Heavy and Light Chains of Immunoglobulins and Their Possible Roles in Specificity of Antibody-combining Sites", *The Journal of Biological Chemistry*, 252(19):6609-6616 (1977).

Kabat, E., "Antibody Diversity Versus Antibody Complementarity", *Pharmacological Rev.*, 34(1):23-38 (1982).

Kabat, E. et al., "Attempts to Locate Complementarity-Determining Residues in the Variable Positions of Light and Heavy Chain", *Annals New York Acad. Sci.*, 190:382-393 (1971).

Kyte, J. et al., "A Simple Method for Displaying the Hydropathic Character of a Protein", *J. Mol. Biol.*, 157:105-132 (1982).

Mian, I. et al., "Structure, Function and Properties of Antibody Binding Sites", *J. Mol. Biol.*, 217:133-151 (1991).

Morrison, S. et al., "Chimeric human antibody molecules: Mouse antigen-binding domains with human constant region domains", *PNAS*, 81:6851-6855 (1984).

Padlan, "Anatomy of the Antibody Molecule", *Mol. Immunol.*, 31(3):169-217 (1994).

Padlan, "Does Base Composition Help Predispose the Complementarity-Determining Regions of Antibodies to Hypermutation?", *Mol. Immunol.*, 34(11):765-770 (1997).

Pereboev, A. et al., "Phage Display of Adenovirus Type 5 Fiber Knob as a Tool for Specific Ligand Selection and Validation", *Journal of Virology*, 75(15):7107-7113 (2001).

Presta, L., "Antibody Engineering", *Curr. Op. Struct. Biol.*, 2:593-596 (1992).

Riechmann, L. et al., "Reshaping human antibodies for therapy", *Nature*, 332:323-329 (1988).

Rondot, S. et al., "A helper phage to improve single-chain antibody presentation in phage display", *Nature Biotechnology*, 19:75-78, 2001.

Stewart, J. et al., "A Shannon Entropy Analysis of Immunoglobulin and T Cell Receptor", *Mol. Immunol.*, 34(15):1067-1082 (1997).

Thompson, J. et al., "Clustal W: improving the sensitivity of progressive mutiple sequence alignment through sequence weighting, position-specific gap penalties and weight matrix choice", *Nucleic Acids Res.*, 22(22):4673-4680 (1994).

Tonegawa, S., "Somatic generation of antibody diversity", *Nature*, 302:575-581 (1983).

Vaswani, S. et al., "Humanized antibodies as potential therapeutic drugs", *Ann. Allergy, Asthma & Immunol.*, 8:105-115 (1998).

Viera, J. et al., "Production of Single-Stranded Plasmic DNA", *Meth. Enzymol.*, 153:3-11 (1987).

Weiss, G. et al., "Mutational analysis of the major coat protein of M13 identifies residues that control protein display", *Protein Science*, 9:647-654 (2000).

Wilson, P. et al., "Receptor Revision of Immunoglobulin Heavy Chain Variable Region Genes in Normal Human B Lymphocytes", *J. Exp. Med.*, 191(11):1881-1894 (2000).

Wong, E. et al., "Expression of secreted insulin-like growth factor-1 in *Escherichia coli*", *Gene*, 68:193-203 (1988).

Wu, T. et al., "An Analysis of the Sequences of the Variable Regions of Bence Jones Proteins and Myeloma Light Chains and Their Implications for Antibody Complementarity", *J. Exp. Med.*, 132:211-250 (1970).

Zemlin, M. et al., "Expressed Murine and Human CDR-H3 Intervals of Equal Length Exhibit Distinct Repertoires that Differ in their Amino Acid Composition and Predicted Range of Structures", *J. Mol. Biol.*, 334:733-749 (2003).

Zoller, M. et al., "Oligonucleotide-directed mutagenesis using M13-derived vectors: an efficient and general procedure for the production of point mutations in any fragment of DNA", *Nucleic Acids Res.*, 10(20):6487-6504 (1987).

\* cited by examiner

FIG. 4

| Position | R | K | N | D | Q | E | H | P | Y | S | W | T | G | A | M | C | F | L | V | I | Structure-Based | Shannon Entropy Human/Mouse | Shannon Entropy Llama |
|---|---|---|---|---|---|---|---|---|---|---|---|---|---|---|---|---|---|---|---|---|---|---|---|
| 23 | 4.9 | 2.5 | 3.3 | 9.1 | 7.4 | 4.1 | 4.9 | 0.8 | 6.6 | 7.1 | 0.0 | 9.9 | 2.9 | 5.4 | 3.3 | 0.0 | 7.4 | 5.2 | 10.3 | 4.9 | 4.0 | 2.1 | 1.9 |
| 24 | 0.2 | 2.1 | 0.7 | 3.5 | 0.7 | 2.8 | 3.5 | 0.7 | 9.1 | 2.8 | 4.9 | 1.4 | 1.4 | 5.9 | 7.0 | 3.5 | 13.3 | 6.7 | 15.0 | 14.7 | 3.8 | 1.7 | 1.4 |
| 25 | 2.6 | 11.1 | 5.5 | 6.3 | 2.4 | 1.6 | 1.6 | 4.3 | 7.9 | 11.8 | 2.4 | 7.1 | 4.7 | 3.6 | 4.7 | 0.8 | 5.5 | 5.8 | 3.9 | 6.3 | 4.1 | 0.6 | 0.7 |
| 26 | 3.3 | 0.8 | 8.4 | 9.2 | 3.1 | 5.4 | 3.1 | 3.8 | 5.4 | 8.1 | 2.3 | 5.4 | 10.8 | 5.4 | 5.4 | 1.5 | 3.1 | 1.8 | 6.9 | 4.6 | 4.1 | 0.3 | 0.9 |
| 27 | 3.9 | 3.1 | 9.5 | — | 2.3 | 3.9 | 7.7 | 6.8 | — | 7.4 | 6.2 | 5.0 | 5.0 | 10.4 | 5.4 | 3.2 | 5.6 | 2.8 | 5.0 | 2.3 | 4.2 | 1.9 | 3.2 |
| 28 | 3.4 | 1.6 | 6.0 | 12.0 | 2.2 | 3.2 | 4.5 | 6.8 | 4.0 | 6.8 | 1.6 | 6.4 | 5.6 | 4.0 | 4.8 | 2.3 | 9.0 | 2.7 | 6.0 | 5.6 | 4.2 | 1.8 | 2.6 |
| 29 | 1.7 | 2.2 | 9.5 | 7.1 | 6.8 | 3.0 | 4.5 | 8.2 | 9.0 | 5.5 | 4.5 | 5.2 | 9.0 | 3.7 | 2.2 | 0.8 | 9.0 | 2.7 | 4.9 | 2.2 | 4.2 | 1.4 | 2.6 |
| 30 | 5.0 | 4.5 | 3.8 | 6.0 | 6.8 | 3.0 | 7.5 | 5.3 | 4.5 | 8.0 | 5.3 | 4.9 | 4.5 | 5.3 | 2.3 | 1.5 | 6.6 | 4.6 | 4.1 | 5.3 | 4.2 | 1.8 | 2.7 |
| 31 | 2.2 | 0.7 | 13.2 | 11.7 | 5.1 | 5.1 | 5.9 | 8.8 | 1.5 | 4.8 | 4.4 | 5.5 | 5.1 | 2.2 | 2.9 | 0.7 | 6.6 | 6.3 | 5.9 | 2.2 | 4.0 | 2.3 | 3.5 |
| 32 | 2.2 | 3.7 | 5.1 | 15.4 | 2.2 | 2.9 | 5.9 | 2.9 | 11.0 | 5.9 | 2.2 | 7.3 | 4.4 | 3.7 | 2.9 | 1.5 | 5.1 | — | 4.0 | 3.7 | 4.1 | 2.0 | 2.8 |
| 33 | 1.9 | 0.0 | 8.6 | 1.4 | 5.0 | 1.4 | 1.4 | 1.8 | 11.5 | 1.9 | 10.1 | 8.3 | 4.3 | 6.1 | 2.9 | 2.1 | 4.3 | 1.9 | 7.2 | 6.5 | 4.0 | 3.1 | 3.4 |
| 34 | 0.0 | 0.0 | 0.7 | 0.0 | 0.0 | 1.4 | 0.0 | 0.0 | 7.1 | 6.4 | 6.4 | 2.5 | 0.0 | 4.3 | 6.4 | 2.1 | 18.6 | 6.6 | 19.7 | 19.3 | 3.3 | 2.2 | 1.6 |
| 35 | 0.0 | 0.8 | 3.1 | 0.8 | 1.5 | 2.3 | 2.3 | 0.0 | 12.3 | 7.4 | 3.8 | 3.8 | 13.0 | 11.9 | 6.9 | 0.0 | 11.5 | 1.5 | 9.6 | 7.7 | 3.7 | 3.0 | 2.2 |
| 51 | 0.0 | 0.6 | 0.6 | 6.5 | 0.6 | 0.0 | 2.3 | 0.3 | 5.9 | 5.0 | 1.8 | 2.1 | 0.9 | 3.8 | 7.6 | 1.8 | 28.1 | 12.7 | 7.9 | 17.0 | 3.3 | 1.0 | 1.1 |
| 52 | 4.5 | 0.7 | 1.4 | 0.0 | 3.6 | 2.1 | 2.9 | 1.8 | 7.9 | 16.5 | 2.1 | 7.5 | 0.6 | 3.6 | 5.0 | 1.4 | 9.3 | 9.5 | 7.5 | 0.7 | 3.9 | 3.2 | 3.2 |
| 52a | 1.4 | 0.6 | 5.0 | 3.3 | 1.9 | 6.4 | 6.5 | 1.6 | 4.4 | 12.1 | 5.7 | 3.5 | 2.5 | 5.0 | 2.5 | 2.5 | 15.7 | 4.8 | 5.0 | 4.4 | 4.0 | 2.8 | 3.4 |
| 53 | 3.2 | 0.0 | 2.5 | 5.4 | 1.3 | 1.9 | 5.0 | 1.6 | 8.3 | 11.8 | 3.8 | 1.9 | 10.1 | 4.1 | 4.5 | 1.4 | 14.0 | 5.5 | 6.0 | 4.5 | 4.0 | 3.3 | 3.1 |
| 54 | 3.2 | 0.7 | 4.8 | 8.3 | 3.4 | 3.3 | 3.2 | 5.4 | 4.1 | 16.0 | 2.2 | 2.7 | 6.0 | 4.5 | 4.1 | 2.5 | 7.5 | 6.2 | 3.1 | 2.7 | 4.0 | 2.7 | 1.8 |
| 55 | 2.2 | 0.0 | 7.3 | 8.9 | 1.3 | 4.1 | 6.7 | 5.0 | 3.3 | 12.9 | 2.7 | 2.1 | 13.0 | 6.3 | 1.3 | 2.7 | 8.7 | 5.1 | 3.0 | 4.0 | 3.9 | 2.1 | 3.2 |
| 56 | 4.6 | 1.3 | 4.4 | 4.4 | 7.0 | 2.3 | 8.2 | 1.9 | 5.1 | 10.9 | 2.5 | 5.7 | 4.4 | 5.4 | 5.7 | 1.9 | 13.9 | 5.1 | 3.8 | 3.8 | 4.0 | 3.2 | 3.1 |
| 71 | 5.6 | 0.6 | 0.6 | 0.0 | 0.6 | 0.0 | 2.3 | 0.8 | 14.1 | 2.0 | 8.4 | 0.3 | 0.8 | 2.3 | 4.5 | 19.7 | 28.7 | 4.8 | 7.9 | 2.3 | 3.2 | 2.3 | 1.7 |
| 72 | 0.9 | 0.6 | 7.6 | 63.1 | 0.0 | 1.8 | 2.9 | 0.3 | 0.0 | 13.0 | 0.0 | 1.8 | 0.6 | 3.2 | 0.6 | 0.6 | 1.2 | 0.8 | 7.5 | 0.6 | 2.1 | 0.7 | 0.7 |
| 73 | 7.8 | 1.6 | 2.4 | 7.3 | 1.6 | 4.9 | 6.5 | 1.8 | 4.9 | 10.0 | 1.6 | 3.2 | 2.4 | 7.3 | 0.0 | 0.0 | 2.4 | 4.5 | 5.0 | 1.6 | 3.8 | 2.3 | 1.6 |
| 74 | 3.5 | 1.4 | 3.5 | 29.0 | 3.5 | 4.8 | 4.1 | 2.1 | 2.1 | 12.2 | 0.7 | 2.1 | 6.0 | 7.3 | 3.5 | 0.8 | 4.8 | 4.6 | 6.6 | 2.1 | 3.6 | 2.5 | 1.3 |
| 75 | 9.2 | 5.7 | 5.8 | 9.0 | 2.2 | 4.8 | 8.7 | 4.5 | 4.6 | 16.0 | 1.6 | 7.8 | 10.6 | 6.5 | 0.8 | 0.0 | 4.9 | 4.3 | 1.6 | 2.1 | 3.9 | 1.6 | 1.2 |
| 76 | 12.2 | 9.9 | 6.1 | 8.4 | 2.3 | 3.3 | 3.0 | 7.3 | 3.3 | 13.0 | 0.0 | 1.1 | 15.6 | 1.9 | 1.5 | 0.8 | 2.3 | 0.8 | 0.0 | 0.8 | 3.6 | 1.6 | 1.4 |
| 77 | 5.3 | 3.0 | 1.5 | 0.8 | 1.3 | 3.8 | 3.0 | 0.4 | 1.5 | 4.6 | 1.4 | 12.9 | 0.8 | 3.8 | 3.8 | 0.8 | 6.1 | 7.1 | 25.0 | 12.1 | 3.6 | 1.8 | 1.1 |
| 78 | 0.2 | 0.0 | 0.0 | 4.4 | 7.0 | 2.3 | 0.0 | 0.4 | 0.0 | 3.9 | 1.4 | 2.1 | 0.0 | 2.5 | 4.2 | 21.0 | 22.4 | 17.0 | 15.8 | 9.1 | 2.9 | 2.2 | 1.5 |
| 98 | 3.5 | 1.6 | 4.1 | 6.5 | 0.8 | 4.1 | 4.9 | 4.1 | 7.3 | 8.6 | 3.2 | 3.2 | 9.7 | 2.8 | 1.6 | 1.7 | 17.8 | 5.7 | 3.2 | 4.9 | 4.0 | 3.7 | 4.0 |
| 99 | 4.8 | 1.7 | 3.4 | 3.3 | 2.6 | 6.0 | 9.4 | 5.6 | 6.8 | 10.2 | 0.9 | 2.1 | 8.1 | 4.7 | 1.7 | 0.8 | 10.2 | 7.7 | 4.7 | 2.6 | 4.1 | 3.7 | 3.9 |
| 100 | 4.6 | 3.3 | 5.7 | 5.4 | 1.6 | 3.3 | 8.2 | 7.0 | 6.5 | 9.2 | 7.4 | 2.0 | 3.3 | 4.5 | 2.5 | 0.8 | 11.5 | 7.6 | 4.5 | 3.3 | 4.1 | 3.7 | 4.0 |
| 100a | 2.3 | 3.9 | 3.9 | 5.1 | 3.1 | 3.1 | 3.1 | 4.6 | 8.5 | 4.3 | 1.5 | 2.3 | 5.4 | 6.6 | 1.5 | 3.9 | 13.2 | 7.7 | 8.5 | 7.0 | 4.0 | 3.8 | 4.0 |
| 100b | 3.1 | 0.7 | 5.8 | 8.3 | 3.1 | -1.5 | 2.9 | 3.6 | 7.3 | 4.8 | 6.5 | 3.6 | 4.4 | 3.6 | 2.9 | 2.3 | 21.1 | 5.5 | 5.8 | 8.0 | 4.0 | 3.9 | 4.0 |
| 100c | 3.5 | 2.3 | 6.1 | 8.9 | 2.3 | 2.3 | 0.9 | 3.8 | 4.6 | 6.5 | 4.0 | 3.0 | 6.1 | 3.8 | 4.6 | 3.2 | 15.9 | 5.8 | 5.3 | 9.9 | 4.0 | 3.9 | 4.0 |
| 100d | 4.0 | 4.0 | 5.5 | 8.3 | 1.6 | 1.8 | 8.7 | 4.8 | 5.5 | 4.8 | 4.0 | 5.4 | 4.0 | 5.1 | 5.5 | 0.9 | 13.5 | 8.9 | 4.8 | 3.2 | 4.0 | 3.9 | 4.1 |
| 100e | 5.9 | 0.0 | 7.2 | 4.5 | 1.8 | 1.8 | 3.0 | 5.4 | 5.4 | 12.2 | 5.4 | 2.9 | 4.5 | 1.8 | 6.3 | 0.8 | 11.6 | 6.8 | 4.5 | 5.4 | 4.0 | 3.9 | 4.0 |
| 100f | 5.0 | 2.5 | 5.5 | 3.4 | 0.8 | 2.5 | 6.7 | 5.4 | 6.7 | 11.1 | 4.2 | 4.0 | 6.3 | 6.3 | 3.4 | 1.6 | 13.4 | 4.2 | 3.4 | 3.4 | 4.1 | 3.8 | 4.1 |
| 100g | 2.9 | 3.2 | 5.6 | 9.6 | 3.2 | 2.4 | 5.6 | 8.0 | 6.4 | 6.6 | 3.2 | 2.1 | 2.4 | 6.0 | 8.0 | 1.6 | 7.2 | 4.8 | 7.6 | 1.6 | 4.2 | 3.6 | 3.9 |
| 100h | 5.6 | 1.7 | 9.3 | 5.9 | 4.2 | 4.2 | 5.9 | 7.2 | 8.5 | 8.1 | 0.8 | 2.1 | 6.8 | 3.4 | 3.4 | 0.0 | 10.2 | 5.9 | 4.2 | 2.5 | 4.1 | 2.4 | 3.9 |

SEQUENCE LISTING

<160> NUMBER OF SEQ ID NOS: 22

<210> SEQ ID NO 1
<211> LENGTH: 390
<212> TYPE: DNA
<213> ORGANISM: Artificial
<220> FEATURE:

```
<223> OTHER INFORMATION: Heavy chain variable domain

<400> SEQUENCE: 1
gatgttcagt tgcaggaatc aggcggtggc ttggtacagg ccggaggttc gttgcgtttg      60
tcctgtgctg cctcgggtcg tactggttct acttatgata tgggctggtt cgtcaggct     120 ccgggtaaag aacgtgaatc ggttgccgcc attaactggg attcggctcg tacttactat    180
gcttcgtccg tccgtggtcg tttactatt tcacgtgata atgccaaaaa aactgtctat    240
ttgcagatga attcattgaa accagaagat actgccgtct atacttgtgg tgctggtgaa    300
ggcggtactt gggattcttg gggtcagggt acccaggtca ctgtctcctc tgccggtggt    360
atggattata agatgatga tgataaatga                                      390

<210> SEQ ID NO 2
<211> LENGTH: 129
<212> TYPE: PRT
<213> ORGANISM: Artificial
<220> FEATURE:
<223> OTHER INFORMATION: Heavy chain variable domain

<400> SEQUENCE: 2

Asp Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Gly Ser Thr Tyr
            20                  25                  30

Asp Met Gly Trp Phe Arg Gln Ala Pro Gly Lys Glu Arg Glu Ser Val
        35                  40                  45

Ala Ala Ile Asn Trp Asp Ser Ala Arg Thr Tyr Tyr Ala Ser Ser Val
    50                  55                  60

Arg Gly Arg Phe Thr Ile Ser Arg Asp Asn Ala Lys Lys Thr Val Tyr
65                  70                  75                  80

Leu Gln Met Asn Ser Leu Lys Pro Glu Asp Thr Ala Val Tyr Thr Cys
                85                  90                  95

Gly Ala Gly Glu Gly Gly Thr Trp Asp Ser Trp Gly Gln Gly Thr Gln
            100                 105                 110

Val Thr Val Ser Ser Ala Gly Gly Met Asp Tyr Lys Asp Asp Asp Asp
            115                 120                 125

Lys

<210> SEQ ID NO 3
<211> LENGTH: 17
<212> TYPE: PRT
<213> ORGANISM: Artificial
<220> FEATURE:
<223> OTHER INFORMATION: CDRH3 sequence

<400> SEQUENCE: 3

Arg Ile Gly Arg Ser Val Phe Asn Leu Arg Arg Glu Ser Trp Val Thr
1               5                   10                  15

Trp

<210> SEQ ID NO 4
<211> LENGTH: 17
<212> TYPE: PRT
<213> ORGANISM: Artificial
<220> FEATURE:
<223> OTHER INFORMATION: CDRH3 sequence

<400> SEQUENCE: 4
```

```
Leu Leu Arg Arg Gly Val Asn Ala Thr Pro Asn Trp Phe Gly Leu Val
1               5                   10                  15

Gly

<210> SEQ ID NO 5
<211> LENGTH: 17
<212> TYPE: PRT
<213> ORGANISM: Artificial
<220> FEATURE:
<223> OTHER INFORMATION: CDRH3 sequence

<400> SEQUENCE: 5

Val Leu Lys Arg Arg Gly Ser Ser Val Ala Ile Phe Thr Arg Val Gln
1               5                   10                  15

Ser

<210> SEQ ID NO 6
<211> LENGTH: 17
<212> TYPE: PRT
<213> ORGANISM: Artificial
<220> FEATURE:
<223> OTHER INFORMATION: CDRH3 sequence

<400> SEQUENCE: 6

Arg Leu Val Asn Gly Leu Ser Gly Leu Val Ser Trp Glu Met Pro Leu
1               5                   10                  15

Ala

<210> SEQ ID NO 7
<211> LENGTH: 22
<212> TYPE: PRT
<213> ORGANISM: Artificial
<220> FEATURE:
<223> OTHER INFORMATION: CDRH3
<220> FEATURE:
<221> NAME/KEY: MISC_FEATURE
<222> LOCATION: (5)..(5)
<223> OTHER INFORMATION: Xaa is Arg, Leu, Val, Phe, Trp and Lys
<220> FEATURE:
<221> NAME/KEY: MISC_FEATURE
<222> LOCATION: (6)..(6)
<223> OTHER INFORMATION: Xaa is Ile, Leu, Val, Arg, Trp and Ser
<220> FEATURE:
<221> NAME/KEY: MISC_FEATURE
<222> LOCATION: (7)..(17)
<223> OTHER INFORMATION: Xaa is any amino acid
<220> FEATURE:
<221> NAME/KEY: MISC_FEATURE
<222> LOCATION: (18)..(18)
<223> OTHER INFORMATION: Xaa is Trp, Gly, Arg, Met, Ser, Ala and His
<220> FEATURE:
<221> NAME/KEY: MISC_FEATURE
<222> LOCATION: (19)..(19)
<223> OTHER INFORMATION: Xaa is Val, Leu, Pro, Gly, Ser, Glu and Trp
<220> FEATURE:
<221> NAME/KEY: MISC_FEATURE
<222> LOCATION: (20)..(21)
<223> OTHER INFORMATION: Xaa is any amino acid

<400> SEQUENCE: 7

Cys Gly Ala Gly Xaa Xaa Xaa Xaa Xaa Xaa Xaa Xaa Xaa Xaa Xaa
1               5                   10                  15

Xaa Xaa Xaa Xaa Xaa Asp
            20

<210> SEQ ID NO 8
<211> LENGTH: 22
<212> TYPE: PRT
```

```
<213> ORGANISM: Artificial
<220> FEATURE:
<223> OTHER INFORMATION: CDRH3
<220> FEATURE:
<221> NAME/KEY: MISC_FEATURE
<222> LOCATION: (7)..(17)
<223> OTHER INFORMATION: Xaa is any amino acid

<400> SEQUENCE: 8

Cys Gly Ala Gly Arg Ile Xaa Xaa Xaa Xaa Xaa Xaa Xaa Xaa Xaa
1               5                   10                  15

Xaa Trp Val Thr Trp Asp
            20

<210> SEQ ID NO 9
<211> LENGTH: 35
<212> TYPE: PRT
<213> ORGANISM: Artificial
<220> FEATURE:
<223> OTHER INFORMATION: Dimerization sequence

<400> SEQUENCE: 9

Gly Arg Met Lys Gln Leu Glu Asp Lys Val Glu Glu Leu Leu Ser Lys
1               5                   10                  15

Asn Tyr His Leu Glu Asn Glu Val Ala Arg Leu Lys Lys Leu Val Gly
            20                  25                  30

Glu Arg Gly
        35

<210> SEQ ID NO 10
<211> LENGTH: 8
<212> TYPE: PRT
<213> ORGANISM: Artificial
<220> FEATURE:
<223> OTHER INFORMATION: FR3 sequence
<220> FEATURE:
<221> NAME/KEY: MISC_FEATURE
<222> LOCATION: (1)..(1)
<223> OTHER INFORMATION: Xaa is Leu, Met, Trp, Tyr, Phe or Cys
<220> FEATURE:
<221> NAME/KEY: MISC_FEATURE
<222> LOCATION: (2)..(2)
<223> OTHER INFORMATION: Xaa is Asp, Asn or Ser
<220> FEATURE:
<221> NAME/KEY: MISC_FEATURE
<222> LOCATION: (3)..(7)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is Ile, Val, Met, Phe or Cys

<400> SEQUENCE: 10

Xaa Xaa Xaa Xaa Xaa Xaa Xaa Xaa
1               5

<210> SEQ ID NO 11
<211> LENGTH: 4
<212> TYPE: PRT
<213> ORGANISM: Artificial
<220> FEATURE:
<223> OTHER INFORMATION: FR3 sequence
<220> FEATURE:
<221> NAME/KEY: MISC_FEATURE
<222> LOCATION: (1)..(1)
<223> OTHER INFORMATION: Xaa is Cys, Phe or Tyr
<220> FEATURE:
<221> NAME/KEY: MISC_FEATURE
<222> LOCATION: (2)..(2)
<223> OTHER INFORMATION: Xaa is Asp, Ser or Asn
```

```
<220> FEATURE:
<221> NAME/KEY: MISC_FEATURE
<222> LOCATION: (3)..(3)
<223> OTHER INFORMATION: Xaa is any amino acid; n is 5 to 15 contiguous
      amino acids
<220> FEATURE:
<221> NAME/KEY: MISC_FEATURE
<222> LOCATION: (4)..(4)
<223> OTHER INFORMATION: Xaa is Cys and Phe

<400> SEQUENCE: 11

Xaa Xaa Xaa Xaa
1

<210> SEQ ID NO 12
<211> LENGTH: 4
<212> TYPE: PRT
<213> ORGANISM: Artificial
<220> FEATURE:
<223> OTHER INFORMATION: FR3 sequence
<220> FEATURE:
<221> NAME/KEY: MISC_FEATURE
<222> LOCATION: (1)..(1)
<223> OTHER INFORMATION: Xaa is an amino acid selected from the group
      consisting of Leu, Ile, Val, Trp, Tyr, Phe, and Cys
<220> FEATURE:
<221> NAME/KEY: MISC_FEATURE
<222> LOCATION: (2)..(2)
<223> OTHER INFORMATION: Xaa is an amino acid selected from the group
      consisting of Asp, Ser, and Asn
<220> FEATURE:
<221> NAME/KEY: MISC_FEATURE
<222> LOCATION: (3)..(3)
<223> OTHER INFORMATION: Xaa is any amino acid, n is 5 to 15 contiguous
      amino acids
<220> FEATURE:
<221> NAME/KEY: MISC_FEATURE
<222> LOCATION: (4)..(4)
<223> OTHER INFORMATION: Xaa is an amino acid selected from the group
      consisting of Leu, Ile, Val, Trp, Tyr, Phe, and Cys

<400> SEQUENCE: 12

Xaa Xaa Xaa Xaa
1

<210> SEQ ID NO 13
<211> LENGTH: 8
<212> TYPE: PRT
<213> ORGANISM: Artificial
<220> FEATURE:
<223> OTHER INFORMATION: FR3 sequence
<220> FEATURE:
<221> NAME/KEY: MISC_FEATURE
<222> LOCATION: (1)..(1)
<223> OTHER INFORMATION: Xaa is an amino acid selected from the group
      consisting of Leu, Ile, Val, Trp, Tyr, Phe, and Cys
<220> FEATURE:
<221> NAME/KEY: MISC_FEATURE
<222> LOCATION: (2)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is an amino acid selected from the group
      consisting of Ile, Thr, and Val
<220> FEATURE:
<221> NAME/KEY: MISC_FEATURE
<222> LOCATION: (8)..(8)
<223> OTHER INFORMATION: Xaa is an amino acid selected from the group
      consisting of Leu, Ile, Val, Trp, Tyr, Phe, and Cys

<400> SEQUENCE: 13

Xaa Xaa Xaa Xaa Xaa Xaa Xaa Xaa
1               5
```

<210> SEQ ID NO 14
<211> LENGTH: 8
<212> TYPE: PRT
<213> ORGANISM: Artificial
<220> FEATURE:
<223> OTHER INFORMATION: FR3 sequence
<220> FEATURE:
<221> NAME/KEY: MISC_FEATURE
<222> LOCATION: (1)..(1)
<223> OTHER INFORMATION: Xaa is an amino acid selected from the group
      consisting of Leu, Met, Trp, Tyr, Phe, and Cys
<220> FEATURE:
<221> NAME/KEY: MISC_FEATURE
<222> LOCATION: (2)..(2)
<223> OTHER INFORMATION: Xaa is Asp
<220> FEATURE:
<221> NAME/KEY: MISC_FEATURE
<222> LOCATION: (3)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is an amino acid selected from the group
      consisting of Ile, Thr, and Val
<220> FEATURE:
<221> NAME/KEY: MISC_FEATURE
<222> LOCATION: (8)..(8)
<223> OTHER INFORMATION: Xaa is an amino acid selected from the group
      consisting of Met, Ile, Val, Phe, and Cys

<400> SEQUENCE: 14

Xaa Xaa Xaa Xaa Xaa Xaa Xaa Xaa
1               5

<210> SEQ ID NO 15
<211> LENGTH: 8
<212> TYPE: PRT
<213> ORGANISM: Artificial
<220> FEATURE:
<223> OTHER INFORMATION: FR3 sequence
<220> FEATURE:
<221> NAME/KEY: MISC_FEATURE
<222> LOCATION: (1)..(1)
<223> OTHER INFORMATION: Xaa is an amino acid selected from the group
      consisting of Tyr, Phe, and Cys
<220> FEATURE:
<221> NAME/KEY: MISC_FEATURE
<222> LOCATION: (2)..(2)
<223> OTHER INFORMATION: Xaa is Asp
<220> FEATURE:
<221> NAME/KEY: MISC_FEATURE
<222> LOCATION: (3)..(3)
<223> OTHER INFORMATION: Xaa is an amino acid selected from the group
      consisting of Ala, Asp, Pro, Arg, and Ser
<220> FEATURE:
<221> NAME/KEY: MISC_FEATURE
<222> LOCATION: (4)..(4)
<223> OTHER INFORMATION: Xaa is an amino acid selected from the group
      consisting of Ala, Asp, and Ser
<220> FEATURE:
<221> NAME/KEY: MISC_FEATURE
<222> LOCATION: (5)..(5)
<223> OTHER INFORMATION: Xaa is an amino acid selected from the group
      consisting of Asp, Gly, Arg, Ala, and Thr
<220> FEATURE:
<221> NAME/KEY: MISC_FEATURE
<222> LOCATION: (6)..(6)
<223> OTHER INFORMATION: Xaa is an amino acid selected from the group
      consisting of Gly, Lys, Arg, and His
<220> FEATURE:
<221> NAME/KEY: MISC_FEATURE
<222> LOCATION: (7)..(7)
<223> OTHER INFORMATION: Xaa is an amino acid selected from the group
      consisting of Ile, Leu, and Val
<220> FEATURE:

```
<221> NAME/KEY: MISC_FEATURE
<222> LOCATION: (8)..(8)
<223> OTHER INFORMATION: Xaa is an amino acid selected from the group
      consisting of Phe and Cys

<400> SEQUENCE: 15

Xaa Xaa Xaa Xaa Xaa Xaa Xaa Xaa
1               5

<210> SEQ ID NO 16
<211> LENGTH: 4
<212> TYPE: PRT
<213> ORGANISM: Artificial
<220> FEATURE:
<223> OTHER INFORMATION: FR3 sequence
<220> FEATURE:
<221> NAME/KEY: MISC_FEATURE
<222> LOCATION: (1)..(1)
<223> OTHER INFORMATION: Xaa is Cys, Phe, or Tyr
<220> FEATURE:
<221> NAME/KEY: MISC_FEATURE
<222> LOCATION: (2)..(2)
<223> OTHER INFORMATION: Xaa is Asp or Glu
<220> FEATURE:
<221> NAME/KEY: MISC_FEATURE
<222> LOCATION: (3)..(3)
<223> OTHER INFORMATION: Xaa is any amino acid, n is 1 to 20 amino acids
<220> FEATURE:
<221> NAME/KEY: MISC_FEATURE
<222> LOCATION: (4)..(4)
<223> OTHER INFORMATION: Xaa is Leu, Phe, or Cys

<400> SEQUENCE: 16

Xaa Xaa Xaa Xaa
1

<210> SEQ ID NO 17
<211> LENGTH: 4
<212> TYPE: PRT
<213> ORGANISM: Artificial
<220> FEATURE:
<223> OTHER INFORMATION: FR3 sequence
<220> FEATURE:
<221> NAME/KEY: MISC_FEATURE
<222> LOCATION: (3)..(3)
<223> OTHER INFORMATION: Xaa is any amino acid, n is 1 to 20 amino acids

<400> SEQUENCE: 17

Cys Asp Xaa Cys
1

<210> SEQ ID NO 18
<211> LENGTH: 8
<212> TYPE: PRT
<213> ORGANISM: Artificial
<220> FEATURE:
<223> OTHER INFORMATION: FR3 sequence
<220> FEATURE:
<221> NAME/KEY: MISC_FEATURE
<222> LOCATION: (1)..(1)
<223> OTHER INFORMATION: Xaa is Leu, Ile, Val Trp, Tyr or Phe
<220> FEATURE:
<221> NAME/KEY: MISC_FEATURE
<222> LOCATION: (2)..(7)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is Leu, Ile, Val, Trp, Tyr or Phe

<400> SEQUENCE: 18

Xaa Xaa Xaa Xaa Xaa Xaa Xaa Xaa
```

```
<210> SEQ ID NO 19
<211> LENGTH: 8
<212> TYPE: PRT
<213> ORGANISM: Artificial
<220> FEATURE:
<223> OTHER INFORMATION: FR3 sequence
<220> FEATURE:
<221> NAME/KEY: MISC_FEATURE
<222> LOCATION: (1)..(1)
<223> OTHER INFORMATION: Xaa is Cys, Phe, Tyr, Trp, Met or Leu
<220> FEATURE:
<221> NAME/KEY: MISC_FEATURE
<222> LOCATION: (2)..(2)
<223> OTHER INFORMATION: Xaa is Asp, Asn or Ser
<220> FEATURE:
<221> NAME/KEY: MISC_FEATURE
<222> LOCATION: (3)..(7)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is Met, Cys, Phe, Val or Ile

<400> SEQUENCE: 19

Xaa Xaa Xaa Xaa Xaa Xaa Xaa Xaa
1               5

<210> SEQ ID NO 20
<211> LENGTH: 8
<212> TYPE: PRT
<213> ORGANISM: Artificial
<220> FEATURE:
<223> OTHER INFORMATION: FR3 sequence
<220> FEATURE:
<221> NAME/KEY: MISC_FEATURE
<222> LOCATION: (1)..(1)
<223> OTHER INFORMATION: Xaa is Cys, Phe, Tyr, Met or Leu
<220> FEATURE:
<221> NAME/KEY: MISC_FEATURE
<222> LOCATION: (2)..(2)
<223> OTHER INFORMATION: Xaa is Asp or Glu
<220> FEATURE:
<221> NAME/KEY: MISC_FEATURE
<222> LOCATION: (3)..(7)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is Met, Cys, Phe, Val or Ile

<400> SEQUENCE: 20

Xaa Xaa Xaa Xaa Xaa Xaa Xaa Xaa
1               5

<210> SEQ ID NO 21
<211> LENGTH: 4
<212> TYPE: PRT
<213> ORGANISM: Artificial
<220> FEATURE:
<223> OTHER INFORMATION: FR3 sequence
<220> FEATURE:
<221> NAME/KEY: MISC_FEATURE
<222> LOCATION: (1)..(1)
<223> OTHER INFORMATION: Xaa is Cys, Phe, Tyr, Trp, Met or Leu
<220> FEATURE:
<221> NAME/KEY: MISC_FEATURE
<222> LOCATION: (2)..(2)
<223> OTHER INFORMATION: Xaa is Asp, Asn or Ser
<220> FEATURE:
<221> NAME/KEY: MISC_FEATURE
<222> LOCATION: (3)..(3)
<223> OTHER INFORMATION: Xaa is any amino acid, n = 5 to 15 contiguous
```

```
        amino acids
<220> FEATURE:
<221> NAME/KEY: MISC_FEATURE
<222> LOCATION: (4)..(4)
<223> OTHER INFORMATION: Xaa is Met, Cys, Phe, Val or Ile

<400> SEQUENCE: 21

Xaa Xaa Xaa Xaa
1

<210> SEQ ID NO 22
<211> LENGTH: 4
<212> TYPE: PRT
<213> ORGANISM: Artificial
<220> FEATURE:
<223> OTHER INFORMATION: FR3 sequence
<220> FEATURE:
<221> NAME/KEY: MISC_FEATURE
<222> LOCATION: (1)..(1)
<223> OTHER INFORMATION: Xaa is Cys, Phe or Tyr
<220> FEATURE:
<221> NAME/KEY: MISC_FEATURE
<222> LOCATION: (2)..(2)
<223> OTHER INFORMATION: Xaa is Asp or Glu
<220> FEATURE:
<221> NAME/KEY: MISC_FEATURE
<222> LOCATION: (3)..(3)
<223> OTHER INFORMATION: Xaa is any amino acid, n is 5 to 15 contiguous
        amino acids
<220> FEATURE:
<221> NAME/KEY: MISC_FEATURE
<222> LOCATION: (4)..(4)
<223> OTHER INFORMATION: Xaa is Cys, Phe or Leu

<400> SEQUENCE: 22

Xaa Xaa Xaa Xaa
1
```

VARIABLE DOMAIN LIBRARY AND USES

CROSS REFERENCE TO RELATED APPLICATION

This application claims priority under 35 USC 119(e) to U.S. Application Ser. No. 60/560,949 filed Apr. 9, 2004, which application is hereby incorporated by reference.

FIELD OF THE INVENTION

The invention generally relates to libraries of antibodies or antibody variable domains. The libraries include a plurality of different antibody variable domains generated by creating diversity in a heavy chain variable framework domain (VFR), and optionally, one or more complementary determining regions (CDRs). In particular, diversity in VFR is designed to maximize antigen binding while minimizing the structural perturbations of the antibody variable domain. The invention also relates to fusion polypeptides of one or more antibody variable domain and a heterologous protein such as a coat protein of a virus. The invention also relates to replicable expression vectors which include a gene encoding the fusion polypeptide, host cells containing the expression vectors, a virus which displays the fusion polypeptide on the surface of the virus, libraries of the virus displaying a plurality of different fusion polypeptides on the surface of the virus and methods of using those compositions. The methods and compositions of the invention are useful for identifying novel antibodies and antibody variable domains that can be used therapeutically or as reagents.

BACKGROUND

The vertebrate immune system can evolve antibodies capable of recognizing essentially any macromolecule with high affinity and specificity. Analyses of natural antibody sequences together with structural studies have been instrumental in revealing how antibodies work (Chothia et al., 1992, J. Mol. Biol., 227: 799-817; Kabat, 1982, Pharmacological Rev., 34: 23-38; Kabat, 1987, Sequences of Proteins of Immunological Interest (National Institutes of Health, Bethesda, Md.)). These studies have revealed that antigen recognition is primarily mediated by complementarity determining regions (CDRs) that are located at one end of the antibody variable domain and are connected by a β-sheet framework (Wu & Kabat, 1970, J. Exp. Med., 132: 211-250; Kabat & Wu, 1971, Annals New York Acad. Sci., 190: 382-393). The sequence diversity of natural antibodies shows that the CDRs are hypervariable in comparison with the framework, and it is the CDR sequences that determine the antigen specificity of a particular antibody (Jones et al., 1986, Nature, 321: 522-5; Amit et al., 1986, Science, 233: 747-53). These studies have also revealed that the natural sequence diversity at most CDR positions is not completely random, as biases for particular amino acids occur in both a site-specific manner and in terms of overall CDR composition (Davies & Cohen, 1996, Proc. Natl. Acad. Sci. USA, 93: 7-12; Kabat et al., 1977, J. Biol. Chem., 252: 6609-16; Zemlin et al., 2003, J. Mol. Biol., 334: 733-49; Mian et al., 1991, J. Mol. Biol., 217: 133-51; Padlan, 1994, Mol. Immunol., 31: 169-217).

The diversity of antibody variable domains is generated by several distinct genetic mechanisms (Zemlin et al., 2003; Bassing et al., 2002, Cell, 109: S45-55; Tonegawa, 1983, Nature, 302: 575-81; Padlan, 1997, Mol. Immunol., 34: 765-70; Wilson, 2000, J. Exp. Med., 191: 1881-94). Diversity is encoded in the collection of V genes in the germline and further generated through recombination of V, D and J segments in B cells. Recombination generates variability in amino acid content in all CDRs and variation in the length of the loop portion of CDR3. Finally, somatic hypermutation during the secondary immune response generates diversity throughout variable domains. While these genetic mechanisms allow sufficient diversity to generate a biologically competent immune repertoire, they also likely constrain natural diversity as compared to the level of diversity created through a purely random process.

Phage display is a powerful technique that has been utilized to identify novel antigen binding antibody variable domains. The ability to identify and isolate high affinity antibodies from a phage display library is important in isolating novel human antibodies for therapeutic use. Isolation of high affinity antibodies from a library is dependent on the size of the library, the efficiency of production in cells, and the diversity of the library. See, for e.g., Knappik et al., J. Mol. Biol. (1999), 296:57. The size of the library is decreased by inefficiency of production due to improper folding of the antibody or antigen binding protein and the presence of stop codons. Expression in bacterial cells can be inhibited if the antibody or antigen binding domain is not properly folded. In some cases, expression can be improved by mutating residues in turns at the surface of the variable/constant interface, or at selected CDR residues. (Deng et al., J. Biol. Chem. (1994), 269:9533, Ulrich et al., PNAS (1995), 92:11907-11911; Forsberg et al., J. Biol. Chem. (1997), 272:12430). The sequence of the framework region is important in providing for proper folding when antibody phage libraries are produced in bacterial cells. However, not all strategies provide a library of diverse but structurally stable antibody variable domains.

Understanding the structural constraints of diversified antibody variable domains may contribute to providing a library of diverse yet structurally stable antibody variable domains that can bind to a target antigen with high affinity. Such a library and the antibody variable domains isolated from the library are useful as novel antigen binding molecules for use, for example, therapeutically and for ease of production of antibodies or antigen binding fragments on a large scale.

SUMMARY OF INVENTION

The present invention provides methods of systematically and efficiently generating polypeptides comprising diversified FR and/or CDRs. Unlike conventional methods that propose that adequate diversity of target binders can be generated only if a particular CDR(s), or all CDRs should be diversified, and unlike conventional notions that adequate diversity is dependent upon the broadest range of amino acid substitutions (generally by substitution using all or most of the 20 amino acids), the invention provides methods capable of generating high quality target binders that are not necessarily dependent upon diversifying a particular CDR(s) or a particular number of CDRs of a reference polypeptide or source antibody. The invention is based, at least in part, on the surprising and unexpected findings that highly diverse libraries of high quality can be generated by limiting the diversity at structural amino acid positions and diversifying nonstructural amino acid positions in a CDR and/or VFR. Methods of the invention are convenient, based on objective and systematic criteria, and rapid. The methods and polypeptides of the invention are useful in the isolation of high affinity binding molecules to target antigens and to provide for well folded antibody variable domains that can readily be adapted to large scale production.

In naturally occurring antibody variable domains, the CDRs participate in antigen binding and vary between antibodies. The framework regions form β sheet structures that help to form the antigen binding pocket and typically that have less diversity. One aspect of the invention involves generating a plurality of antibody variable domains that have at least a portion of a framework region that is diversified. In some embodiments, the framework region residues are those residues that are solvent accessible and preferably, form part of an antigen binding domain or loop.

One aspect of the invention provides a polypeptide comprising a variant VFR region, wherein the VFR region comprises at least one structural amino acid position in the VFR region, wherein said structural amino acid position has a variant amino acid that is an amino acid found at that position in a randomly generated VFR population at a frequency of at least one standard deviation above the average frequency for any amino acid at that position; and at least one nonstructural position in the VFR. In some embodiments, the variant amino acid comprises or is selected from the group consisting of hydrophobic amino acids and/or a cysteine. The nonstructural position has a variant amino acid that can be any one of the naturally occurring amino acids or an amino acid encoded by a non-random codon set including, but not limited to, codon sets designated NNS and NNK. Diversity is more limited at the structural amino acid positions and in some embodiments, the structural amino acid positions determine the boundaries of a contiguous amino acid sequence that can be varied randomly, if desired. In some embodiments, the VFR region amino acid positions are those framework amino acid positions that are solvent accessible and/or form a loop in an antigen binding pocket. In some embodiments, the VFR amino acid positions correspond to amino acid positions 71-78 in a variable domain. In some embodiments, the variable domain is the heavy chain variable domain.

In some embodiments, the structural amino acid positions of the VFR comprise, consist essentially of, or consist of one or both of the first two amino acid positions at the N-terminus of a VFR region and/or the last amino acid position at the C-terminus of a VFR. The structural amino acid positions can be substituted with up to six different amino acids so have a variant amino acid in that position. In some embodiments, the variant amino acid comprises or is selected from the group consisting of up to six different amino acids, preferably no more than six different amino acids, more preferably about 1 to 5 different amino acids, more preferably about 1 to 4 different amino acids, more preferably about 1 to 3 different amino acids, and more preferably about 1-2 different amino acids. Preferably, the structural amino acid positions are substituted with a hydrophobic amino acid or a cysteine. Preferably, the variant amino acids in the structural amino acid position are encoded by a nonrandom codon set that encodes up to six different amino acids or less. In some embodiments, the non random codon set encodes one or more of a set of hydrophobic amino acids such as F, Y, W, L, V, I, or M and/or cysteine.

In other embodiments, the first N-terminal amino acid position has a variant amino acid selected from the group consisting of C, F, and Y. Preferably, the first N terminal amino acid position corresponds to position 71 in a variable heavy chain domain. The second amino acid position at the N-terminus is selected from the group consisting of D and E, and preferably corresponds to position 72 in a variable heavy chain. Preferably, the amino acid at the C terminus corresponds to an amino acid position 78 of a variable heavy chain domain. In some embodiments, the structural amino acid position at the N-terminus amino acid position of VFR is C, F, or Y, the structural amino acid position at the position second from the N-terminus is D or E; the structural amino acid position at the C-terminus is C, F, or L; and the nonstructural amino acid positions are contiguous amino acids between the second amino acid position from the N-terminus position and the C-terminus position and are substituted with any of the 20 amino acids. In some embodiments, the structural amino acid at the C terminus of the VFR is C or F. In some embodiments, the structural amino acid positions at positions 71 and 78 are cysteines.

In some embodiments, the nonstructural amino acid is a contiguous amino acid sequence that can be varied randomly, if desired. In some embodiments, the nonstructural amino acids are a contiguous amino acid sequence of up to 20 amino acids, preferably no more than 20 amino acids, more preferably about 1 to 19 amino acids, more preferably about 1 to 18 amino acids, more preferably about 1 to 17 amino acids, more preferably about 1 to 16 amino acids, more preferably about 1 to 15 amino acids, more preferably about 1 to 14 amino acids, more preferably about 1 to 13 amino acids, more preferably about 1 to 12 amino acids, more preferably about 1 to 11 amino acids, more preferably about 1 to 10 amino acids, more preferably about 1 to 9 amino acids, more preferably about 1 to 8 amino acids, more preferably about 1 to 7 amino acids, more preferably about 1 to 6 amino acids, more preferably about 1 to 5 amino acids, more preferably about 1 to 4 amino acids, more preferably about 1 to 3 amino acids, more preferably about 1 to 2 amino acids. In some embodiments, these amino acid positions can be substituted randomly using a codon set, for example, such as NNK or NNS that encode all amino acids. The nonstructural amino acid positions can accommodate all of the amino acids and preferably, do not exclude any amino acid. In other embodiments, the variant amino acids can be encoded by a nonrandom codon set.

The invention also provides polypeptides comprising a variant VFR region, wherein the VFR region comprises a N terminal portion that has at least one structural amino acid position having a variant amino acid, wherein the variant amino acid is an amino acid found at that position in a randomly generated VFR population at a frequency of at least one standard deviation above the average frequency for any amino acid at that position; a central portion that has at least one nonstructural position having a variant amino acid; and a C-terminal portion that has at least one structural amino acid position having a variant amino acid, wherein the variant amino acid is an amino acid found at that position in a randomly generated VFR population at a frequency of at least one standard deviation above the average frequency for any amino acid at that position and the amino acid positions of the VFR region are solvent accessible and/or form a loop in an antigen binding pocket. In some embodiments, the central portion has at least 5 amino acid positions that can be varied randomly. In some embodiments, the VFR amino acid positions correspond to amino acid positions 71-78 of a variable heavy chain domain. Preferably, the VFR is well folded and stable for phage display.

In some embodiments, the diversity at the structural amino acid positions is limited. The structural amino acid position can be substituted with up to six different amino acids. The variant amino acid in the structural amino acid position comprises or is an amino acid selected from the group consisting of 6 of the most commonly occurring amino acids at that position in a randomly generated population, preferably no more than six different amino acids. More preferably, the structural amino acid position is substituted with about 1 to 6 different amino acids, about 1 to 5 different amino acids, about 1 to 4 different amino acids, about 1 to 3 different amino acids, or about 1-2 different amino acids. Preferably, the N and/or C terminal amino acid positions are substituted with a cysteine and/or one or more hydrophobic amino acids selected from the group consisting of F, W, Y, M, L, V, or I.

Another aspect of the invention provides polypeptides altered to include one or more changes in a core amino acid sequence of VFR. Preferably, the core amino acid sequence contacts an antigen and the one or more changes in the VFR increases the binding affinity of the polypeptide for the antigen. In some embodiments, the VFR comprises an amino acid sequence comprising a core sequence of $A_1$-$A_2$-$A_3$-$A_4$-$A_5$-$A_6$-$A_7$-$A_8$ (SEQ ID NO:10) wherein at least one of $A_1$ and/or $A_8$ is a hydrophobic amino acid or a cysteine. Preferably, the amino acid at position A is C, F, Y, W, M or L; the amino acid position at $A_2$ is D, N, or S; and/or the amino acid position at $A_8$ is M, C, F, V, or I. In other embodiments, the VFR comprises an amino acid sequence comprising a core sequence of $A_1$-$A_2$-$(A_3)_n$-$A_4$ (SEQ ID NO:11) wherein $A_1$ is C, F, or Y; $A_2$ is D, S or N; n is 5 to 15 contiguous amino acids and $A_3$ is an any amino acid; and $A_4$ is C or F. In some embodiments, the VFR amino acid positions correspond to amino acid positions 71-78 of a variable heavy chain domain. In some embodiments, the variable domain is a variable heavy chain domain.

The polypeptides of the invention may comprise an antibody variable domain, an antibody or antibody fragment. The antibody fragment may be a Fab, F(ab')$_2$, scFv, or Fv. In an embodiment, the polypeptide is a variable domain of a camelid monobody. In another embodiment, the polypeptide is an antibody variable heavy chain domain, monobody, or fragment thereof. Preferably the antibody variable domain is of the Vh3 subgroup. The polypeptides of the invention may also comprise fusion polypeptides. The polypeptide may be fused to at least a portion of a viral coat protein. In some embodiments, the viral coat protein is p111, pv111, Soc, Hoc, 9pD, pV1, or variants thereof.

Another aspect of the invention provides antibody variable domains containing a variant VFR and/or one or more variant CDRs. In some embodiments, the variant CDR1 comprises a N terminal portion that has at least one structural amino acid position having a variant amino acid, wherein the variant amino acid is an amino acid found at that position in a randomly generated CDR1 population at a frequency of at least one standard deviation above the average frequency for any amino acid at that position; a central portion that comprises at least one nonstructural position having a variant amino acid; and a C-terminal portion that comprises at least one structural amino acid position, wherein said structural amino acid position has a variant amino acid, wherein the variant amino acid is an amino acid found at that position in a randomly generated CDR1 population at a frequency of at least one standard deviation above the average frequency for any amino acid at that position, and the amino acid positions in the CDR1 region form a loop of the antigen binding pocket. In some embodiments, the N terminal amino acid position corresponding to position 24 of the heavy chain is a structural amino acid and the C terminal amino acid at a position corresponding to position 34 is a structural amino acid in a variable heavy chain. Preferably, the structural amino acid position is substituted with one or more hydrophobic amino acids encoded by a nonrandom codon set. The central portion can accommodate a contiguous sequence of up to 20 amino acids, preferably no more than 20 amino acids. In some embodiments, the contiguous sequence has about 9 to 15 amino acids that can be randomly varied if desired.

The N and/or C terminal structural amino acid positions can be substituted with up to six different amino acids so have a variant amino acid at those positions. The variant amino acid comprises or is an amino acid selected from the group consisting of up to 6 different amino acids, preferably, no more than six different amino acids, more preferably about 1 to 5 different amino acids, more preferably about 1 to 4 different amino acids, more preferably about 1 to 3 different amino acids, and most preferably about 1 to 2 different amino acids.

In some embodiments, variant CDR2 comprises a N terminal portion that comprises at least one position having a variant amino acid, wherein the variant amino acid is an amino acid found at that position in a randomly generated CDR2 population at a frequency of at least one standard deviation above the average frequency for any amino acid at that position; a central portion that comprises at least one nonstructural position having a variant amino acid, and the amino acid positions of the CDR2 form a loop of the antigen binding pocket. In some embodiments, the N terminal amino acid position corresponding to position 51 of the heavy chain is a structural amino acid. In some embodiments, the central position corresponds to amino acid residues 52 to 56. In some embodiments, the structural amino acid position can be substituted with up to six different amino acids, preferably no more than six different amino acids, about 1 to 6 different amino acids, more preferably about 1 to 5 different amino acids, more preferably about 1 to 4 different amino acids, more preferably about 1 to 3 different amino acids, and most preferably about 1-2 different amino acids. Preferably, the variant amino acid in the structural amino acid position is selected from the group consisting of hydrophobic amino acids and is encoded by a nonrandom codon set. The central portion can accommodate a contiguous sequence of up to 20 amino acids, preferably no more than 20 amino acids. In some embodiments, the central position has a contiguous sequence of about 5 to 15 amino acids that can be randomly varied if desired.

In some embodiments, a variant CDR3 comprises a N terminal portion that comprises at least one structural amino acid position having a variant amino acid, wherein the variant amino acid is an amino acid found at that position in a randomly generated CDR3 population at a frequency of at least one standard deviation above the average frequency for any amino acid at that position; a central portion that comprises at least one nonstructural position having a variant amino acid; and a C-terminal portion that comprises at least one structural amino acid position having a variant amino acid, wherein the variant amino acid is an amino acid found at that position in a randomly generated CDR3 population at a frequency of at least one standard deviation above the average frequency for any amino acid at that position, and the amino acid positions in the CDR3 region form a loop of the antigen binding pocket. In some embodiments, the N terminal amino acid positions corresponding to position 96 and 97 of the heavy chain are structural amino acids and the C terminal amino acids at positions corresponding to position 100i and 100j are structural amino acids. In some embodiments, the central position corresponds to amino acid positions 98 to 100h. In some embodiments, the structural amino acid positions are substituted with up to about 6 different amino acids, preferably no more than six different amino acids, more preferably about 1 to 5 different amino acids, more preferably about 1 to 4 different amino acids, more preferably 1 to 3 different amino acids, and most preferably 1-2 different amino acids. The central portion can accommodate a contiguous sequence of amino acids of up to 20 amino acids, and preferably, no more than 20 amino acids. In some embodiments, the central portion has a contiguous amino acid sequence of about 9 to 15 amino acids that can be randomly varied, if desired.

The invention also provides polynucleotides encoding the polypeptides and antigen binding domains of the invention, replicable expression vectors containing the polynucleotides, and host cells containing the vectors. In an embodiment, a plurality of the vectors encodes a library of a plurality of polypeptides or antigen binding domains of the invention. In a further embodiment, a virus displays on its surface the plurality of polypeptides or antigen binding domains encoded by the vectors.

Another aspect of the invention includes methods of generating a plurality of polypeptides that have variant VFRs. A method comprises generating a plurality of antibody variable domains, each antibody variable domain comprising a variant VFR, said method comprising: a) replacing an amino acid in at least one structural amino acid position at the N terminus of the VFR with up to six different amino acids; b) replacing an amino acid in at least one nonstructural amino acid position with any of the naturally occurring amino acids, wherein the nonstructural amino acids comprise about 1 to 20 contiguous amino acids; and c) replacing an amino acid position in at least one structural amino acid position at the C terminus of the VFR with up to six different amino acids. In some embodiments, the amino acid in at least one structural position is varied by using a nonrandom codon set that encodes up to six different amino acids, preferably encoding cysteine and/or one or more hydrophobic amino acids.

Another aspect of the invention includes methods of generating a plurality of polypeptides with variant VFR. In an embodiment, the method includes identifying VFR amino acid positions as those FR amino acid positions that form a loop of an antigen binding pocket or contribute to antigen binding; identifying at least one structural amino acid position in VFR and/or replacing the amino acid at said at least one structural amino acid position with a variant amino acid found at that position in a population of polypeptides with randomized VFR at a frequency at least one standard deviation above the average frequency for any amino acid at that position; and replacing at least one nonstructural amino acid position with a variant amino acid, wherein the variant amino acid is any of the naturally occurring amino acids or is encoded by a nonrandom codon set. In an embodiment, the polypeptide is a variable domain of a camelid monobody.

In some embodiments, identifying at least one structural amino acid position may optionally include generating a population of variant VFR regions from a source VFR by replacing each amino acid position in the VFR with a scanning amino acid; and identifying a structural amino acid position in the VFR as an amino acid position that when substituted with a scanning amino acid, the substituted polypeptide has a decrease in binding with a target molecule as compared to the parent VFR, wherein the target molecule specifically binds to a folded polypeptide and does not bind to unfolded polypeptide.

In another embodiment, the method of generating a population of polypeptides with variant VFR includes identifying VFR amino acid positions as those FR amino acid position that form a loop of an antigen binding pocket or contribute to antigen binding pocket; identifying at least one structural amino acid position and at least one nonstructural amino acid position in the loop; and/or generating a population of polypeptides with a variant VFR region by replacing the amino acid at the at least one structural amino acid position with about 1 to 6 of the most commonly occurring amino acids at that position in a population of polypeptides with randomized VFR; and replacing at least one nonstructural amino acid position with a variant amino acid, wherein the variant amino acid comprises any one of the naturally occurring amino acids or is encoded by a nonrandom codon set to generate a population of polypeptides that have different amino acid sequences in VFR. Preferably, the nonstructural amino acid positions comprise about 5 to 15 contiguous amino acids. Preferably, the VFR is well folded and stable for phage display.

In some embodiments, the method may optionally include steps for generating polypeptides with variant CDR1. The method includes identifying CDR1 amino acid positions that form a loop of an antigen binding pocket; identifying at least the structural amino acid position and at least one nonstructural amino acid position; and/or generating a population of polypeptides with a variant CDR1 region by replacing the amino acid at the at least one structural amino acid position with about 1 to 6 of the most commonly occurring amino acids at that position in a randomly generated population and replacing the nonstructural amino acid position with any of the naturally occurring amino acids or with a set of amino acids encoded by a nonrandom codon set to generate a population of polypeptides with different amino acid sequences in CDR1.

In some embodiments, the method may optionally include steps for generating polypeptides with variant CDR2. The method includes identifying CDR2 amino acid positions that form a loop of an antigen binding pocket; identifying at least the structural amino acid position and at least one nonstructural amino acid position; and/or generating a population of polypeptides with a variant CDR2 region by replacing the amino acid at the at least one structural amino acid position with about 1 to 6 of the most commonly occurring amino acids at that position in a randomly generated population and/or replacing the nonstructural amino acid position with any of the naturally occurring amino acids or with a set of amino acids encoded by a nonrandom codon set to generate a population of polypeptides with different amino acid sequences in CDR2.

In some embodiments, the method may optionally include steps for generating polypeptides with variant CDR3. The method includes identifying CDR3 amino acid positions that form a loop of an antigen binding pocket; identifying at least the structural amino acid position and at least one nonstructural amino acid position; and/or generating a population of polypeptides with a variant CDR3 region by replacing the amino acid at the at least one structural amino acid position with about 1 to 6 of the most commonly occurring amino acids at that position in a randomly generated population and replacing the nonstructural amino acid position with any of the naturally occurring amino acids or with a set of amino acids encoded by a nonrandom codon set to generate a population of polypeptides with different amino acid sequences in CDR3.

The invention also provides a method for designing a VFR scaffold. The method includes identifying amino acid positions in a FR that form a loop of an antigen binding pocket or that contribute to antigen binding to identify VFR amino acid positions; generating a library of polypeptides with variant VFR regions; selecting members of the library that bind to a target molecule that binds to folded polypeptide and does not bind to unfolded polypeptide; analyzing the binders to identify structural amino acid positions in the VFR; and selecting as a scaffold, a binder that has a structural amino acid position at the N and/or C-termini of the VFR and not in a central position of the VFR. In an embodiment, the identified structural amino acids positions include the first N-terminal amino acid, second N-terminal amino acid, and/or the C-terminal amino acid.

In some embodiments, the method also includes identifying an amino acid that can be substituted at the structural amino acid position, wherein the amino acid is selected from the group of amino acids that occur at that position more frequently than randomly expected; and forming a scaffold with at least one identified amino acid in at least one structural amino acid position. Preferably, the amino acids substituted at the structural amino acid position are hydrophobic amino acids or are cysteines and are encoded by a nonrandom codon set.

The invention also provides for polypeptides and antigen variable domains and compositions thereof prepared according to the methods of the invention, polynucleotides encoding the polypeptides and antigen variable domains prepared according to the methods of the invention, replicable expression vectors containing the polynucleotides, and host cells containing the vectors. In an embodiment, a plurality of the vectors encodes a library of a plurality of polypeptides or antigen binding domains of the invention. In a further embodiment, a virus displays on its surface the plurality of polypeptides or antigen binding domains encoded by the vectors. The methods of the invention are useful for identifying novel polypeptides, antibody, antibody fragments, and antibody variable domains that may be used therapeutically or as reagents.

BRIEF DESCRIPTION OF THE FIGURES

FIG. 4 shows the structure-based database of V.sub.HH domain diversity. The percentage occurrence of each amino acid type at each position in CDRs 1, 2, 3 and FR3(71-78) (top to bottom) was calculated after normalization for codon bias. The amino acids are listed in order of increasing hydrophobicity, from left to right. The data were used to determine Shannon entropy values, which were compared to the Shannon entropies for human/mouse V.sub.H domains and llama V.sub.HH domains. At each position, the most abundant residue types that together account for 50% of the sequences in the structure-based database are colored dark gray. The most abundant residue types that account for 50% of the sequences within the human/mouse database are colored medium gray. Light gray indicates residue types that are common in both the structure-based and human/mouse databases. The distributions were determined from the sequences of the following number of unique clones: CDR1, 252; CDR2, 247; FR3(71-78), 211; CDR3, 148.

DETAILED DESCRIPTION OF THE INVENTION

A. Definitions

Figure 1A:
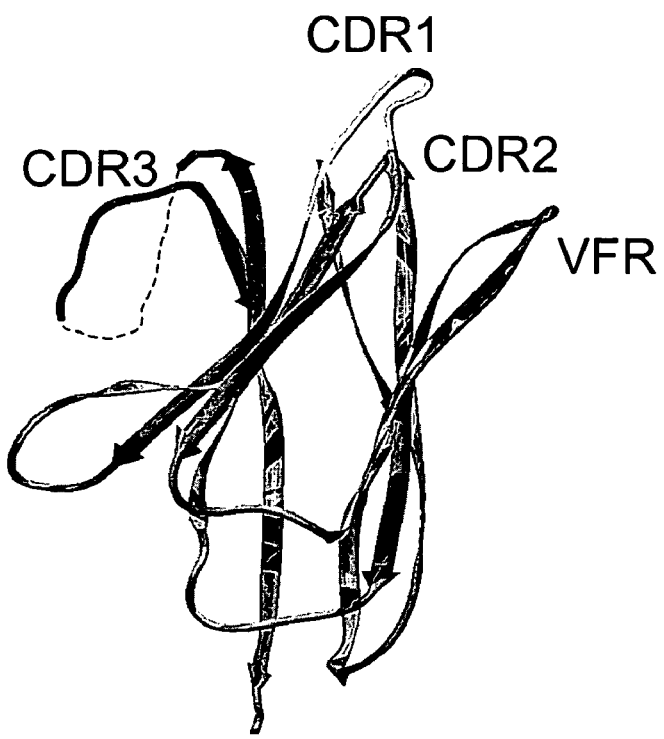
FIGS. 1A and 1B show the three-dimensional structure of the VHH domain of the VHH-RIG construct. The four loops chosen for study are: CDRH1, CDRH2, CDRH3, and VFR. The domain is shown in a ribbon representation viewed from the side (FIG. 1A) or looking down on the combining site (FIG. 1B). The figure was derived from X-ray coordinates (PDB entry 1 SHM) and was rendered with the computer program Swiss PDB Viewer. The dotted line represents a portion of CDRH3 for which there was no observable electron density.

The numbering of all antibody variable domains herein is the numbering system according to Kabat as published in Sequences of Proteins of Immunological Interest, 5th edition, NIH, 1991.

The term "antibody" is used in the broadest sense and specifically covers single monoclonal antibodies (including agonist and antagonist antibodies), antibody compositions with polyepitopic specificity, affinity matured antibodies, humanized antibodies, chimeric antibodies, single chain antigen binding molecules such as monobodies, as well as antigen binding fragments or polypeptides (e.g., Fab, F(ab')$_2$, scFv and Fv), so long as they exhibit the desired biological activity.

As used herein, "antibody variable domain" refers to the portions of the light and heavy chains of antibody molecules that include amino acid sequences of Complementary Determining Regions (CDRs; ie., CDR1, CDR2, and CDR3), and Framework Regions (FRs; i.e. FR1, FR2, FR3, and FR4). FR include those amino acid positions in an antibody variable domain other than CDR positions as defined herein. VH refers to the variable domain of the heavy chain. VL refers to the variable domain of the light chain. VHH refers to the heavy chain variable domain of a monobody. CDRH and FRH, for example, refer to a CDR and FR, respectively, from a variable domain of a heavy chain or the heavy chain variable domain of a monobody.

As used herein "CDR" refers to a contiguous sequence of amino acids that form an antigen binding pocket or groove and that may contact antigen. In an embodiment, the amino acids of a CDR are determined by inspection of the three-dimensional structure of an antibody, antibody heavy chain variable domain, or antibody light chain variable domain. The three-dimensional structure may be analyzed for solvent accessible amino acid positions as such positions are likely to form a loop in an antibody variable domain. The three dimensional structure of the antibody variable domain may be derived from a crystal structure or protein modeling. In another embodiment, the boundaries of the CDR are determined according to Chothia (Chothia and Lesk, 1987, *J. Mol. Biol.*, 196:901-917). One to three amino acid residues may optionally be added to the C-terminal and N-terminal ends of the Chothia CDRs. In other embodiments, the CDRs may be that as described by Kabat (cited supra). In some embodiments, the amino acid positions of CDR1 comprise, consists essentially of or consist of amino acid positions 24 to 34, the amino acid positions of CDR2 comprise, consists essentially of or consist of amino acid positions 51 to 56 and the CDR3 positions comprise, consists essentially of or consist of amino acid positions 96 to 101 of an antibody or monobody heavy chain variable domain.

"Antibody fragments" comprise only a portion of an intact antibody, generally including an antigen binding site of the intact antibody and thus retaining the ability to bind antigen. Nonlimiting examples of antibody fragments encompassed by the present definition include: (i) the Fab fragment, having VL, CL, VH and CH1 domains having one interchain disulfide bond between the heavy and light chain; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment which consists of a VH domain; (vii) hingeless antibodies including at least VL, VH, CL, CH1 domains and lacking hinge region; (viii) F(ab')$_2$ fragments, a bivalent fragment including two Fab' fragments linked by a disulfide bridge at the hinge region; (ix) single chain antibody molecules (e.g. single chain Fv; scFv); (x) "diabodies" with two antigen binding sites, comprising a heavy chain variable domain (VH) connected to a light chain variable domain (VL) in the same polypeptide chain; (xi) single arm antigen binding molecules comprising a light chain, a heavy chain and a N-terminally truncated heavy chain constant region sufficient to form a Fc region capable of increasing the half life of the single arm antigen binding domain; (xii) "linear antibodies" comprising a pair of tandem Fd segments (VH-CH1-VH-CH1) which, together with complementary light chain polypeptides, form a pair of antigen binding regions.

As used herein, "codon set" refers to a set of different nucleotide triplet sequences used to encode desired variant amino acids. A set of oligonucleotides can be synthesized, for example, by solid phase synthesis, containing sequences that represent all possible combinations of nucleotide triplets provided by the codon set and that will encode the desired group of amino acids. A standard form of codon designation is that of the IUB code, which is known in the art and described herein. A "non-random codon set", as used herein, thus refers to a codon set that encodes select amino acids that fulfill partially, preferably completely, the criteria for amino acid selection as described herein. Examples of non random codon sets are known to those of skill in the art. Synthesis of oligonucleotides with selected nucleotide "degeneracy" at certain positions is well known in that art, for example the TRIM approach (Knappek et al.; J. Mol. Biol. (1999), 296:57-86); Garrard & Henner, Gene (1993), 128:103). Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can, but does not necessarily, include restriction enzyme sites useful for, for example, cloning purposes.

As used herein, "variable framework region" or "VFR" refers to framework residues that form a part of the antigen binding pocket or groove and/or that may contact antigen. In some embodiments, the framework residues form a loop that is a part of the antigen binding pocket or groove. The amino acid residues in the loop may or may not contact the antigen. In an embodiment, the loop amino acids of a VFR are determined by inspection of the three-dimensional structure of an antibody, antibody heavy chain, or antibody light chain. The three-dimensional structure may be analyzed for solvent accessible amino acid positions as such positions are likely to form a loop and/or provide antigen contact in an antibody variable domain. Some of the solvent accessible positions can tolerate amino acid sequence diversity and others (eg structural positions) will be less diversified. The three dimensional structure of the antibody variable domain may be derived from a crystal structure or protein modeling. In some embodiments, the VFR comprises, consists essentially of, or consists of amino acid positions corresponding to amino acid positions 71 to 78 of the heavy chain variable domain, the positions defined according to Kabat et al., 1991. In some embodiments, VFR forms a portion of Framework Region 3 located between CDRH2 and CDRH3. Preferably, VFR forms a loop that is well positioned to make contact with a target antigen or form a part of the antigen binding pocket.

The term "monoclonal antibody" as used herein refers to an antibody obtained from a population of substantially homogeneous antibodies, i.e., the individual antibodies comprising the population are essentially identical except for variants that may arise during production of the antibody.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region (HVR) of the recipient are replaced by residues from a hypervariable region (HVR) of a non-human species (donor antibody) such as mouse, rat, rabbit or nonhuman primate having the desired specificity, affinity, and capacity. In some instances, framework region (FR) residues of the human immunoglobulin are replaced by corresponding non-human residues to improve antigen binding affinity. Furthermore, humanized antibodies may comprise residues that are not found in the recipient antibody or the donor antibody. These modifications may be made to improve antibody affinity or functional activity. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. Humanized antibodies can also be produced as antigen binding fragments as described herein. The humanized antibody optionally will also comprise at least a portion of an immunoglobulin constant region (Fc), typically that of or derived from a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma &*

Immunol. 1:105-115 (1998); Harris, Biochem. Soc. Transactions 23:1035-1038 (1995); Hurle and Gross, Curr. Op. Biotech 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues.

The term "monobody" as used herein, refers to an antigen binding molecule with a heavy chain variable domain and no light chain variable domain. A monobody can bind to an antigen in the absence of light chains and typically has three CDR regions designated CDRH1, CDRH2 and CDRH3. A heavy chain IgG monobody has two heavy chain antigen binding molecules connected by a disulfide bond. The heavy chain variable domain comprises one or more CDR regions, preferably a CDRH3 region. A "$V_hH$" or "VHH" refers to a variable domain of a heavy chain antibody such as a monobody. A "camelid monobody" or "camelid VHH" refers to a monobody or antigen binding portion thereof obtained from a source animal of the camelid family, including animals with feet with two toes and leathery soles. Animals in the camelid family include camels, llamas, and alpacas. In an embodiment, the monobody is a llama anti-HCG monobody variable heavy chain. Table 1 shows the nucleotide sequence (SEQ ID NO:1) of the llama anti-HCG monobody variable heavy chain domain. Table 2 shows the amino acid sequence (SEQ ID NO:2) of the llama anti-HCG monobody variable heavy chain domain.

precisely identical in DNA content, due to deliberate or inadvertent mutations. Mutant progeny that have the same function or biological activity as screened for in the originally transformed cell are included. Where distinct designations are intended, it will be clear from the context.

"Control sequences" when referring to expression means DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

The term "coat protein" means a protein, at least a portion of which is present on the surface of the virus particle. From a functional perspective, a coat protein is any protein, which associates with a virus particle during the viral assembly process in a host cell, and remains associated with the assembled virus until it infects another host cell. The coat protein may be the major coat protein or may be a minor coat protein. A "major" coat protein is generally a coat protein which is present in the viral coat at preferably at least about 5, more preferably at least about 7, even more preferably at least about 10 copies of the protein or more. A major coat protein may be present in tens, hundreds or even thousands of copies per virion. An example of a major coat protein is the p8 protein of filamentous phage.

A "fusion protein" and a "fusion polypeptide" refer to a polypeptide having two portions covalently linked together,

TABLE 1

```
GAT GTT CAG TTG CAG GAA TCA GGC GGT GGC TTG GTA CAG GCC GGA  45

GGT TCG TTG CGT TTG TCC TGT GCT GCC TCG GGT CGT ACT GGT TCT  90

ACT TAT GAT ATG GGC TGG TTT CGT CAG GCT CCG GGT AAA GAA CGT 135

GAA TCG GTT GCC GCC ATT AAC TGG GAT TCG GCT CGT ACT TAC TAT 180

GCT TCG TCC GTC CGT GGT CGT TTT ACT ATT TCA CGT GAT AAT GCC 225

AAA AAA ACT GTC TAT TTG CAG ATG AAT TCA TTG AAA CCA GAA GAT 270

ACT GCC GTC TAT ACT TGT GGT GCT GGT GAA GGC GGT ACT TGG GAT 315

TCT TGG GGT CAG GGT ACC CAG GTC ACT GTC TCC TCT GCC GGT GGT 360

ATG GAT TAT AAA GAT GAT GAT GAT AAA TGA                     390
```

TABLE 2

```
DVQLQ ESGGG LVQAG GSLRL SCAAS GRTGS TYDMG WFRQA PGKER ESVAA
    5    10    15    20    25    30    35    40    45    50

INWDS ARTYY ASSVR GRFTI SRDNA KKTVY LQMNS LKPED TAVYT CGAGE
   54    59    64    69    74    79   82b    86    91    96
  52a                                  82 82c

GGTWD SWGQG TQVTV SSAGG MDYKD DDDK
  101   106   111   116   121  126
```

"Cell", "cell line", and "cell culture" are used interchangeably herein and such designations include all progeny of a cell or cell line. Thus, for example, terms like "transformants" and "transformed cells" include the primary subject cell and cultures derived therefrom without regard for the number of transfers. It is also understood that all progeny may not be where each of the portions is a polypeptide having a different property. The property may be a biological property, such as activity in vitro or in vivo. The property may also be a simple chemical or physical property, such as binding to a target molecule, catalysis of a reaction, etc. The two portions may be linked directly by a single peptide bond or through a peptide linker containing one or more amino acid residues. Generally, the two portions and the linker will be in reading frame with each other.

"Heterologous DNA" is any DNA that is introduced into a host cell. The DNA may be derived from a variety of sources including genomic DNA, cDNA, synthetic DNA and fusions or combinations of these. The DNA may include DNA from the same cell or cell type as the host or recipient cell or DNA from a different cell type, for example, from a mammal or plant. The DNA may, optionally, include marker or selection genes, for example, antibiotic resistance genes, temperature resistance genes, etc.

As used herein, "library" refers to a plurality of antibody, antibody fragment sequences, or antibody variable domains (for example, polypeptides of the invention), or the nucleic acids that encode these sequences, the sequences being different in the combination of variant amino acids that are introduced into these sequences according to the methods of the invention.

"Ligation" is the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation or by silica purification. The DNA fragments that are to be ligated together are put in solution in about equimolar amounts. The solution will also contain ATP, ligase buffer, and a ligase such as T4 DNA ligase at about 10 units per 0.5 µg of DNA. If the DNA is to be ligated into a vector, the vector is first linearized by digestion with the appropriate restriction endonuclease(s). The linearized fragment is then treated with bacterial alkaline phosphatase or calf intestinal phosphatase to prevent self-ligation during the ligation step.

A "mutation" is a deletion, insertion, or substitution of a nucleotide(s) relative to a reference nucleotide sequence, such as a wild type sequence.

As used herein, "natural" or "naturally occurring" antibodies or antibody variable domains, refers to antibodies or antibody variable domains having a sequence of an antibody or antibody variable domain identified from a nonsynthetic source, for example, from a differentiated antigen-specific B cell obtained ex vivo, or its corresponding hybridoma cell line, or from the serum of an animal. These antibodies can include antibodies generated in any type of immune response, either natural or otherwise induced. Natural antibodies include the amino acid sequences, and the nucleotide sequences that constitute or encode these antibodies, for example, as identified in the Kabat database. As used herein, natural antibodies are different than "synthetic antibodies", synthetic antibodies referring to antibody sequences that have been changed, for example, by the replacement, deletion, or addition, of an amino acid, or more than one amino acid, at a certain position with a different amino acid, the different amino acid providing an antibody sequence different from the source antibody sequence.

"Operably linked" when referring to nucleic acids means that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contingent and in reading frame. However, enhancers do not have to be contiguous. Linking is accomplished by ligation at convenient restriction sites. If such sites do not exist, the synthetic oligonucleotide adapters or linkers are used in accord with conventional practice.

"Phage display" is a technique by which variant polypeptides are displayed as fusion proteins to at least a portion of a coat protein on the surface of phage, e.g., filamentous phage, particles. A utility of phage display lies in the fact that large libraries of randomized protein variants can be rapidly and efficiently sorted for those sequences that bind to a target molecule with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman, *Curr. Opin. Struct. Biol.*, 3:355-362 (1992), and references cited therein. In monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells, *Methods: A companion to Methods in Enzymology*, 3:205-0216 (1991).

A "phagemid" is a plasmid vector having a bacterial origin of replication, e.g., Co1E1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids, which contain a phage coat protein gene or fragment thereof linked to a heterologous polypeptide gene as a gene fusion such that the heterologous polypeptide is displayed on the surface of the phage particle.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

"Oligonucleotides" are short-length, single- or double-stranded polydeoxynucleotides that are prepared by known methods such as chemical synthesis (e.g. phosphotriester, phosphite, or phosphoramidite chemistry, using solid-phase techniques such as described in EP 266,032 published 4 May 1988, or via deoxynucloside H-phosphonate intermediates as described by Froeshler et al., *Nucl. Acids, Res.*, 14:5399-5407

(1986)). Further methods include the polymerase chain reaction defined below and other autoprimer methods and oligonucleotide syntheses on solid supports. All of these methods are described in Engels et al., *Agnew. Chem. Int. Ed. Engl.*, 28:716-734 (1989). These methods are used if the entire nucleic acid sequence of the gene is known, or the sequence of the nucleic acid complementary to the coding strand is available. Alternatively, if the target amino acid sequence is known, one may infer potential nucleic acid sequences using known and preferred coding residues for each amino acid residue. The oligonucleotides can be purified on polyacrylamide gels or molecular sizing columns or by precipitation.

DNA is "purified" when the DNA is separated from non-nucleic acid impurities. The impurities may be polar, non-polar, ionic, etc.

A "scaffold", as used herein, refers to a polypeptide or portion thereof that maintains a stable structure or structural element when a heterologous polypeptide is inserted into the polypeptide. The scaffold provides for maintenance of a structural and/or functional feature of the polypeptide after the heterologous polypeptide has been inserted. In one embodiment, a VFR scaffold comprises a N-terminal portion having a cysteine residue and a C terminal portion having a cysteine residue, wherein the cysteine residues in the N terminal and C-terminal portion of the VFR form a disulfide bond that stabilizes the central portion insert that can vary in sequence and in length.

A "source antibody", as used herein, refers to an antibody or antigen binding polypeptide whose antigen binding determinant sequence serves as the template sequence upon which diversification according to the criteria described herein is performed. An antigen binding determinant sequence generally includes an antibody variable region, preferably at least one CDR, and preferably including at least one framework regions. A source antibody variable domain can include an antibody, antibody variable domain, antigen binding fragment or polypeptide thereof, a monobody, VHH, a monobody or antibody variable domain obtained from a naïve or synthetic library, camelid antibodies, naturally occurring antibody or monobody, synthetic antibody or monobody, recombinant antibody or monobody, humanized antibody or monobody, germline derived antibody or monobody, chimeric antibody or monobody, and affinity matured antibody or monobody. In one embodiment, the polypeptide is an antibody variable domain that is a member of the Vh3 subgroup and preferably, is a camelid monobody. In another embodiment, the antibody is a llama anti-HCG monobody.

As used herein, "solvent accessible position" refers to a position of an amino acid residue in the variable region of a heavy and/or light chain of a source antibody or antigen binding polypeptide that is determined, based on structure, ensemble of structures and/or modeled structure of the antibody or antigen binding polypeptide, as potentially available for solvent access and/or contact with a molecule, such as an antibody-specific antigen. These positions are typically found in the CDRs, but can also be found in FR and on the exterior of the protein. The solvent accessible positions of an antibody or antigen binding polypeptide, as defined herein, can be determined using any of a number of algorithms known in the art. Preferably, solvent accessible positions are determined using coordinates from a 3-dimensional model of an antibody or antigen binding polypeptide, preferably using a computer program such as the InsightII program (Accelrys, San Diego, Calif.). Solvent accessible positions can also be determined using algorithms known in the art (e.g., Lee and Richards, J. Mol. Biol. 55, 379 (1971) and Connolly, J. Appl. Cryst. 16, 548 (1983)). Determination of solvent accessible positions can be performed using software suitable for protein modeling and 3-dimensional structural information obtained from an antibody. Software that can be utilized for these purposes includes SYBYL Biopolymer Module software (Tripos Associates). Generally and preferably, where an algorithm (program) requires a user input size parameter, the "size" of a probe which is used in the calculation is set at about 1.4 Angstrom or smaller in radius. In addition, determination of solvent accessible regions and area methods using software for personal computers has been described by Pacios ((1994) "ARVOMOL/CONTOUR: molecular surface areas and volumes on Personal Computers." *Comput. Chem.* 18(4): 377-386; and (1995). "Variations of Surface Areas and Volumes in Distinct Molecular Surfaces of Biomolecules." *J. Mol. Model.* 1: 46-53.)

The phrase "structural amino acid position" as used herein refers to an amino acid of a polypeptide that contributes to the stability of the structure of the polypeptide such that the polypeptide retains at least one biological function such as specifically binding to a molecule such as an antigen and/or binds to a target molecule that binds to folded polypeptide and does not bind to unfolded polypeptide such as Protein A. Structural amino acid positions are identified as amino acid positions less tolerant to amino acid substitutions without affecting the structural stability of the polypeptide. Amino acid positions less tolerant to amino acid substitutions can be identified using a method such as alanine scanning mutagenesis or shotgun scanning as described in WO 01/44463 and analyzing the effect of loss of the wild type amino acid on structural stability. If a wild type amino acid is replaced with a scanning amino acid in a position, and the resulting variant exhibits poor binding to a target molecule that binds to folded polypeptide, then that position is important to maintaining the structure of the polypeptide. A structural amino acid position is a position in which, preferably, the ratio of polypeptides with wild type amino acid at a position to a variant substituted with a scanning amino acid at that position is at least about 3 to 1, about 5 to 1, about 8 to 1, about 10 to 1 or greater. In a further embodiment, structural amino acid positions are positions that have a weighted hydrophobicity value of greater than −0.5 as determined using the method of Kyte and Doolittle (cited supra) when the population is randomized in the VFR or CDRs. For example, in one embodiment the boundaries of CDR1 in the heavy chain are selected at amino acids 24 and 34 as these positions show a strong preference for hydrophobes.

The term "stability" as used herein refers to the ability of a molecule to maintain a folded state under physiological conditions such that it retains at least one of its normal functional activities, for example, binding to an antigen or to a molecule like Protein A. The stability of the molecule can be determined using standard methods. For example, the stability of a molecule can be determined by measuring the thermal melt ("TM") temperature. The TM is the temperature in degrees Celsius at which ½ of the molecules become unfolded. Typically, the higher the TM, the more stable the molecule.

The phrase "randomly generated population" as used herein refers to a population of polypeptides wherein one or more amino acid positions in a domain has a variant amino acid encoded by a random codon set which allows for substitution of all 20 naturally occurring amino acids at that position. For example, in one embodiment, a randomly generated population of polypeptides having randomized VFR or portions thereof include a variant amino acid at each position in VFR that is encoded by a random codon set. A random codon set includes but is not limited to codon sets designated NNS and NNK.

A "transcription regulatory element" will contain one or more of the following components: an enhancer element, a promoter, an operator sequence, a repressor gene, and a transcription termination sequence. These components are well known in the art, e.g., U.S. Pat. No. 5,667,780.

A "transformant" is a cell that has taken up and maintained DNA as evidenced by the expression of a phenotype associated with the DNA (e.g., antibiotic resistance conferred by a protein encoded by the DNA).

"Transformation" means a process whereby a cell takes up DNA and becomes a "transformant". The DNA uptake may be permanent or transient.

A "variant" or "mutant" of a starting or reference polypeptide (for e.g., a source antibody or its variable domain(s)), such as a fusion protein (polypeptide) or a heterologous polypeptide (heterologous to a phage), is a polypeptide that 1) has an amino acid sequence different from that of the starting or reference polypeptide and 2) was derived from the starting or reference polypeptide through either natural or artificial (manmade) mutagenesis. Such variants include, for example, deletions from, and/or insertions into and/or substitutions of, residues within the amino acid sequence of the polypeptide of interest. For example, a fusion polypeptide of the invention generated using an oligonucleotide comprising a nonrandom codon set that encodes a sequence with a variant amino acid (with respect to the amino acid found at the corresponding position in a source antibody/antigen binding fragment or polypeptide) would be a variant polypeptide with respect to a source antibody or antigen binding fragment or polypeptide. Thus, a variant VFR refers to a VFR comprising a variant sequence with respect to a starting or reference polypeptide sequence (such as that of a source antibody or antigen binding fragment or polypeptide). A variant amino acid, in this context, refers to an amino acid different from the amino acid at the corresponding position in a starting or reference polypeptide sequence (such as that of a source antibody or antigen binding fragment or polypeptide). A variant amino acid can be an amino acid selected from a group of amino acids that fulfill the criteria for substitution at a position. For example, a structural amino acid position can be substituted with up to six different amino acids, and the variant amino acid can be selected from the group consisting of the six different amino acids. Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites. Methods for generating amino acid sequence variants of polypeptides are described in U.S. Pat. No. 5,534,615, expressly incorporated herein by reference.

A "wild type" or "reference" sequence or the sequence of a "wild type" or "reference" protein/polypeptide, such as a coat protein, or a CDR or variable domain of a source antibody, is the reference sequence from which variant polypeptides are derived through the introduction of mutations. In general, the "wild type" sequence for a given protein is the sequence that is most common in nature. Similarly, a "wild type" gene sequence is the sequence for that gene which is most commonly found in nature. Mutations may be introduced into a "wild type" gene (and thus the protein it encodes) either through natural processes or through man induced means. The products of such processes are "variant" or "mutant" forms of the original "wild type" protein or gene.

As used herein "Vh3" refers to a subgroup of antibody variable domains. The sequences of known antibody variable domains have been analyzed for sequence identity and divided into groups. Antibody heavy chain variable domains in subgroup III are known to have a Protein A binding site.

A "plurality" or "population" of a substance, such as a polypeptide or polynucleotide of the invention, as used herein, generally refers to a collection of two or more types or kinds of the substance. There are two or more types or kinds of a substance if two or more of the substances differ from each other with respect to a particular characteristic, such as the variant amino acid found at a particular amino acid position. For example, there is a plurality or population of polypeptides of the invention if there are two or more polypeptides of the invention that are substantially the same, preferably identical, in sequence except for the sequence of a variant VFR or except for the variant amino acid at a particular solvent accessible amino acid position. In another example, there is a plurality or population of polynucleotides of the invention if there are two or more polynucleotides of the invention that are substantially the same, preferably identical, in sequence except for the sequence that encodes a variant VFR or except for the sequence that encodes a variant amino acid for a particular solvent accessible acid position or structural amino acid position.

B. Modes of the Invention

A diverse library of antibody variable domains is useful to identify novel antigen binding molecules having high affinity. Generating a library with antibody variable domains with a high level of diversity and that are structurally stable allows for the isolation of high affinity binders and for antibody variable domains that can more readily be produced in cell culture on a large scale. The present invention is based on the showing that regions of an antibody variable domain that form the antigen binding pocket have both structural and nonstructural amino acid positions. The structural amino acid positions should have limited diversity in order to maintain the stability of the antibody variable domains while nonstructural amino acid positions can be varied randomly, if desired.

In particular embodiments, heavy chain CDR1 can tolerate greater diversity than would be expected from naturally occurring sequences between amino acid positions 24 and 34 and forms a continuous hypervariable loop that is highly accessible for antigen contact. Amino acid positions corresponding to positions 24 and 34 should have more limited diversity as they are structural amino acid positions. In heavy chain CDR2, amino acid position corresponding to position 51 is a structural amino acid position, while positions 52-56 can tolerate diversity. Heavy chain CDRH3 can vary both in sequence and in loop length. The structural amino acid positions of CDRH3 are typically at the N and C terminal ends. In some embodiments, amino acid positions corresponding to amino acid positions 98 to 100h can be randomly varied. In some embodiments, a portion of the FR 3 region of the heavy chain also forms a loop that is part of the antigen binding pocket. This loop is designated a variable framework region (VFR) and comprises structural amino acid positions at the N and C terminal ends with a central portion that can be varied randomly. In some embodiments, amino acid positions corresponding to positions 71, 72, and 78 are structural, while amino acid positions corresponding to amino acids 73-77 can be varied randomly.

1. Generating Diversity in VFRs

High quality polypeptide libraries of antibody variable domains may be generated by diversifying a heavy chain variable framework domain (VFR), and optionally one or more CDRs, of a source antibody or antibody fragment. The polypeptide libraries comprise a plurality of variant polypeptides having at least one VFR. Preferably, the VFR and/or CDR is designed to provide for amino acid sequence diversity at certain positions while minimizing structural perturbations.

The diversity of the library or population of the antibody variable domains is designed to maximize diversity while minimizing structural perturbations of the antibody variable domain to provide for increased ability to isolate high affinity antibodies. The number of positions mutated in the antibody variable domain is minimized or specifically targeted. In some embodiments, structural amino acid positions are identified and diversity is minimized at those positions to ensure a well-folded polypeptide. Preferably, a single antibody or antigen binding polypeptide including at least one CDR, is used as the source polypeptide.

The source polypeptide may be any antibody, antibody fragment, or antibody variable domain whether naturally occurring or synthetic. A polypeptide or source antibody variable domain can include an antibody, antibody variable domain, antigen binding fragment or polypeptide thereof, a monobody, VHH, a monobody or antibody variable domain obtained from a naïve or synthetic library, camelid antibodies, naturally occurring antibody or monobody, synthetic antibody or monobody, recombinant antibody or monobody, humanized antibody or monobody, germline derived antibody or monobody, chimeric antibody or monobody, and affinity matured antibody or monobody. In one embodiment, the polypeptide is an antibody variable domain that is a member of the Vh3 subgroup and preferably, is a camelid monobody.

Source antibody variable domains include but are not limited to antibody variable domains previously used to generate phage display libraries, such as VHH-RIG, VHH-VLK, VHH-LLR, and VHH-RLV (Bond et al., 2003, *J. Mol. Biol.,* 332:643-655), and humanized antibodies or antibody fragments, such as mAbs 4D5, 2C4, and $A_{4.6.1}$. The sequences of many source antibody domains are know to those of skill in the art. For example, antibody variable domain sequences for antibody 4D5 can be found in U.S. Pat. No. 6,037,454 and for antibody 2C4 in U.S. Pat. No. 6,627,196. The amino sequence of monobody heavy chain variable domain can be found in Table 2 (SEQ ID NO:2). Table 3 shows the amino acid sequence of CDR3 in the source VHH-RIG, VHH-VLK, VHH-LLR, and VHH-RLV scaffolds. In an embodiment, the library is generated using the heavy chain variable domain (VHH) of a monobody. The small size and simplicity make monobodies attractive scaffolds for peptidomimetic and small molecule design, as reagents for high throughput protein analysis, or as potential therapeutic agents. The diversified VHH domains are useful, inter alia, in the design of enzyme inhibitors, novel antigen binding molecules, modular binding units in bispecific or intracellular antibodies, as binding reagents in protein arrays, and as scaffolds for presenting constrained peptide libraries.

One criterion for generating diversity in the polypeptide library is selecting amino acid positions that form an antigen binding pocket or groove in a single source antibody variable domain whether or not the residues actually contact the antigen. One way of determining whether the amino acid position is part of an antigen binding site is to examine the three dimensional structure of the antibody variable domain, for example, for solvent accessible positions. If such information is available, amino acid positions that are in proximity to the antigen can also be determined. Three dimensional structure information of antibody variable domains are available for many antibodies or can be prepared using available molecular modeling programs. Solvent accessible amino acid positions can be found in FR and CDRs, and typically form loops on the exterior of the protein. Preferably, solvent accessible positions are determined using coordinates from a 3-dimensional model of an antibody, using a computer program such as the InsightII program (Accelrys, San Diego, Calif.). Solvent accessible positions can also be determined using algorithms known in the art (e.g., Lee and Richards, J. Mol. Biol. 55, 379 (1971) and Connolly, J. Appl. Cryst. 16, 548 (1983)). Determination of solvent accessible positions can be performed using software suitable for protein modeling and 3-dimensional structural information obtained from an antibody. Software that can be utilized for these purposes includes SYBYL Biopolymer Module software (Tripos Associates). Generally and preferably, where an algorithm (program) requires a user input size parameter, the "size" of a probe which is used in the calculation is set at about 1.4 Angstrom or smaller in radius. In addition, determination of solvent accessible regions and area methods using software for personal computers has been described by Pacios ((1994) "ARVOMOL/CONTOUR: molecular surface areas and volumes on Personal Computers", *Comput. Chem.* 18(4): 377-386; and "Variations of Surface Areas and Volumes in Distinct Molecular Surfaces of Biomolecules." *J. Mol. Model.* (1995), 1: 46-53). The location of amino acid positions involved in forming antigen binding pockets may vary in different antibody variable domains, but typically involve at least one or a portion of a CDR and/or at least one or a portion of the FR region.

In some instances, selection of solvent accessible residues is further refined by choosing solvent accessible residues that collectively form a minimum contiguous patch when the reference polypeptide or source antibody is in its 3-D folded structure. A compact (minimum) contiguous patch may comprise a portion of the FR and only a subset (for example, 2-5 CDRs) of the full range of CDRs, for example, CDRH1/H2/H3/L3. Solvent accessible residues that do not contribute to formation of such a patch may optionally be excluded from diversification. Refinement of selection by this criterion permits the practitioner to minimize, as desired, the number of residues to be diversified. This selection criterion may also be used, where desired, to choose residues to be diversified that may not necessarily be deemed solvent accessible. For

TABLE 3

| VHH Scaffold | SEQ ID NO: | CDRH3 Position | | | | | | | | | | | | | | | | |
|---|---|---|---|---|---|---|---|---|---|---|---|---|---|---|---|---|---|---|
| | | 96 | 97 | 98 | 99 | 100 | 100a | 100b | 100c | 100d | 100e | 100f | 100g | 100h | 100i | 100j | 100k | 100l |
| RIG | 3 | R | I | G | R | S | V | F | N | L | R | R | E | S | W | V | T | W |
| LLR | 4 | L | L | R | R | G | V | N | A | T | P | N | W | F | G | L | V | G |
| VLK | 5 | V | L | K | R | R | G | S | S | V | A | I | F | T | R | V | Q | S |
| RLV | 6 | R | L | V | N | G | L | S | G | L | V | S | W | E | M | P | L | A | example, a residue that is not deemed solvent accessible, but forms a contiguous patch in the 3-D folded structure with other residues that are deemed solvent accessible may be selected for diversification. Selection of such residues would be evident to one skilled in the art, and its appropriateness can also be determined empirically and according to the needs and desires of the skilled practitioner.

VFR and CDR diversity may be limited at structural amino acid positions. A structural amino acid position refers to an amino acid position in a VFR or CDR of a polypeptide that contributes to the stability of the structure of the polypeptide such that the polypeptide retains at least one biological function such as specifically binding to a molecule such as an antigen, or preferably, specifically binds to a target molecule that binds to folded polypeptide and does not bind to unfolded polypeptide such as Protein A. Structural amino acid positions of a VFR of CDR are identified as amino acid positions less tolerant to amino acid substitutions without affecting the structural stability of the polypeptide.

Amino acid positions less tolerant to amino acid substitutions can be identified using a method such as alanine scanning mutagenesis or shotgun scanning as described in WO 01/44463 and analyzing the effect of loss of the wild type amino acid on structural stability at positions in the VFR or CDR. An amino acid position is important to maintaining the structure of the polypeptide if a wild type amino acid is replaced with a scanning amino acid in an amino acid position in a VFR and the resulting variant exhibits poor binding to a target molecule that binds to folded polypeptide. A structural amino acid position is, preferably, a position in which the ratio of sequences with the wild type amino acid at a position to sequences with the scanning amino acid at that position is at least about 3 to 1, 5 to 1, 8 to 1, or about 10 to 1 or greater.

Alternatively, structural amino acid positions and nonstructural amino acid positions in a VFR or CDR can be determined by calculating the Shannon entropy at each position that is selected based on solvent accessibility and/or participation in forming the antigen binding pocket. Antibody variable domains with each selected amino acid position (whether a CDR or FR position) are randomized and selected for stability by binding to a molecule that binds folded antibody variable domains, such as protein A. Binders are isolated and sequenced and the sequences are compared to a database of human and/or mouse antibody variable domain sequences. The per residue variation in the randomized population can be estimated using the Shannon entropy calculation, with a value close to about 0 indicating that the amino acid in that position is conserved and values close to about 4.23 representing an amino acid position that is tolerant to substitution with all 20 amino acids. In some embodiments, a structural amino acid position is identified as a position that has a Shannon entropy value of about 3 or less.

In a further embodiment, structural amino acid positions can be determined based on weighted hydrophobicity for example, according to the method of Kyte and Doolittle. Structural amino acid positions and nonstructural amino acid positions in a VFR or CDR can be determined by calculating the weighted hydrophobicity at each position that is selected based on solvent accessibility and/or participation in forming the antigen binding pocket. Antibody variable domains with each selected amino acid position (whether a CDR or FR position) are randomized and selected for stability by binding to a molecule that binds folded antibody variable domains, such as protein A. Binders are isolated and sequenced. The weighted hydrophobicity at each position is calculated and those positions that have a weighted hydrophobicity of greater than the average hydrophobicity for any amino acid are selected as structural amino acid positions. The weighted hydrophobicity is preferably greater than −0.5, and more preferably, greater than 0 or 1.

In some embodiments, a plurality of antibody variable domains is generated, wherein each antibody variable domain comprises a variant VFR region. The variant VFR region of members of the plurality or population of antibody variable domains differ from one another. The variant VFR region comprises at least one structural amino acid position having a variant amino acid, wherein the structural amino acid position is substituted with up to six different amino acids, and the variant amino acid comprises, or is selected from the group consisting of the six different amino acids, and at least one nonstructural amino acid position that has a variant amino acid that comprises, consists essentially of, or consists of any of the naturally occurring amino acids. In some embodiments, the VFR region amino acid positions are those that form at least a portion of an antigen binding loop or groove and may contact antigen. In some embodiments, the variant amino acids are encoded by a nonrandom codon set encoding six amino acids or less.

In some embodiments, structural amino acid positions in a VFR are selected and/or located near the N and C terminus of the VFR allowing for a central portion that can be varied. The structural amino acid positions are selected as the boundaries for a CDR or VFR loop of contiguous amino acids that can be varied randomly, if desired. The variant VFR regions can have a N terminal flanking region in which some or all of the amino acid positions have limited diversity, a central portion comprising at least one or more nonstructural amino acid position that can be varied in length and sequence, and C-terminal flanking sequence in which some or all amino acid positions have limited diversity.

The length of the N terminal flanking region, central portion, and C-terminal flanking region is determined by selecting the length of VFR, randomizing each position and identifying the structural amino acid positions at the N and/or C-terminal ends of the VFR. The length of the N and C terminal flanking sequences should be long enough to include at least one structural amino acid position in each flanking sequence. In some embodiments, the length of the N-terminal flanking region is at least about from 1 to 4 contiguous amino acids, the central portion of one or more nonstructural positions can vary from about 1 to 20 contiguous amino acids, and the C-terminal portion is at least about from 1 to 6 contiguous amino acids. In some embodiments, the central portion of contiguous amino acids is about 5 to 15 amino acids. In other embodiments, the central portion of contiguous amino acids is about 5 to 10 amino acids.

In some embodiments, the structural amino acid positions in the N terminal flanking region are the first two N terminal amino acid positions of the region of the polypeptide to be diversified. The number of amino acids substituted at either or both of these positions is less than all 20 amino acids, preferably up to and no more than 6 different amino acids, more preferably about 1 to 6 different amino acids, more preferably about 1 to 5 different amino acids, more preferably about 1 to 4 different amino acids, more preferably about 1 to 3 different amino acids, and most preferably about 1-2 different amino acids. In some embodiments, the amino acids substituted at these positions are hydrophobic and/or cysteine and are encoded by a nonrandom codon set encoding six amino acids or less.

In some embodiments, the structural amino acid position in the C terminal flanking region of the region of the polypeptide to be diversified is the C terminal amino acid. The number of amino acids substituted at this position is less than all 20 amino acids, preferably up to and no more than six different amino acids, more preferably about 1 to 6 different amino acids, more preferably about 1 to 5 different amino acids, more preferably about 1 to 4 different amino acids, more preferably about 1 to 3 different amino acids, and most preferably about 1 to 2 different amino acids. Preferably, the amino acids substituted at this position are hydrophobic and/or cysteine and are encoded by a nonrandom codon set encoding six amino acids or less.

In one embodiment, the VFR is about 8 amino acids long and a library comprising a variant VFR is generated. The variant VFR comprises at least one structural amino acid position selected from the C-terminal amino acid position and at least one of the two N-terminal amino acid positions. The second amino acid position from the N terminal is preferably a charged amino acid that can form a hydrogen bond with another VFR amino acid residue.

In one embodiment, the VFR is an 8 amino acid loop corresponding to amino acid positions 71 to 78 in the heavy chain of an antibody variable domain or a monobody. The structural amino acids positions comprise, consist essentially of, or consist of the first two N terminal amino acid positions and the C terminal amino acid position corresponding to amino acid positions 71, 72, and 78, respectively. In some embodiments, the N and C terminal residues are either cysteines and/or hydrophobic amino acids. When both the N and C terminal amino acids are cysteines, they may form an intra-domain disulfide bond. In some embodiments, the N and/or C terminal amino acid positions are substituted with a hydrophobic amino acid and/or cysteine. In some embodiments, the N terminal amino acid position corresponding to position 71 is substituted with C, F, Y, W, M, or L. In other embodiments, this position is substituted with C, F, or Y. In some embodiments, position 72 is substituted with D, N, or S and in other embodiments, with D or E. In some embodiments, position 78 is substituted with M, C, F, V, or I and in other embodiments, with C or F.

Once the structural amino acid positions are identified, diversity is minimized or limited at these positions in order to provide a library with a diverse VFR region while minimizing the structural perturbations. The number of amino acids that are substituted at a structural amino acid position is preferably no more than and up to six different amino acids, preferably about 1 to 6 different amino acids, more preferably about 1 to 5 different amino acids, more preferably about 1 to 4 different amino acids, more preferably about 1 to 3 different amino acids, and most preferably about 1 to 2 different amino acids. In some embodiments, a variant amino acid at a structural amino acid position is encoded by one or more nonrandom codon sets. The nonrandom codon sets encode multiple amino acids for a particular positions, for example, about 1 to 6 amino acids, about 1 to 5 amino acids, about 1 to 4 amino acids, about 1 to 3 amino acids, or about 1 to 2 amino acids.

In some embodiments, the amino acids that are substituted at structural positions are those that are found at that position in a randomly generated VFR population at a frequency at least one standard deviation above the average frequency for any amino acid at the position. Preferably, the frequency is at least 60% or greater than the average frequency for any amino acid at that position, more preferably the frequency is at least one standard deviation (as determined using standard statistical methods) greater than the average frequency for any amino acid at that position. In another embodiment, the set of amino acids selected for substitution at the structural amino acid positions comprise, consist essentially of, or consist of the set of amino acids that are found in 50% of the antibody variable domains generated randomly. In another embodiment, the set of amino acids selected for substitution at the structural amino acid positions comprise, consist essentially of, or consist of up to 6 amino acids that occur most commonly at that positions as determined by calculating the fractional occurrence of each amino acid at that positions using standard methods. In some embodiments, the structural amino acids are preferably a hydrophobic amino acid and/or a cysteine as these amino acid positions are more likely to be buried and point into the core.

Another aspect of the invention provides polypeptides altered to include one or more changes in a core amino acid sequence of VFR. Preferably, the core amino acid sequence contacts an antigen or forms part of an antigen binding loop and the one or more changes in the VFR increases the binding affinity of the polypeptide for the antigen. In some embodiments, the VFR comprises an amino acid sequence comprising a core sequence of $A_1-A_2-A_3-A_4-A_5-A_6-A_7-A_8$ (SEQ ID NO:10) wherein at least one of $A_1$ and/or $A_8$ is a hydrophobic amino acid or a cysteine. In some embodiments, the amino acid at position $A_1$ and/or $A_8$ is L, I, V, W, Y, or F. In other embodiments, $A_1$ is C, F, Y, W, M, or L. In other embodiments, $A_8$ is M, C, F, V, or I. In further embodiments, $A_1$ is C, F, or Y and/or $A_8$ is C or F. In some embodiments, $A_2$ is D, N, or S and in other embodiments, $A_2$ is D or E. In other embodiments, the VFR comprises an amino acid sequence comprising a core sequence of $A_1-A_2-(A_3)_n-A_4$ (SEQ ID NO:11) wherein $A_1$ is C, F, or Y; $A_2$ is D, N or S; n is 5 to 15 contiguous amino acids and $A_3$ is an any amino acid; and $A_4$ is C or F. In some embodiments, $A_1$ is C, F, Y, W, M, or L. In other embodiments, $A_2$ is D or E. In further embodiments, $A_4$ is M, C, F, V, or I, and in other embodiments $A_4$ is C, F, or L. Some embodiments have a sequence of SEQ ID NO:18, SEQ ID NO:19, SEQ ID NO:20, SEQ ID NO:21, or SEQ ID NO:22. In some embodiments, the VFR amino acid positions correspond to amino acid positions 71-78 of a variable heavy chain domain. In some embodiments, the variable domain is a variable heavy chain domain.

The variant VFR is typically positioned between CDRs. In some embodiments, the variant VFR is positioned between CDRH2 and CDRH3 in an antibody variable domain and may be inserted within a framework region (FR) in a source variable domain. Typically, when the variant VFR is inserted into a source or wild type framework region, the variant VFR replaces all or a part of the source or wild type framework region. The location of insertion of the VFR can be determined by comparing the location of VFRs in naturally occurring antibody variable domains. In some embodiments, the VFR is located in a portion of FR3, for example, at amino acid positions corresponding amino acid positions 71 to 78.

The randomized VFR may also contain one or more nonstructural amino acid positions that have a variant amino acid. In some embodiments, the nonstructural amino acid positions comprise, consist essentially of, or consists of a contiguous amino acid sequence of up to 20 amino acids, more preferably about 1 to 20 amino acids, about 1 to 19 amino acids, about 1 to 18 amino acids, about 1 to 17 amino acids, about 1 to 16 amino acids, about 1 to 15 amino acids, about 1 to 14 amino acids, about 1 to 13 amino acids, about 1 to 12 amino acids, about 1 to 11 amino acids, about 1 to 10 amino acids, about 1 to 9 amino acids, about 1 to 8 amino acids, about 1 to 7 amino acids, about 1 to 6 amino acids, about 1 to 5 amino acids, about 1 to 4 amino acids, about 1 to 3 amino acids, about 1 to 2 amino acids. In some embodiments, contiguous amino acid sequences of 9-17 amino acids (for example, for CDR H3) or contiguous amino acid sequences of 5-15 amino acids are desirable.

Nonstructural amino acid positions may vary in sequence and length. In some embodiments, one or more nonstructural amino acid positions are located in between the N terminal and C terminal flanking regions. The nonstructural amino acid positions can be substituted randomly with any of the naturally occurring amino acids or with selected amino acids. In some embodiments, one or more nonstructural positions can have a variant amino acid encoded by a random codon set or a nonrandom codon. The nonrandom codon set preferably encodes at least a subset of the commonly occurring amino acids at those positions while minimizing nontarget sequences such as cysteine and stop codons. Examples of nonrandom codon sets include but are not limited to DVK, XYZ, and NVT. Examples of random codon sets include but are not limited to NNS and NNK.

In another embodiment, VFR diversity is generated using the codon set NNS. NNS and NNK encode the same amino acid group. However, there can be individual preferences for one codon set or the other, depending on the various factors known in the art, such as efficiency of coupling in oligonucleotide synthesis chemistry.

In some embodiments, the practitioner of methods of the invention may wish to modify the amount/proportions of individual nucleotides (G, A, T, C) for a codon set, such as the N nucleotide in a codon set such as in NNS. This is illustratively represented as XYZ codons. This can be achieved by, for example, doping different amounts of the nucleotides within a codon set instead of using a straight, equal proportion of the nucleotides for the N in the codon set. Such modifications can be useful for various purposes depending on the circumstances and desire of the practitioner. For example, such modifications can be made to more closely reflect the amino acid bias as seen in a natural diversity profile, such as the profile of VFR.

In some embodiments, nonstructural amino acid positions can also vary in length. For example, a first naturally occurring heavy chain variable domain may have 8 residues in VFR, such as residues 71-78, whereas a second naturally occurring heavy chain variable domain may comprise more than 8 residues in VFR. FR3 of naturally occurring heavy chains can have lengths ranging from 29 amino acids up to 41 amino acids depending on whether the CDRs are defined according to Kabat or Chothia. The contiguous loop of nonstructural amino acids can vary from about 1 to 20 amino acids, more preferably 5 to 15 amino acids and more preferably about 5 to 10 amino acids.

When the polypeptide is an antibody heavy chain variable domain of a monobody, diversity at other selected framework region residues may also be limited in order to preserve structural stability of the polypeptide. The diversity in framework regions can also be limited at those positions that form the light chain interface. Amino acids in positions at the light chain interface can be modified to provide for binding of the heavy chain to antigen in absence of the light chain. The amino acid positions that are found at the light chain interface in the VHH of camelid monobodies include amino acid position 37, amino acid position 45, amino acid position 47, and amino acid position 91. Heavy chain interface residues are those residues that are found on the heavy chain but have at least one side chain atom that is within 6 angstroms of the light chain. The amino acid positions in the heavy chain that are found at the light chain interface in human heavy chain variable domains include positions 37, 39, 44, 45, 47, 91, and 103.

In one embodiment, the polypeptide is a variable domain of a monobody and further comprises a framework 2 region of a heavy chain variable domain of a naturally occurring monobody, wherein amino acid position 37 of framework 2 has a phenylalanine, tyrosine, valine or tryptophan in that position. In another embodiment, the monobody variable domain further comprises a framework 2 region of a heavy chain, wherein the amino acid position 45 of the framework 2 region has an arginine, tryptophan, phenylalanine or leucine in that position. In another embodiment, the monobody variable domain further comprises a framework 2 region, wherein the amino acid position 47 has a phenylalanine, leucine, tryptophan or glycine residue in that position. In another embodiment, the monobody further comprises a framework 3 region of a heavy chain, wherein amino acid position 91 of the framework 3 region is a phenylalanine, threonine, or tyrosine.

Once the libraries with diversified VFR regions are prepared they can be selected and/or screened for binding to one or more target antigens. In addition, the libraries may be selected for improved binding affinity to particular target antigen. The target antigens may be any type of antigenic molecule but preferably are a therapeutic target molecule for example, interferons, VEGF, Her-2, cytokines, and growth factors. In specific embodiments, the target antigen may be one or more of the following: growth hormone, bovine growth hormone, insulin like growth factors, human growth hormone including n-methionyl human growth hormone, parathyroid hormone, thyroxine, insulin, proinsulin, amylin, relaxin, prorelaxin, glycoprotein hormones such as follicle stimulating hormone (FSH), leutinizing hormone (LH), hemapoietic growth factor, fibroblast growth factor, prolactin, placental lactogen, tumor necrosis factors, mullerian inhibiting substance, mouse gonadotropin-associated polypeptide, inhibin, activin, vascular endothelial growth factors, integrin, nerve growth factors such as NGF-beta, insulin-like growth factor-I and II, erythropoietin, osteoinductive factors, interferons, colony stimulating factors, interleukins, bone morphogenetic proteins, LIF,SCF,FLT-3 ligand and kit-ligand.

The libraries of the invention may be generated by mutating the amino acids that form the antigen binding pocket in VFR, and optionally one or more CDRs. A library of antibody variable domains can be generated, for example, having mutations in the solvent accessible antigen binding pocket positions of VFR, and optionally, CDRH1, CDRH2, and/or CDRH3. Another library can be generated having mutations in CDRL1, CDRL2 and CDRL3. These libraries can also be used in conjunction with each other to generate binders of desired affinities. For example, after one or more rounds of selection of heavy chain libraries for binding to a target antigen, a light chain library can be replaced into the population of heavy chain binders for further rounds of selection to increase the affinity of the binders.

Another aspect of the invention includes compositions of the polypeptides, fusion proteins or libraries of the invention. Compositions comprise a polypeptide, a fusion protein, or a population of polypeptides or fusion proteins in combination with a physiologically acceptable carrier.

2. Variant VFRs

As discussed above, randomized VFRs can generate polypeptide libraries that bind to a variety of target molecules, including antigens. These randomized VFRs can be incorporated into other antibody molecules or used to form a single chain mini-antibody with an antigen binding domain comprising a heavy chain variable domain but lacking a light chain. Within the VFR, amino acid positions that are primarily structural have limited diversity and other amino acids that do not contribute significantly to structural stability may be varied both in length and sequence diversity. A scaffold is preferably selected to have structural amino acid positions at the N and/or C-terminal amino acids, providing for a central portion of the VFR that can be randomized.

Polypeptides comprising a VFR having such a structure include camelid monobody, VHH, camelized antibodies, antibody or monobody variable domain obtained from a naïve or synthetic library, naturally occurring antibody or monobody, recombinant antibody or monobody, humanized antibody or monobody, germline derived antibody or monobody, chimeric antibody or monobody, and affinity matured antibody or monobody.

A number of different combinations of structural amino acid positions and nonstructural amino acid positions can be designed in a VFR template. One VFR variant comprises an amino acid sequence comprising a core sequence or having the formula of:

$A_1$-$A_2$-$(A_3)_n$-$A_4$ (SEQ ID NO:12), wherein $A_1$ is an amino acid selected from the group consisting of L, I, V, W, Y, F, and C;

$A_2$ is an amino acid selected from the group consisting of D, N, and S;

$A_3$ is any naturally occurring amino acid and n is 5 to 15 contiguous amino acids;

$A_4$ is an amino acid selected from the group consisting of L, I, V, W, Y, F, and C.

The amino acids to the left of the central portion of contiguous amino acids are referred to as the N terminal amino acids, and the amino acids to the right of the contiguous sequence are referred to as C terminal amino acids. In this particular embodiment, the N-terminal amino acid position and the C-terminal amino acid position have limited diversity and are preferably cysteine and/or a hydrophobic amino acid. The amino acid positions at $A_3$ can be any of the 20 naturally occurring amino acids, preferably L-amino acids. In some embodiments, the selected amino acids can be encoded by a nonrandom codon set that encodes six or less amino acids. The nonrandom codon set preferably encodes amino acids found or commonly occurring at those positions in randomly generated and/or naturally occurring antibodies or monobodies.

In some embodiments, $A_1$ corresponds to amino acid position 71, $A_2$ corresponds to amino acid position 72, $A_4$ corresponds to position 78, and $A_3$ is a contiguous amino acid sequence of 5 amino acids in between position 72 and 78. In other embodiments, $A_1$ is a C, $A_2$ is D, $A_3$ is a contiguous sequence of 5 amino acids and is any naturally occurring amino acid, and $A_4$ is C. In other embodiments, the cysteines at $A_1$ and $A_4$ form a disulfide bond.

In another embodiment, a variant VFR comprising a core amino acid sequence or has the formula of:

$A_1$-$A_2$-$(A_3)_n$-$A_4$ (SEQ ID NO:21), wherein $A_1$ is C, F, Y, M, W, or L;

$A_2$ is D, N, or S;

$A_3$ is any naturally occurring amino acid and n is 5 to 15 amino acids;

$A_4$ is M, C, F, V, or I.

In another embodiment, a VFR variant comprises an amino acid sequence comprising a core sequence or having the formula of:

$A_1$-$A_2$-$A_3$-$A_4$-$A_5$-$A_6$-$A_7$-$A_8$ (SEQ ID NO:13), wherein $A_1$ is an amino acid selected from the group consisting of L, I, V, W, Y, F, and C;

$A_2$, $A_3$, $A_4$, $A_5$, and $A_6$ are any naturally occurring amino acid;

$A_7$ is an amino acid selected from the group consisting of I, T, and V; and $A_8$ is an amino acid selected from the group consisting of L, I, V, W, Y, F, and C.

In yet another embodiment, a VFR variant comprises an amino acid sequence comprising a core sequence or having the formula of:

$A_1$-$A_2$-$A_3$-$A_4$-$A_5$-$A_6$-$A_7$-$A_8$ (SEQ ID NO:14), wherein $A_1$ is an amino acid selected from the group consisting of C, F, Y, M, W, or L;

$A_2$ is D;

$A_3$, $A_4$, $A_5$, and $A_6$ are any naturally occurring amino acid;

$A_7$ is an amino acid selected from the group consisting of I, T, and V; and $A_8$ is an amino acid selected from the group consisting of M, C, F, V, or I.

In another embodiment, a VFR variant comprises an amino acid sequence comprising a core sequence or having the formula of:

$A_1$-$A_2$-$A_3$-$A_4$-$A_5$-$A_6$-$A_7$-$A_8$ (SEQ ID NO:15), wherein $A_1$ is an amino acid selected from the group consisting of Y, F, and C;

$A_2$ is D;

$A_3$ is an amino acid selected from the group consisting of A, D, P, R, and S;

$A_4$ is an amino acid selected from the group consisting of A, D, and S;

$A_5$ is an amino acid selected from the group consisting of D, G, R, A, and T;

$A_6$ is an amino acid selected from the group consisting of G, K, R, and H;

$A_7$ is an amino acid selected from the group consisting of L, V, and I; and $A_8$ is an amino acid selected from the group consisting of F and C.

In some variations of the aforementioned embodiments, nonstructural amino acid positions can also vary in length. Due to requirements for antigen binding and/or structural features of the antigen, the VFR loop may have 8 or more amino acids.

In some embodiments, the core sequence forms a loop in an antigen binding domain of an antibody variable domain. Some of the amino acids of the core sequence may or may not contact that antigen. In other embodiments, the core sequence only includes those amino acid positions that contact the antigen.

In some embodiments, a scaffold for the variable framework can be designed comprising the following sequence $A_1$-$A_2$-$(A_3)_n$-$A_4$ (SEQ ID NO:16), wherein $A_1$ is C, F, or Y; $A_2$ is D or E; $A_3$ is any naturally occurring amino acid from 1 to 20 and $A_4$ is L, F, or C. In some embodiments, the variable framework scaffold comprises the sequence C-D-$(A_3)_n$-C (SEQ ID NO:17); wherein $A_3$ is any naturally occurring amino acid; and N is 1 to 20 amino acids.

3. Diversity in CDR Regions

The diversity of the library or population of the antibody variable domains is designed to maximize diversity while minimizing structural perturbations of the antibody variable domain to provide for increased ability to isolate high affinity antibodies. The number of positions mutated in the antibody variable domain is minimized or specifically targeted. In some embodiments, structural amino acid positions are identified and diversity is minimized at those positions to ensure a well-folded polypeptide. The positions mutated or changed include positions in FR and/or one or more of the CDR regions and combinations thereof.

The source polypeptide may be any antibody, antibody fragment, or antibody variable domain whether naturally occurring or synthetic. A polypeptide or source antibody variable domain can include an antibody, antibody variable domain, antigen binding fragment or polypeptide thereof, a monobody, VHH, a monobody or antibody variable domain obtained from a naïve or synthetic library, camelid antibodies, naturally occurring antibody or monobody, synthetic antibody or monobody, recombinant antibody or monobody, humanized antibody or monobody, germline derived antibody or monobody, chimeric antibody or monobody, and affinity matured antibody or monobody. In one embodiment, the polypeptide is an antibody variable domain that is a member of the Vh3 subgroup and preferably, is a camelid monobody.

Source antibody variable domains include but are not limited to antibody variable domains previously used to generate phage display libraries, such as VHH-RIG, VHH-VLK, VHH-LLR, and VHH-RLV (Bond et al., 2003, *J. Mol. Biol.*, 332:643-655), and humanized antibodies or antibody fragments, such as mAbs 4D5, 2C4, and A4.6.1. In an embodiment, the library is generated using the heavy chain variable domain (VHH) of a monobody. The small size and simplicity make monobodies attractive scaffolds for peptidomimetic and small molecule design, as reagents for high throughput protein analysis, or as potential therapeutic agents. The diversified VHH domains are useful, inter alia, in the design of enzyme inhibitors, novel antigen binding molecules, modular binding units in bispecific or intracellular antibodies, as binding reagents in protein arrays, and as scaffolds for presenting constrained peptide libraries.

One criterion for generating diversity in the polypeptide library is selecting amino acid positions that form an antigen binding pocket or groove in a single source antibody variable domain whether or not the residues actually contact the antigen. In some embodiments, the amino acids position may form all or part of a loop. One way of determining whether the amino acid position is part of a loop in an antigen binding site is to examine the three dimensional structure of the antibody variable domain, for example, for solvent accessible residues. If available, amino acids positions in proximity to antigen can also be selected. Three dimensional structure information of antibody variable domains are available for many antibodies or can be prepared using available molecular modeling programs. Solvent accessible amino acid positions can be found in FR and CDRs, and typically form loops on the exterior of the protein. Preferably, solvent accessible positions are determined using coordinates from a 3-dimensional model of an antibody, using a computer program such as the InsightII program (Accelrys, San Diego, Calif.). Solvent accessible positions can also be determined using algorithms known in the art (e.g., Lee and Richards, J. Mol. Biol. 55, 379 (1971) and Connolly, J. Appl. Cryst. 16, 548 (1983)). Determination of solvent accessible positions can be performed using software suitable for protein modeling and 3-dimensional structural information obtained from an antibody. Software that can be utilized for these purposes includes SYBYL Biopolymer Module software (Tripos Associates). Generally and preferably, where an algorithm (program) requires a user input size parameter, the "size" of a probe which is used in the calculation is set at about 1.4 Angstrom or smaller in radius. In addition, determination of solvent accessible regions and area methods using software for personal computers has been described by Pacios ((1994) "ARVOMOL/CONTOUR: molecular surface areas and volumes on Personal Computers", *Comput. Chem.* 18(4): 377-386; and "Variations of Surface Areas and Volumes in Distinct Molecular Surfaces of Biomolecules." *J. Mol. Model.* (1995), 1: 46-53). The location of amino acid positions involved in forming antigen binding pockets may vary in different antibody variable domains, but typically involve at least one or a portion of a CDR and/or a portion of the FR region.

In some instances, selection of solvent accessible residues is further refined by choosing solvent accessible residues that collectively form a minimum contiguous patch when the reference polypeptide or source antibody is in its 3-D folded structure. A compact (minimum) contiguous patch may comprise a portion of the FR and only a subset (for example, 2-5 CDRs) of the full range of CDRs, for example, CDRH1/H2/H3/L3. Solvent accessible residues that do not contribute to formation of such a patch may optionally be excluded from diversification. Refinement of selection by this criterion permits the practitioner to minimize, as desired, the number of residues to be diversified. This selection criterion may also be used, where desired, to choose residues to be diversified that may not necessarily be deemed solvent accessible. For example, a residue that is not deemed solvent accessible, but forms a contiguous patch in the 3-D folded structure with other residues that are deemed solvent accessible may be selected for diversification. Selection of such residues would be evident to one skilled in the art, and its appropriateness can also be determined empirically and according to the needs and desires of the skilled practitioner.

CDR diversity may be limited at structural amino acid positions. A structural amino acid position refers to an amino acid position in a CDR of a polypeptide that contributes to the stability of the structure of the polypeptide such that the polypeptide retains at least one biological function such as specifically binding to a molecule such as an antigen, or preferably, specifically binds to a target molecule that binds to folded polypeptide and does not bind to unfolded polypeptide such as Protein A. Structural amino acid positions of a CDR are identified as amino acid positions less tolerant to amino acid substitutions without affecting the structural stability of the polypeptide.

Amino acid positions less tolerant to amino acid substitutions can be identified using a method such as alanine scanning mutagenesis or shotgun scanning as described in WO 01/44463 and analyzing the effect of loss of the wild type amino acid on structural stability at positions in the CDR. An amino acid position is important to maintaining the structure of the polypeptide if a wild type amino acid is replaced with a scanning amino acid in an amino acid position in a CDR and the resulting variant exhibits poor binding to a target molecule that binds to folded polypeptide. A structural amino acid position is, preferably, a position in which the ratio of sequences with the wild type amino acid at a position to sequences with the scanning amino acid at that position is at least about 3 to 1, 5 to 1, 8 to 1, or about 10 to 1 or greater.

Alternatively, structural amino acid positions and nonstructural amino acid positions in a CDR can be determined by calculating the Shannon entropy at each position that is selected based on solvent accessibility and/or participation in forming the antigen binding pocket. Antibody variable domains with each selected amino acid position (whether a CDR or FR position) are randomized and selected for stability by binding to a molecule that binds folded antibody variable domains, such as protein A. Binders are isolated and sequenced and the sequences are compared to a database of human and/or mouse antibody variable domain sequences. The per residue variation in the randomized population can be estimated using the Shannon entropy calculation, with a value close to about 0 indicating that the amino acid in that position is conserved and values close to about 4.23 representing an amino acid position that is tolerant to substitution with all 20 amino acids. A structural amino acid position is identified as a position that has a Shannon entropy value of about 3 or less.

In a further embodiment, structural amino acid positions can be determined based on weighted hydrophobicity, for example, according to the method of Kyte and Doolittle. Structural amino acid positions and nonstructural amino acid positions in a CDR can be determined by calculating the weighted hydrophobicity at each position that is selected based on solvent accessibility and/or participation in forming the antigen binding pocket. Antibody variable domains with each selected amino acid position (whether a CDR or FR position) are randomized and selected for stability by binding to a molecule that binds folded antibody variable domains, such as protein A. Binders are isolated and sequenced. The weighted hydrophobicity at each position is calculated and those positions that have a weighted hydrophobicity of greater than the average hydrophobicity for any amino acid are selected as structural amino acid positions. The weighted hydrophobicity is preferable greater than −0.5, and more preferably greater than 0 or 1.

In some embodiments, structural amino acid positions in a CDRH1 are selected or located near the N and C terminus of the CDRH1 allowing for a central portion that can be varied. The structural amino acid positions are selected as the boundaries for a CDRH1 loop of contiguous amino acids that can be varied randomly, if desired. The variant CDRH1 regions can have a N terminal flanking region in which some or all of the amino acid positions have limited diversity, a central portion comprising at least one or more nonstructural amino acid position that can be varied in length and sequence, and C-terminal flanking sequence in which some or all amino acid positions have limited diversity.

Initially, a CDRH1 region can include amino acid positions as defined by Chothia including amino acid positions 26 to 32. Additional amino acid positions can also be randomized on either side of the amino acid positions in CDRH1 as defined by Chothia, typically 1 to 3 amino acids at the N and/or C terminal end. The N terminal flanking region, central portion, and C-terminal flanking region is determined by selecting the length of CDRH1, randomizing each position and identifying the structural amino acid positions at the N and C-terminal ends of the CDR to set the boundaries of the CDR. The length of the N and C terminal flanking sequences should be long enough to include at least one structural amino acid position in each flanking sequence. In some embodiments, the length of the N-terminal flanking region is at least about from 1 to 4 contiguous amino acids, the central portion of one or more nonstructural positions can vary about 1 to 20 contiguous amino acids, and the C-terminal portion is at least about from 1 to 6 contiguous amino acids. In some embodiments, the central portion of contiguous amino acids can comprise, consist essentially of or consist of about 9 to 17 amino acids, about 9 to about 15 amino acids, and more preferably about 9 to 12 amino acids.

The structural amino acid positions are less diversified than the central portion of the CDRH1 which can be completely randomized if desired. At the structural amino acid positions, up to six, and preferably no more than six different amino acids are substituted, more preferably about 1 to 6 different amino acids, more preferably about 1 to 5 different amino acids, more preferably about 1 to 4 different amino acids, more preferably about 1-3 different amino acids, and most preferably about 1-2 different amino acids. In some embodiments, the structural amino acid position is substituted with one or more hydrophobic amino acids and is encoded by a nonrandom codon set encoding six or less amino acids.

In one embodiment, the CDRH1 is about 11 amino acids long and a library comprising a variant CDRH1 is generated. The variant CDRH1 comprises, consists essentially of, at least one structural amino acid position selected from the C-terminal amino acid position and the N-terminal amino acid position. The C-terminal amino acid position and/or the N-terminal amino acid position are preferably hydrophobes. The hydrophobic amino acids are selected from the group consisting of (in single letter code) L, I, V, W, Y, F, and M. In some embodiments, the N terminal amino acid corresponds to position 24 and is Y, F, V, or I and/or the C terminal amino acid corresponds to position 34 and is F, V, or I. The central portion comprises 9 contiguous amino acids that can be randomized, if desired.

In one embodiment, the CDRH1 is an 11 amino acid sequence corresponding to amino acid positions 24 to 34 in the heavy chain of a monobody. The structural amino acids positions comprise, consist essentially of, or consist of the N terminal amino acid position and the C terminal amino acid position corresponding to amino acid positions 24 and 34, respectively. In some embodiments, the N and C terminal residues are hydrophobic amino acids. In some embodiments, the hydrophobic amino acids are selected from the group consisting of L, I, V, W, Y, F, and M.

In some embodiments, structural amino acid positions in a CDRH2 are located near the N terminus of the CDRH2 allowing for a portion of CDRH2 adjacent to the N terminal that can be varied. The variant CDRH2 regions can have a N terminal flanking region in which some or all of the amino acid positions have limited diversity, and a portion comprising at least one or more nonstructural amino acid position that can be varied in length and sequence.

Initially, a CDRH2 region can include amino acid positions as defined by Chothia including amino acid positions 53 to 55. Additional amino acid positions can be randomized on either side of the amino acid positions in CDRH2 as defined by Chothia, typically 1 to 3 amino acids on the N and/or C terminus. The length of the N terminal flanking region, and randomized central portion is determined by selecting the length of CDRH2, randomizing each position and identifying the structural amino acid positions at the N terminal ends of the CDR. The length of the N terminal flanking sequence should be long enough to include at least one structural amino acid position. In some embodiments, the length of the N-terminal flanking region is at least about from 1 to 4 contiguous amino acids, and the randomized portion of one or more nonstructural positions can vary from about 1 to 20 contiguous amino acids. The central portion of contiguous amino acids can comprise, consist essentially of or consist of about 5 to about 15 amino acids and more preferably about 5 to 12 amino acids.

The structural amino acid positions are less diversified than the central portion of the CDRH2 which can be completely randomized if desired. The structural amino acid positions are substituted with up to six different amino acids, and preferably no more than six different amino acids are substituted, more preferably about 1 to 6 different amino acids, more preferably about 1 to 5 different amino acids, more preferably about 1 to 4 different amino acids, more preferably about 1-3 different amino acids, and most preferably about 1-2 different amino acids. In some embodiments, the structural amino acid position is substituted with one or more hydrophobic amino acids and is encoded by a nonrandom codon set encoding six or less amino acids.

In one embodiment, the CDRH2 is about 6 amino acids long and a library comprising a variant CDRH2 is generated. The variant CDRH2 comprises, consists essentially of, or consists of, at least one structural amino acid position at the N-terminal amino acid position. The N-terminal amino acid position is preferably a hydrophobic amino acid. The hydrophobic amino acids are selected from the group consisting of (in single letter code) L, I, V, W, Y, M, and F. The central portion comprises 5 contiguous amino acids that can be randomized, if desired.

In one embodiment, the CDRH2 is a 6 amino acid loop corresponding to amino acid positions 51 to 56 in the heavy chain of a monobody. The structural amino acids positions comprise, consist essentially of or consist of the N terminal amino acid position corresponding to amino acid position 51. In some embodiments, the N terminal residues is a hydrophobic amino acid. In preferred embodiments, the hydrophobic amino acids are selected from the group consisting of F, I and L and in other embodiments, the hydrophobic amino acid is F or L.

In some embodiments, structural amino acid positions in a CDRH3 are located near the N and C terminus of the CDRH3 allowing for a central portion that can be varied. The variant CDRH3 regions can have a N terminal flanking region in which some or all of the amino acid positions have limited diversity, a central portion comprising at least one or more nonstructural amino acid position that can be varied in length and sequence, and C-terminal flanking sequence in which some or all amino acid positions have limited diversity.

The length of the N terminal flanking region, central portion, and C-terminal flanking region is determined by selecting the length of CDRH3, randomizing each position and identifying the structural amino acid positions at the N and C-terminal ends of the CDRH3. The length of the N and C terminal flanking sequences should be long enough to include at least one structural amino acid position in each flanking sequence. In some embodiments, the length of the N-terminal flanking region is at least about from 1 to 4 contiguous amino acids, the central portion of one or more nonstructural positions can vary from about 1 to 20 contiguous amino acids, and the C-terminal portion is at least about from 1 to 6 contiguous amino acids.

In one embodiment, the CDRH3 is about 17 amino acids long and a library comprising a variant CDRH3 is generated. The variant CDRH3 comprises, consists essentially of, or consist of, at least one structural amino acid position selected from at least one or two N terminal amino acids and at least one of the last six C terminal amino acids. The central portion comprises 11 amino acids that can be randomized if desired.

In one embodiment, the CDRH3 is an amino acid loop corresponding to amino acid positions 96 to 101 in the heavy chain of a monobody. The structural amino acids positions comprise, consist essentially of or consist of the two N terminal amino acid positions corresponding to amino acid positions 96, and 97, respectively. Table 4 shows the positions of the insertion of a randomized loop of amino acids into CDRH3. (SEQ ID NO:7)

specific embodiment, the N terminal amino acids are RI (positions 96 and 97) and the C terminal amino acids are WVTW (positions 100i, 100j, 100k, 100l) (SEQ ID NO:8).

The amino acids that are substituted at structural positions are those that are found at that position in a randomly generated CDR population at a frequency at least one standard deviation above the average frequency for any amino acid at the position. Preferably, the frequency is at least 60% or greater than the average frequency for any amino acid at that position, more preferably the frequency is at least one standard deviation (as determined using standard statistical methods) greater than the average frequency for any amino acid at that position. In another embodiment, the set of amino acids selected for substitution at the structural amino acid positions comprise, consist essentially of or consist of a set of amino acids that are found in 50% of the antibody variable domains generated by randomizing CDRs and FR. In another embodiment, the set of amino acids selected for substitution at the structural amino acid positions comprise, consist essentially of or consist of the 6 amino acids that occur most commonly at that position as determined by calculating the fractional occurrence of each amino acid at that position using standard methods. In some embodiments, the structural amino acids are preferably a hydrophobic amino acid or a cysteine as these amino acid positions are more likely to be buried and point into the core.

The structural amino acid positions are less diversified than the central portion of the CDRH3 which can be completely randomized if desired. At the structural amino acid positions, up to six different amino acids and preferably, no more than six different amino acids are substituted, more preferably about 1 to 6 different amino acids, more preferably about 1 to 5 different amino acids, more preferably about 1 to 4 different amino acids, more preferably about 1-3 different amino acids, and most preferably about 1-2 different amino acids. In some embodiments, the structural amino acid position is substituted with one or more hydrophobic amino acids and are encoded by a nonrandom codon set encoding six amino acids or less.

The variant CDR is typically positioned between at amino acid positions that are typical boundaries for CDR regions in naturally occurring antibody variable domains and may be inserted within a CDR in a source variable domain. Typically, when the variant CDR is inserted into a source or wild type antibody variable domain, the variant CDR replaces all or a part of the source or wild type CDR. The location of insertion of the CDR can be determined by comparing the location of CDRs in naturally occurring antibody variable domains. Depending on the site of insertion the numbering can change.

The randomized CDR may also contain one or more nonstructural amino acid positions that have a variant amino acid.

TABLE 4

| C | G | A | G | X | X | X | X | X | X | X | X | X | X | X | X | X | X | X | X | D |
|---|---|---|---|---|---|---|---|---|---|---|---|---|---|---|---|---|---|---|---|---|
| 92 |  |  |  | 96 | 97 | 98 | 99 | 100 | a | b | c | d | e | f | g | h | i | j | k i | 101 |

In preferred embodiments, the N terminal residue at position 96 is selected from the group consisting of R, L, V, F, W and K. The amino acid residue that is second from the N terminus at position 97 is selected from the group consisting of I, L, V, R, W and S. The C terminal amino acid at position 100i is selected from the group consisting of W, G, R, M, S, A and H. The C terminal amino acid at position 100j is selected from the group consisting of V, L, P, G, S, E and W. In a Nonstructural amino acid positions may vary in sequence and length. In some embodiments, one or more nonstructural amino acid positions are located in between the N terminal and C terminal flanking regions. The nonstructural amino acid positions can be substituted randomly with any of the naturally occurring amino acids or with selected amino acids. In some embodiments, one or more nonstructural positions can have a variant amino acid encoded by a random codon set or a nonrandom codon. The nonrandom codon set preferably encodes at least a subset of the commonly occurring amino acids at those positions while minimizing nontarget sequences such as cysteine and stop codons. Examples of nonrandom codon sets include but are not limited to DVK, XYZ, and NVT. Examples of random codon sets include but are not limited to NNS and NNK.

In another embodiment, CDR diversity is generated using the codon set NNS. NNS and NNK encode the same amino acid group. However, there can be individual preferences for one codon set or the other, depending on the various factors known in the art, such as efficiency of coupling in oligonucleotide synthesis chemistry.

In some embodiments, the practitioner of methods of the invention may wish to modify the amount/proportions of individual nucleotides (G, A, T, C) for a codon set, such as the N nucleotide in a codon set such as in NNS. This is illustratively represented as XYZ codons. This can be achieved by, for example, doping different amounts of the nucleotides within a codon set instead of using a straight, equal proportion of the nucleotides for the N in the codon set. Such modifications can be useful for various purposes depending on the circumstances and desire of the practitioner. For example, such modifications can be made to more closely reflect the amino acid bias as seen in a natural diversity profile, such as the profile of CDR.

Once the libraries with diversified CDR regions are prepared they can be selected and/or screened for binding one or more target antigens. In addition, the libraries may be selected for improved binding affinity to particular target antigen. The target antigens may include any type of antigenic molecule but preferably is antibody to therapeutic target molecule for example, interferons, VEGF, Her-2, cytokines, and growth factors. In specific embodiments, the target antigen may be one or more of the following: growth hormone, bovine growth hormone, insulin like growth factors, human growth hormone including n-methionyl human growth hormone, parathyroid hormone, thyroxine, insulin, proinsulin, amylin, relaxin, prorelaxin, glycoprotein hormones such as follicle stimulating hormone (FSH), leutinizing hormone (LH), hemapoietic growth factor, fibroblast growth factor, prolactin, placental lactogen, tumor necrosis factors, mullerian inhibiting substance, mouse gonadotropin-associated polypeptide, inhibin, activin, vascular endothelial growth factors, integrin, nerve growth factors such as NGF-beta, insulin-like growth factor-I and II, erythropoietin, osteoinductive factors, interferons, colony stimulating factors, interleukins, bone morphogenetic proteins, LIF,SCF,FLT-3 ligand and kit-ligand. The target antigen can also include a molecule that preferentially binds to folded antibody variable domains and does not bind as well as to unfolded antibody variable domains. Some examples of these target antigens include protein A or protein L.

Antibody variable domains with targeted diversity in one or more CDRs can be combined with targeted diversity in a VFR region as well. Combination of regions may be diversified in order to provide for high affinity antigen binding molecules or to improve the affinity of a known antibody such as a humanized antibody.

4. Fusion Polypeptides

Fusion polypeptide constructs can be prepared for generating fusion polypeptides that bind with significant affinity to potential ligands.

In particular, fusion polypeptides comprising diversified VFR and/or CDR(s) and a heterologous polypeptide sequence (preferably that of at least a portion of a viral polypeptide) are generated, individually and as a plurality of unique individual polypeptides that are candidate binders to targets of interest. Compositions (such as libraries) comprising such polypeptides find use in a variety of applications, in particular as large and diverse pools of candidate immunoglobulin polypeptides (in particular, antibodies and antibody fragments) that bind to targets of interest.

In some embodiments, a fusion protein comprises an antibody variable domain, or an antibody variable domain and a constant domain, fused to all or a portion of a viral coat protein. Examples of viral coat proteins include infectivity protein PIII, major coat protein PVIII, p3, Soc, Hoc, gpD (of bacteriophage lambda), minor bacteriophage coat protein 6 (pVI) (filamentous phage; J Immunol Methods. 1999 Dec. 10; 231(1-2):39-51), variants of the M13 bacteriophage major coat protein (P8) (Protein Sci 2000 April; 9(4):647-54). The fusion protein can be displayed on the surface of a phage and suitable phage systems include M13KO7 helper phage, M13R408, M13-VCS, and Phi X 174, pJuFo phage system (J. Virol. 2001 August; 75(15):7107-13.v), hyperphage (Nat Biotechnol. 2001 January; 19(1):75-8). The preferred helper phage is M13KO7, and the preferred coat protein is the M13 Phage gene III coat protein.

Tags useful for detection of antigen binding can also be fused to either an antibody variable domain not fused to a viral coat protein or an antibody variable domain fused to a viral coat protein. Additional peptides that can be fused to antibody variable domains include gD tags, c-Myc epitopes, poly-histidine tags, fluorescence proteins (e.g., GFP), or β-galactosidase protein which can be useful for detection or purification of the fusion protein expressed on the surface of the phage or cell.

These constructs may also comprise a dimerizable sequence that when present as a dimerization domain in a fusion polypeptide provides for increased tendency for heavy chains to dimerize to form dimers of Fab or Fab' antibody fragments/portions. These dimerization sequences may be in addition to any heavy chain hinge sequence that may be present in the fusion polypeptide. Dimerization domains in fusion phage polypeptides bring two sets of fusion polypeptides (LC/HC-phage protein/fragment (such as pIII)) together, thus allowing formation of suitable linkages (such as interheavy chain disulfide bridges) between the two sets of fusion polypeptide. Vector constructs containing such dimerization sequences can be used to achieve divalent display of antibody variable domains, for example the diversified fusion proteins described herein, on phage. Preferably, the intrinsic affinity of each monomeric antibody fragment (fusion polypeptide) is not significantly altered by fusion to the dimerization sequence. Preferably, dimerization results in divalent phage display which provides increased avidity of phage binding, with significant decrease in off-rate, which can be determined by methods known in the art and as described herein. Dimerization sequence-containing vectors of the invention may or may not also include an amber stop codon 5' of the dimerization sequence. Dimerization sequences are known in the art, and include, for example, the GCN4 zipper sequence (GRMKQLEDKVEELL-SKNYHLENEVARLKKLVGERG) (SEQ ID NO:9).

5. Polynucleotides, Vectors, Host Cells, and Recombinant Methods a. Oligonucleotides and Recombinant Methods Methods of substituting an amino acid of choice into a template nucleic acid are well established in the art, some of which are described herein. For example, libraries can be created by targeting solvent accessible antigen binding pocket amino acid positions in VFR, and optionally in one or more CDRs, for amino acid substitution with variant amino acids using the Kunkel method. See, for e.g., Kunkel et al., Methods Enzymol. (1987), 154:367-382. Generation of randomized sequences is also described below in the Examples.

The sequence of oligonucleotides includes one or more of the designed codon sets for the solvent accessible antigen binding pocket positions in a CDR or VFR. A codon set is a set of different nucleotide triplet sequences used to encode desired variant amino acids. Codon sets can be represented using symbols to designate particular nucleotides or equimolar mixtures of nucleotides as shown in below according to the IUB code.

IUB Codes
G Guanine
A Adenine
T Thymine
C Cytosine
R (A or G)
Y (C or T)
M (A or C)
K (G or T)
S (C or G)
W (A or T)
H (A or C or T)
B (C or G or T)
V (A or C or G)
D (A or G or T)
N (A or C or G or T)

For example, in the codon set DVK, D can be nucleotides A or G or T; V can be A or G or C; and K can be G or T. This codon set can present 18 different codons and can encode amino acids Ala, Trp, Tyr, Lys, Thr, Asn, Ser, Arg, Asp, Glu, Gly, and Cys. Other non random and random codon sets are known to those of skill in the art.

Oligonucleotide or primer sets can be synthesized using standard methods. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one method, nucleic acid sequences encoding variant amino acids can be created by oligonucleotide-mediated mutagenesis. This technique is well known in the art as described by Zoller et al, 1987, Nucleic Acids Res. 10:6487-6504. Briefly, nucleic acid sequences encoding variant amino acids are created by hybridizing an oligonucleotide set encoding the desired codon sets to a DNA template, where the template is the single-stranded form of the plasmid containing a variable region nucleic acid template sequence. After hybridization, DNA polymerase is used to synthesize an entire second complementary strand of the template that will thus incorporate the oligonucleotide primer, and will contain the codon sets as provided by the oligonucleotide set.

Generally, oligonucleotides of at least 25 nucleotides in length are used. An optimal oligonucleotide will have 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that described by Crea et al., Proc. Nat'l. Acad. Sci. USA, 75:5765 (1978).

The DNA template is generated by those vectors that are either derived from bacteriophage M13 vectors (the commercially available M13 mp18 and M13 mp19 vectors are suitable), or those vectors that contain a single-stranded phage origin of replication as described by Viera et al., Meth. Enzymol., 153:3 (1987). Thus, the DNA that is to be mutated can be inserted into one of these vectors in order to generate single-stranded template. Production of the single-stranded template is described in sections 4.21-4.41 of Sambrook et al., above.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as E. coli JM101. After growing the cells, they are plated onto agarose plates and screened using the oligonucleotide primer radiolabelled with a 32-Phosphate to identify the bacterial colonies that contain the mutated DNA.

The method described immediately above may be modified such that a homoduplex molecule is created wherein both strands of the plasmid contain the mutation(s). The modifications are as follows: The single stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al. ((1987) Meth. Enzymol., 153:3). Thus, the DNA that is to be mutated must be inserted into one of these vectors in order to generate single-stranded template. Production of the single-stranded template is described in sections 4.21-4.41 of Sambrook et al., supra.

According to another method, a library can be generated by providing upstream and downstream oligonucleotide sets, each set having a plurality of oligonucleotides with different sequences, the different sequences established by the codon sets provided within the sequence of the oligonucleotides. The upstream and downstream oligonucleotide sets, along with a variable domain template nucleic acid sequence, can be used in a polymerase chain reaction to generate a "library" of PCR products. The PCR products can be referred to as "nucleic acid cassettes", as they can be fused with other related or unrelated nucleic acid sequences, for example, viral coat proteins and dimerization domains, using established molecular biology techniques.

Oligonucleotide sets can be used in a polymerase chain reaction using a variable region nucleic acid template sequence as the template to create nucleic acid cassettes. The variable region nucleic acid template sequence can be any portion of the light or heavy immunoglobulin chains containing the target nucleic acid sequences (ie., nucleic acid sequences encoding amino acids targeted for substitution). The variable region nucleic acid template sequence is a portion of a double stranded DNA molecule having a first nucleic acid strand and complementary second nucleic acid strand. The variable region nucleic acid template sequence contains at least a portion of a variable domain and has at least one CDR. In some cases, the variable region nucleic acid template sequence contains more than one CDR. An upstream portion and a downstream portion of the variable region nucleic acid template sequence can be targeted for hybridization with members of an upstream oligonucleotide set and a downstream oligonucleotide set.

A first oligonucleotide of the upstream primer set can hybridize to the first nucleic acid strand and a second oligonucleotide of the downstream primer set can hybridize to the second nucleic acid strand. The oligonucleotide primers can include one or more codon sets and be designed to hybridize to a portion of the variable region nucleic acid template sequence. Use of these oligonucleotides can introduce two or more codon sets into the PCR product (ie., the nucleic acid cassette) following PCR. The oligonucleotide primer that hybridizes to regions of the nucleic acid sequence encoding the antibody variable domain includes portions that encode CDR residues that are targeted for amino acid substitution.

The upstream and downstream oligonucleotide sets can also be synthesized to include restriction sites within the oligonucleotide sequence. These restriction sites can facilitate the insertion of the nucleic acid cassettes [i.e., PCR reaction products] into an expression vector having additional antibody sequence. Preferably, the restriction sites are designed to facilitate the cloning of the nucleic acid cassettes without introducing extraneous nucleic acid sequences or removing original CDR or framework nucleic acid sequences.

Nucleic acid cassettes can be cloned into any suitable vector for expression of a portion or the entire light or heavy chain sequence containing the targeted amino acid substitutions generated via the PCR reaction. According to methods detailed in the invention, the nucleic acid cassette is cloned into a vector allowing production of a portion or the entire light or heavy chain sequence fused to all or a portion of a viral coat protein (i.e., creating a fusion protein) and displayed on the surface of a particle or cell. While several types of vectors are available and may be used to practice this invention, phagemid vectors are the preferred vectors for use herein, as they may be constructed with relative ease, and can be readily amplified. Phagemid vectors generally contain a variety of components including promoters, signal sequences, phenotypic selection genes, origin of replication sites, and other necessary components as are known to those of ordinary skill in the art.

When a particular variant amino acid combination is to be expressed, the nucleic acid cassette contains a sequence that is able to encode all or a portion of the heavy or light chain variable domain, and is able to encode the variant amino acid combinations. For production of antibodies containing these variant amino acids or combinations of variant amino acids, as in a library, the nucleic acid cassettes can be inserted into an expression vector containing additional antibody sequence, for example all or portions of the variable or constant domains of the light and heavy chain variable regions. These additional antibody sequences can also be fused to other nucleic acids sequences, such as sequences that encode viral coat proteins and therefore allow production of a fusion protein.

Methods for conducting alanine scanning mutagenesis are known to those of skill in the art and are described in WO 01/44463 and Morrison and Weiss, Cur. Opin. Chem. Bio., 5:302-307 (2001). Alanine scanning mutagenesis is a site directed mutagenesis method of replacing amino acid residues in a polypeptide with alanine to scan the polypeptide for residues involved in an interaction of interest. Standard site-directed mutagenesis techniques are utilized to systematically substitute individual positions in a protein with an alanine residue. Combinatorial alanine scanning allows multiple alanine substitutions to be assessed in a protein. Amino acid residues are allowed to vary only as the wild type or as an alanine. Utilizing oligonucleotide-mediated mutagenesis or cassette mutagenesis, binomial substitutions of alanine or seven wild type amino acids may be generated. For these seven amino acids, namely aspartic acid, glutamic acid, glycine, proline, serine, threonine, and valine, altering a single nucleotide can result in a codon for alanine. Libraries with alanine substitutions in multiple positions are generated by cassette mutagenesis or degenerate oligonucleotides with mutations in multiple positions. Shotgun scanning utilizes successive rounds of binding selection to enrich residues contributing binding energy to the receptor-ligand interaction.

b. Vectors

One aspect of the invention includes a replicable expression vector comprising a nucleic acid sequence encoding a gene fusion, wherein the gene fusion encodes a fusion protein comprising an antibody variable domain, or an antibody variable domain and a constant domain, fused to all or a portion of a viral coat protein. Also included is a library of diverse replicable expression vectors comprising a plurality of gene fusions encoding a plurality of different fusion proteins including a plurality of the antibody variable domains generated with diverse sequences as described above. The vectors can include a variety of components and are preferably constructed to allow for movement of antibody variable domain between different vectors and/or to provide for display of the fusion proteins in different formats.

Examples of vectors include phage vectors. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

Examples of viral coat proteins include infectivity protein PIII, major coat protein PVIII, p3, Soc, Hoc, gpD (of bacteriophage lambda), minor bacteriophage coat protein 6 (pVI) (filamentous phage; J. Immunol. Methods, 1999, 231(1-2): 39-51), variants of the M13 bacteriophage major coat protein (P8) (Protein Sci 2000 April; 9(4):647-54). The fusion protein can be displayed on the surface of a phage and suitable phage systems include M13KO7 helper phage, M13R408, M13-VCS, and Phi X 174, pJuFo phage system (J. Virol. 2001 August; 75(15):7107-13), hyperphage (Nat Biotechnol. 2001 January; 19(1):75-8). The preferred helper phage is M13KO7, and the preferred coat protein is the M13 Phage gene III coat protein. The preferred host is E. coli, and protease deficient strains of E. coli. Vectors, such as the fth1 vector (Nucleic Acids Res. 2001 May 15; 29(10):E50-0) can be useful for the expression of the fusion protein.

The expression vector also can have a secretory signal sequence fused to the DNA encoding each subunit of the antibody or fragment thereof. This sequence is typically located immediately 5' to the gene encoding the fusion protein, and will thus be transcribed at the amino terminus of the fusion protein. However, in certain cases, the signal sequence has been demonstrated to be located at positions other than 5' to the gene encoding the protein to be secreted. This sequence targets the protein to which it is attached across the inner membrane of the bacterial cell. The DNA encoding the signal sequence may be obtained as a restriction endonuclease fragment from any gene encoding a protein that has a signal sequence. Suitable prokaryotic signal sequences may be obtained from genes encoding, for example, LamB or OmpF (Wong et al., Gene, 68:1931 (1983), MalE, PhoA and other genes. A preferred prokaryotic signal sequence for practicing this invention is the E. coli heat-stable enterotoxin II (STII) signal sequence as described by Chang et al., Gene 55:189 (1987), and malE.

The vector also typically includes a promoter to drive expression of the fusion protein. Promoters most commonly used in prokaryotic vectors include the lac Z promoter system, the alkaline phosphatase pho A promoter, the bacteriophage $\gamma$-$_{PL}$ promoter (a temperature sensitive promoter), the tac promoter (a hybrid trp-lac promoter that is regulated by the lac repressor), the tryptophan promoter, and the bacteriophage T7 promoter. For general descriptions of promoters, see section 17 of Sambrook et al. supra. While these are the most commonly used promoters, other suitable microbial promoters may be used as well.

The vector can also include other nucleic acid sequences, for example, sequences encoding gD tags, c-Myc epitopes, poly-histidine tags, fluorescence proteins (e.g., GFP), or beta-galactosidase protein which can be useful for detection or purification of the fusion protein expressed on the surface of the phage or cell. Nucleic acid sequences encoding, for example, a gD tag, also provide for positive or negative selection of cells or virus expressing the fusion protein. In some embodiments, the gD tag is preferably fused to an antibody variable domain which is not fused to the viral coat protein. Nucleic acid sequences encoding, for example, a polyhistidine tag, are useful for identifying fusion proteins including antibody variable domains that bind to a specific antigen using immunohistochemistry. Tags useful for detection of antigen binding can be fused to either an antibody variable domain not fused to a viral coat protein or an antibody variable domain fused to a viral coat protein.

Another useful component of the vectors used to practice this invention is phenotypic selection genes. Typical phenotypic selection genes are those encoding proteins that confer antibiotic resistance upon the host cell. By way of illustration, the ampicillin resistance gene (ampr), and the tetracycline resistance gene (tetr) are readily employed for this purpose.

The vector can also include nucleic acid sequences containing unique restriction sites and suppressible stop codons. The unique restriction sites are useful for moving antibody variable domains between different vectors and expression systems. The suppressible stop codons are useful to control the level of expression of the fusion protein and to facilitate purification of soluble antibody fragments. For example, an amber stop codon can be read as Gln in a supE host to enable phage display, while in a non-supE host it is read as a stop codon to produce soluble antibody fragments without fusion to phage coat proteins. These synthetic sequences can be fused to one or more antibody variable domains in the vector.

It is preferable to use vector systems that allow the nucleic acid encoding an antibody sequence of interest, for example a VFR having variant amino acids, to be easily removed from the vector system and placed into another vector system. For example, appropriate restriction sites can be engineered in a vector system to facilitate the removal of the nucleic acid sequence encoding an antibody or antibody variable domain having variant amino acids. The restriction sequences are usually chosen to be unique in the vectors to facilitate efficient excision and ligation into new vectors. Antibodies or antibody variable domains can then be expressed from vectors without extraneous fusion sequences, such as viral coat proteins or other sequence tags.

Between nucleic acid encoding antibody variable domain (gene 1) and the viral coat protein (gene 2), DNA encoding a termination codon may be inserted, such termination codons including UAG (amber), UAA (ocher) and UGA (opel). (Microbiology, Davis et al., Harper & Row, New York, 1980, pp. 237, 245-47 and 374). The termination codon expressed in a wild type host cell results in the synthesis of the gene 1 protein product without the gene 2 Protein Attached. However, growth in a suppressor host cell results in the synthesis of detectable quantities of fused protein. Such suppressor host cells are well known and described, such as E. coli suppressor strain (Bullock et al., BioTechniques 5:376-379 (1987)). Any acceptable method may be used to place such a termination codon into the mRNA encoding the fusion polypeptide.

The suppressible codon may be inserted between the first gene encoding a antibody variable domain, and a second gene encoding at least a portion of a phage coat protein. Alternatively, the suppressible termination codon may be inserted adjacent to the fusion site by replacing the last amino acid triplet in the antibody variable domain or the first amino acid in the phage coat protein. When the plasmid containing the suppressible codon is grown in a suppressor host cell, it results in the detectable production of a fusion polypeptide containing the polypeptide and the coat protein. When the plasmid is grown in a non-suppressor host cell, the antibody variable domain is synthesized substantially without fusion to the phage coat protein due to termination at the inserted suppressible triplet UAG, UAA, or UGA. In the non-suppressor cell the antibody variable domain is synthesized and secreted from the host cell due to the absence of the fused phage coat protein which otherwise anchored it to the host membrane.

In some embodiments, the VFR and/or CDR being diversified (randomized) may have a stop codon engineered in the template sequence (referred to herein as a "stop template"). This feature provides for detection and selection of successfully diversified sequences based on successful repair of the stop codon(s) in the template sequence due to incorporation of the oligonucleotide(s) comprising the sequence(s) for the variant amino acids of interest.

The light and/or heavy antibody variable domains can also be fused to an additional peptide sequence, the additional peptide sequence allowing the interaction of one or more fusion polypeptides on the surface of the viral particle or cell. These peptide sequences are herein referred to as "dimerization sequences", "dimerization peptides" or "dimerization domains". Suitable dimerization domains include those of proteins having amphipathic alpha helices in which hydrophobic residues are regularly spaced and allow the formation of a dimer by interaction of the hydrophobic residues of each protein; such proteins and portions of proteins include, for example, leucine zipper regions. The dimerization regions are preferably located between the antibody variable domain and the viral coat protein.

In some cases the vector encodes a single antibody-phage polypeptide in a single chain form containing, for example, both the heavy and light chain variable regions fused to a coat protein. In these cases the vector is considered to be "monocistronic", expressing one transcript under the control of a certain promoter. A vector may utilize an alkaline phosphatase (AP) or Tac promoter to drive expression of a monocistronic sequence encoding VL and VH domains, with a linker peptide between the VL and VH domains. This cistronic sequence is connected at the 5' end to an E. coli malE or heat-stable enterotoxin II (STII) signal sequence and at its 3' end to all or a portion of a viral coat protein. In some embodiments, the vector may further comprise a sequence encoding a dimerization domain (such as a leucine zipper) at its 3' end, between the second variable domain sequence and the viral coat protein sequence. Fusion polypeptides comprising the dimerization domain are capable of dimerizing to form a complex of two scFv polypeptides (referred to herein as "(ScFv)2-pIII)").

In other cases, the variable regions of the heavy and light chains can be expressed as separate polypeptides, the vector thus being "bicistronic", allowing the expression of separate transcripts. In these vectors, a suitable promoter, such as the Ptac or PhoA promoter, can be used to drive expression of a bicistronic message. A first cistron, encoding, for example, a light chain variable domain, is connected at the 5' end to a E. coli malE or heat-stable enterotoxin II (STII) signal sequence and at the 3' end to a nucleic acid sequence encoding a gD tag. A second cistron, encoding, for example, a heavy chain variable domain, is connected at its 5' end to a E. coli malE or heat-stable enterotoxin II (STII) signal sequence and at the 3' end to all or a portion of a viral coat protein.

c. Introduction of Vectors into Host Cells

Vectors constructed as described in accordance with the invention are introduced into a host cell for amplification and/or expression. Vectors can be introduced into host cells using standard transformation methods including electroporation, calcium phosphate precipitation and the like. If the vector is an infectious particle such as a virus, the vector itself provides for entry into the host cell. Transfection of host cells containing a replicable expression vector which encodes the gene fusion and production of phage particles according to standard procedures provides phage particles in which the fusion protein is displayed on the surface of the phage particle.

Replicable expression vectors are introduced into host cells using a variety of methods. In one embodiment, vectors can be introduced into cells using electroporation as described in WO/00106717. Cells are grown in culture in standard culture broth, optionally for about 6-48 hours (or to $OD_{600}$=0.6-0.8) at about 37° C., and then the broth is centrifuged and the supernatant removed (e.g. decanted). Initial purification is preferably by resuspending the cell pellet in a buffer solution (e.g. 1.0 mM HEPES pH 7.4) followed by recentriguation and removal of supernatant. The resulting cell pellet is resuspended in dilute glycerol (e.g. 5-20% v/v) and again recentrifuged to form a cell pellet and the supernatant removed. The final cell concentration is obtained by resuspending the cell pellet in water or dilute glycerol to the desired concentration.

A particularly preferred recipient cell is the electroporation competent E. coli strain of the present invention, which is E. coli strain SS320 (Sidhu et al., Methods Enzymol. (2000), 328:333-363). Strain SS320 was prepared by mating MC1061 cells with XL1-BLUE cells under conditions sufficient to transfer the fertility episome (F' plasmid) or XL1-BLUE into the MC1061 cells. Strain SS320 has been deposited with the American Type Culture Collection (ATCC), 10801 University Boulevard, Manassas, Va. USA, on Jun. 18, 1998 and assigned Deposit Accession No. 98795. Any F' episome which enables phage replication in the strain may be used in the invention. Suitable episomes are available from strains deposited with ATCC or are commercially available (CJ236, CSH18, DHF', JM101, JM103, JM105, JM107, JM109, JM110), KS1000, XL1-BLUE, 71-18 and others).

The use of higher DNA concentrations during electroporation (about 10×) increases the transformation efficiency and increases the amount of DNA transformed into the host cells. The use of high cell concentrations also increases the efficiency (about 10×). The larger amount of transferred DNA produces larger libraries having greater diversity and representing a greater number of unique members of a combinatorial library. Transformed cells are generally selected by growth on antibiotic containing medium.

d. Display of Fusion Polypeptides

Fusion polypeptides with an antibody variable domain can be displayed on the surface of a cell or virus in a variety of formats. These formats include single chain Fv fragment (scFv), F(ab) fragment, variable domain of a monobody and multivalent forms of these fragments. The multivalent forms preferably are a dimer of ScFv, Fab, or F(ab'), herein referred to as $(ScFv)_2$, $F(ab)_2$ and $F(ab')_2$, respectively. The multivalent forms of display are preferred in part because they have more than one antigen binding site which generally results in the identification of lower affinity clones and also allows for more efficient sorting of rare clones during the selection process.

Methods for displaying fusion polypeptides comprising antibody fragments, on the surface of bacteriophage, are well known in the art, for example as described in patent publication number WO 92/01047 and herein. Other patent publications WO 92/20791; WO 93/06213; WO 93/11236 and WO 93/19172, describe related methods and are all herein incorporated by reference. Other publications have shown the identification of antibodies with artificially rearranged V gene repertoires against a variety of antigens displayed on the surface of phage (for example, Hoogenboom & Winter, 1992, J. Mol. Biol., 227: 381-388; and as disclosed in WO 93/06213 and WO 93/11236).

When a vector is constructed for display in a scFv format, it includes nucleic acid sequences encoding an antibody variable light chain domain and an antibody variable heavy chain variable domain. Typically, the nucleic acid sequence encoding an antibody variable heavy chain domain is fused to a viral coat protein. One or both of the antibody variable domains can have variant amino acids in at least one CDR or VFR region. The nucleic acid sequence encoding the antibody variable light chain is connected to the antibody variable heavy chain domain by a nucleic acid sequence encoding a peptide linker. The peptide linker typically contains about 5 to 15 amino acids. Optionally, other sequences encoding, for example, tags useful for purification or detection can be fused at the 3' end of either the nucleic acid sequence encoding the antibody variable light chain or antibody variable heavy chain domain or both.

When a vector is constructed for F(ab) display, it includes nucleic acid sequences encoding antibody variable domains and antibody constant domains. A nucleic acid encoding a variable light chain domain is fused to a nucleic acid sequence encoding a light chain constant domain. A nucleic acid sequence encoding an antibody heavy chain variable domain is fused to a nucleic acid sequence encoding a heavy chain constant CH1 domain. Typically, the nucleic acid sequence encoding the heavy chain variable and constant domains are fused to a nucleic acid sequence encoding all or part of a viral coat protein. One or both of the antibody variable light or heavy chain domains can have variant amino acids in at least one CDR and/or VFR. The heavy chain variable and constant domains are preferably expressed as a fusion with at least a portion of a viral coat and the light chain variable and constant domains are expressed separately from the heavy chain viral coat fusion protein. The heavy and light chains associate with one another, which may be by covalent or non-covalent bonds. Optionally, other sequences encoding, for example, polypeptide tags useful for purification or detection, can be fused at the 3' end of either the nucleic acid sequence encoding the antibody light chain constant domain or antibody heavy chain constant domain or both.

Preferably a bivalent moiety, for example, a F(ab)$_2$ dimer or F(ab')$_2$ dimer, is used for displaying antibody fragments with the variant amino acid substitutions on the surface of a particle. It has been found that F(ab')$_2$ dimers have the same affinity as F(ab) dimers in a solution phase antigen binding assay but the off rate for F(ab')$_2$ are reduced because of a higher avidity in an assay with immobilized antigen. Therefore the bivalent format (for example, F(ab')$_2$) is a particularly useful format since it can allow the identification of lower affinity clones and also allows more efficient sorting of rare clones during the selection process.

6. Antibodies

The libraries described herein may be used to isolate antibody variable domains, antibodies, antibody fragment, or monobodies to an antigen of choice. Monobodies are antigen binding molecules that lack light chains. Although their antigen combining site is found only in a heavy chain variable domain, the affinities for antigens have been found to be similar to those of classical antibodies (Ferrat et al., *Biochem J.*, 366:415 (2002)). Because monobodies bind their targets with high affinity and specificity, monobodies may used as modules in the design of traditional antibodies. A traditional antibody may be constructed by converting a high affinity heavy chain antibody or monobody to a Fab or IgG and pairing the converted heavy chain antibody or monobody with an appropriate light chain. The monobodies may also be utilized to form novel antigen binding molecules or miniantibodies without the need for any light chain. These novel mini-antibodies or antigen binding molecules are similar to other single chain type antibodies, but the antigen binding domain is a heavy chain variable domain.

Antibody variable domains specific for a target antigen can be combined with each other or with constant regions to form an antigen binding antibody fragment or full length antibody. These antibodies can be used in purification, diagnostic and in therapeutic applications.

7. Uses and Methods

The invention provides novel and systematic methods for diversifying antibody variable domain sequences, and libraries comprising a multiplicity, generally a great multiplicity of diversified antibody variable domain sequences. Such libraries provide combinatorial libraries useful for, for example, screening for synthetic antibody or antigen binding polypeptides with desirable activities such as binding affinities and avidities. These libraries provide a tremendously useful resource for identifying immunoglobulin polypeptide sequences that are capable of interacting with any of a wide variety of target molecules. For example, libraries comprising diversified immunoglobulin polypeptides of the invention expressed as phage displays are particularly useful for, and provide a high throughput, efficient and automatable systems of, screening for antigen binding molecules of interest. In some embodiments, the diversified antibody variable domains are provided in a monobody that binds to antigen in the absence of light chains. Also provided are methods for designing VFR regions that can be used to generate a plurality of VFR regions. The population of variant VFR, optionally in combination with one or more variant CDRs, can then be utilized in libraries to identify novel antigen binding molecules.

The invention provides methods for generating and isolating novel antibodies or antigen binding fragments or polypeptides that preferably have a high affinity for a selected antigen. A plurality of different antibodies or antibody variable domains are prepared by mutating (diversifying) one or more selected amino acid positions in a source heavy chain variable domain to generate a diverse library of antigen binding variable domains with variant amino acids at those positions. The diversity in the variable domains is designed so that highly diverse libraries are obtained with minimal structural perturbation. In one aspect, the amino acid positions selected are those that are solvent accessible, for example as determined by analyzing the structure of a source antibody and/or natural immunoglobulin polypeptides. In another aspect, the amino acid positions are those positions in a VFR region that are structural, and for which diversity is limited while the remaining positions can be randomized to generate a library that is highly diverse and well folded.

Variable domain fusion proteins expressing the variant amino acids can be expressed on the surface of a phage or a cell and then screened for the ability of members of the group of fusion proteins to specifically bind a target molecule, such as a target protein, which is typically an antigen of interest or is a molecule that binds to folded polypeptide and does not bind to unfolded polypeptide or both. Target proteins may include protein L or Protein A which specifically binds to antibody or antibody fragments and can be used to enrich for library members that display correctly folded antibody fragments (fusion polypeptides). In another embodiment, a target molecule is a molecule that specifically binds to folded polypeptide and does not bind to unfolded polypeptide and does not bind at an antigen binding site. For example, the Protein A binding site of Vh3 antibody variable domains are found on the opposite B sheet from the antigen binding site. Another example of a target molecule includes an antibody or antigen binding fragment or polypeptide that does not bind to the antigen binding site and binds to folded polypeptide and does not bind to unfolded polypeptide, such as an antibody to the Protein A binding site. Target proteins can also include specific antigens, such as receptors, may be isolated from natural sources or prepared by recombinant methods by procedures known in the art.

Screening for the ability of a fusion polypeptide to bind a target molecule can also be performed in solution phase. For example, a target molecule can be attached with a detectable moiety, such as biotin. Phage that binds to the target molecule in solution can be separated from unbound phage by a molecule that binds to the detectable moiety, such as streptavidincoated beads where biotin is the detectable moiety. Affinity of binders (fusion polypeptide that binds to target) can be determined based on concentration of the target molecule used, using formulas and based on criteria known in the art.

Target antigens can include a number of molecules of therapeutic interest. Included among cytokines and growth factors are growth hormone, bovine growth hormone, insulin like growth factors, human growth hormone including n-methionyl human growth hormone, parathyroid hormone, thyroxine, insulin, proinsulin, amylin, relaxin, prorelaxin, glycoprotein hormones such as follicle stimulating hormone (FSH), leutinizing hormone (LH), hemapoietic growth factor, fibroblast growth factor, prolactin, placental lactogen, tumor necrosis factors, mullerian inhibiting substance, mouse gonadotropin-associated polypeptide, inhibin, activin, vascular endothelial growth factors, integrin, nerve growth factors such as NGF-beta, insulin-like growth factor-I and II, erythropoietin, osteoinductive factors, interferons, colony stimulating factors, interleukins, bone morphogenetic proteins, LIF,SCF,FLT-3 ligand and kit-ligand.

The purified target protein may be attached to a suitable matrix such as agarose beads, acrylamide beads, glass beads, cellulose, various acrylic copolymers, hydroxyalkyl methacrylate gels, polyacrylic and polymethacrylic copolymers, nylon, neutral and ionic carriers, and the like. Attachment of the target protein to the matrix may be accomplished by methods described in Methods in Enzymology, 44 (1976), or by other means known in the art.

After attachment of the target protein to the matrix, the immobilized target is contacted with the library expressing the fusion polypeptides under conditions suitable for binding of at least a portion of the phage particles with the immobilized target. Normally, the conditions, including pH, ionic strength, temperature and the like will mimic physiological conditions. Bound particles ("binders") to the immobilized target are separated from those particles that do not bind to the target by washing. Wash conditions can be adjusted to result in removal of all but the higher affinity binders. Binders may be dissociated from the immobilized target by a variety of methods. These methods include competitive dissociation using the wild-type ligand, altering pH and/or ionic strength, and methods known in the art. Selection of binders typically involves elution from an affinity matrix with a ligand. Elution with increasing concentrations of ligand should elute displayed binding molecules of increasing affinity.

The binders can be isolated and then reamplified or expressed in a host cell and subjected to another round of selection for binding of target molecules. Any number of rounds of selection or sorting can be utilized. One of the selection or sorting procedures can involve isolating binders that bind to protein L or an antibody to a polypeptide tag such as antibody to the gD protein or polyhistidine tag. Another selection or sorting procedure can involve multiple rounds of sorting for stability, such as binding to a target molecule that specifically binds to folded polypeptide and does not bind to unfolded polypeptide followed by selecting or sorting the stable binders for binding to an antigen (such as VEGF).

In some cases, suitable host cells are infected with the binders and helper phage, and the host cells are cultured under conditions suitable for amplification of the phagemid particles. The phagemid particles are then collected and the selection process is repeated one or more times until binders having the desired affinity for the target molecule are selected. Preferably at least 2 rounds of selection are conducted.

After binders are identified by binding to the target antigen, the nucleic acid can be extracted. Extracted DNA can then be used directly to transform *E. coli* host cells or alternatively, the encoding sequences can be amplified, for example using PCR with suitable primers, and then inserted into a vector for expression.

A preferred strategy to isolate high affinity binders is to bind a population of phage to an affinity matrix which contains a low amount of ligand. Phage displaying high affinity polypeptide is preferentially bound and low affinity polypeptide is washed away. The high affinity polypeptide is then recovered by elution with the ligand or by other procedures which elute the phage from the affinity matrix.

Preferably, the process of screening is carried out by automated systems to allow for high-throughput screening of library candidates.

In some cases these novel VFR sequences can be combined with other sequences generated by introducing variant amino acids via codon sets into other CDRs in the heavy and light chains, for example through a 2-step process. An example of a 2-step process comprises first determining binders (generally lower affinity binders) within one or more libraries generated by randomizing VFR, and optionally one or more CDRs, wherein the VFR is randomized and each library is different or, where the same domain is randomized, it is randomized to generate different sequences. VFR and/or CDR diversity from binders from a heavy chain library can then be combined with CDR diversity from binders from a light chain library (e.g. by ligating different CDR sequences together). The pool can then be further sorted against target to identify binders possessing increased affinity. For example, binders (for example, low affinity binders) obtained from sorting a VFR/H2, a VFR/H1/H2/H3 or an VFR/L3/H1/H2/H3 library may be combined with binders (for example, low affinity binders) obtained from sorting an VFR/L1/L2/H1/H2 or an VFR/L1/L2/L3 library, wherein the combined binders are then further sorted against a target of interest to obtain another set of binders (for example, high affinity binders). Novel antibody sequences can be identified that display higher binding affinity for example, to either the ErbB2 or VEGF antigens.

In some embodiments, libraries comprising polypeptides of the invention are subjected to a plurality of sorting rounds, wherein each sorting round comprises contacting the binders obtained from the previous round with a target molecule distinct from the target molecule(s) of the previous round(s). Preferably, but not necessarily, the target molecules are homologous in sequence, for example members of a family of related but distinct polypeptides, such as, but not limited to, cytokines (for example, alpha interferon subtypes).

Another aspect of the invention involves a method of designing a VFR region that is well folded and stable for phage display. The method involves generating a library comprising polypeptides with variant VFR regions, selecting the members of the library that bind to a target molecule that binds to folded polypeptide and does not bind to unfolded polypeptide, analyzing the members of the library to identify structural amino acid positions in the VFR region, identifying at least one amino acid that can be substituted at the structural amino acid position, wherein the amino acid identified is one that occurs significantly more frequently than random (one standard deviation or greater than the frequency of any amino acid at that position) in polypeptides selected for stability, and designing a VFR region that has at least one or the identified amino acids in the structural amino acid position. The method may further comprise selecting a VFR that has structural amino acid positions at the N and/or C-terminus of the VFR. For example, a VFR can be selected that has structural amino acid positions in one or more of the two N-terminal amino acids and/or at the C-terminal amino acid. In one embodiment, all of the structural amino acid positions have been substituted with one of the identified amino acids. The identified amino acids are preferably selected from the group consisting of hydrophobic amino acids and/or cysteine. Libraries with variant VFR regions can be generated and sorted for members of the library that bind to a target antigen such as a cytokine.

It is contemplated that the sequence diversity of libraries created by introduction of variant amino acids in VFR by any of the embodiments described herein can be increased by combining these VFR variations with variations in other regions of the antibody, specifically in CDRs of either the light or heavy chain variable sequences. It is contemplated that the nucleic acid sequences that encode members of this set can be further diversified by introduction of other variant amino acids in the CDRs of either the light or heavy chain sequences, via codon sets. Thus, for example, in one embodiment, VFR sequences from fusion polypeptides that bind a target antigen can be combined with diversified CDRH1, CDRH2, or CDRH3 sequences, or any combination of diversified CDRs.

Another aspect of the invention involves a method of generating a plurality of antibody variable domains, wherein each antibody variable domain comprises a variant VFR. The method comprises replacing an amino acid at least one structural amino acid position at the N terminus of the VFR with up to six different amino acids, replacing an amino acid in at least one nonstructural amino acid position with any naturally occurring amino acid, wherein said at least one nonstructural amino acids is a contiguous sequence of 1-20 amino acids and replacing an amino acid in at least one structural amino acid position at the C terminus of the VFR with up to six different amino acids. In some embodiments, the structural amino acid position is substituted using a nonrandom codon set that encodes less than six amino acids and that encodes one or more hydrophobic amino acids and/or cysteine. In some embodiments, the nonrandom codon set encodes one or more of V, F, L, I, Y, M, or W, and/or cysteine.

Another aspect of the invention involves a method of generating a population of polypeptides with variant VFR comprising identifying VFR amino acid positions as those FR amino acid position that form a loop of an antigen binding pocket; identifying at least one structural amino acid position and at least one nonstructural amino acid positions; and/or generating a population of polypeptides with a variant VFR region by replacing the amino acid at the at least one structural amino acid position with about 1 to 6 of the most commonly occurring amino acids at that position in a population of polypeptides with randomized VFR; and replacing at least one nonstructural amino acid position with a variant amino acid, wherein the variant amino acid is any one of the naturally occurring amino acids or is encoded by a nonrandom codon set to generate a population of polypeptides that have different amino acid sequences in VFR.

The method may further comprise generating a plurality of polypeptides with a variant CDR1 comprising identifying CDR1 amino acid positions that form a loop of an antigen binding pocket; identifying at least the structural amino acid position and at least one nonstructural amino acid position; and/or generating a population of polypeptides with a variant CDR1 region by replacing the amino acid at the at least one structural amino acid position with about 1 to 6 of the most commonly occurring amino acids at that position in a randomly generated population and replacing the nonstructural amino acid position with any of the naturally occurring amino acids or with a set of amino acids encoded by a nonrandom codon set to generate a population of polypeptides with different amino acid sequences in CDR1.

The method may further comprise generating a plurality of polypeptides with a variant CDR2, wherein the variant CDR2 is generated by a method comprising identifying CDR2 amino acid positions that form a loop of an antigen binding pocket; identifying at least the structural amino acid position and at least one nonstructural amino acid position; and/or generating a population of polypeptides with a variant CDR2 region by replacing the amino acid at the at least one structural amino acid position with about 1 to 6 of the most commonly occurring amino acids at that position in a randomly generated population and replacing the nonstructural amino acid position with any of the naturally occurring amino acids or with a set of amino acids encoded by a nonrandom codon set to generate a population of polypeptides with different amino acid sequences in CDR2.

The method may further comprise generating a plurality of polypeptides with a variant CDR3, wherein the variant CDR3 is generated by a method comprising identifying CDR3 amino acid positions that form a loop of an antigen binding pocket; identifying at least the structural amino acid position and at least one nonstructural amino acid position; and/or generating a population of polypeptides with a variant CDR3 region by replacing the amino acid at the at least one structural amino acid position with about 1 to 6 of the most commonly occurring amino acids at that position in a randomly generated population and replacing the nonstructural amino acid position with any of the naturally occurring amino acids or with a set of amino acids encoded by a nonrandom codon set to generate a population of polypeptides with different amino acid sequences in CDR3.

The methods of generating a population of polypeptides with variant VFR or CDR include randomizing nonstructural amino acid positions that are a loop of about 6 to 15 contiguous amino acids.

Another aspect of the invention is a method of generating a VFR scaffold antibody variable domain. The method involves generating a library of antibody variable domains randomized at each amino acid position in the VFR. The library is sorted against a target molecule that binds to folded polypeptide and does not bind to unfolded polypeptide. Multiple rounds of amplification and selection may take place. Preferably, at least three rounds of amplification and selection are conducted. At the fourth or fifth rounds, the sequence of each of the four most dominant clones is identified. The identity of the structural amino acid positions in any particular clone may be confirmed using, for example, combinatorial alanine scanning mutagenesis. A VFR scaffold is than prepared by limiting the diversity at the structural amino acid positions in a particular design and inserting a central portion of contiguous amino acids. The central portion may be randomized at one or more positions if desired.

Having generally described the invention, the same will be more readily understood by reference to the following examples, which are provided by way of illustration and are not intended as limiting.

All publications (including patents and patent applications) cited herein are hereby incorporated in their entirety by reference.

EXAMPLE 1

Generation of a Library of Variable Domains

We examined the three-dimensional structure of VHH-RIG, a heavy chain variable domain (Bond et al., 2003, *J.*

Figure 1B:
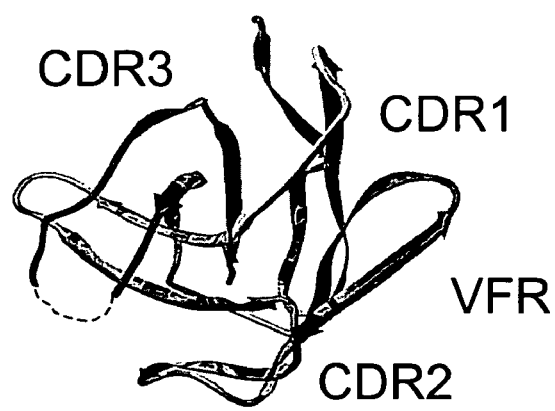
Figure 2:
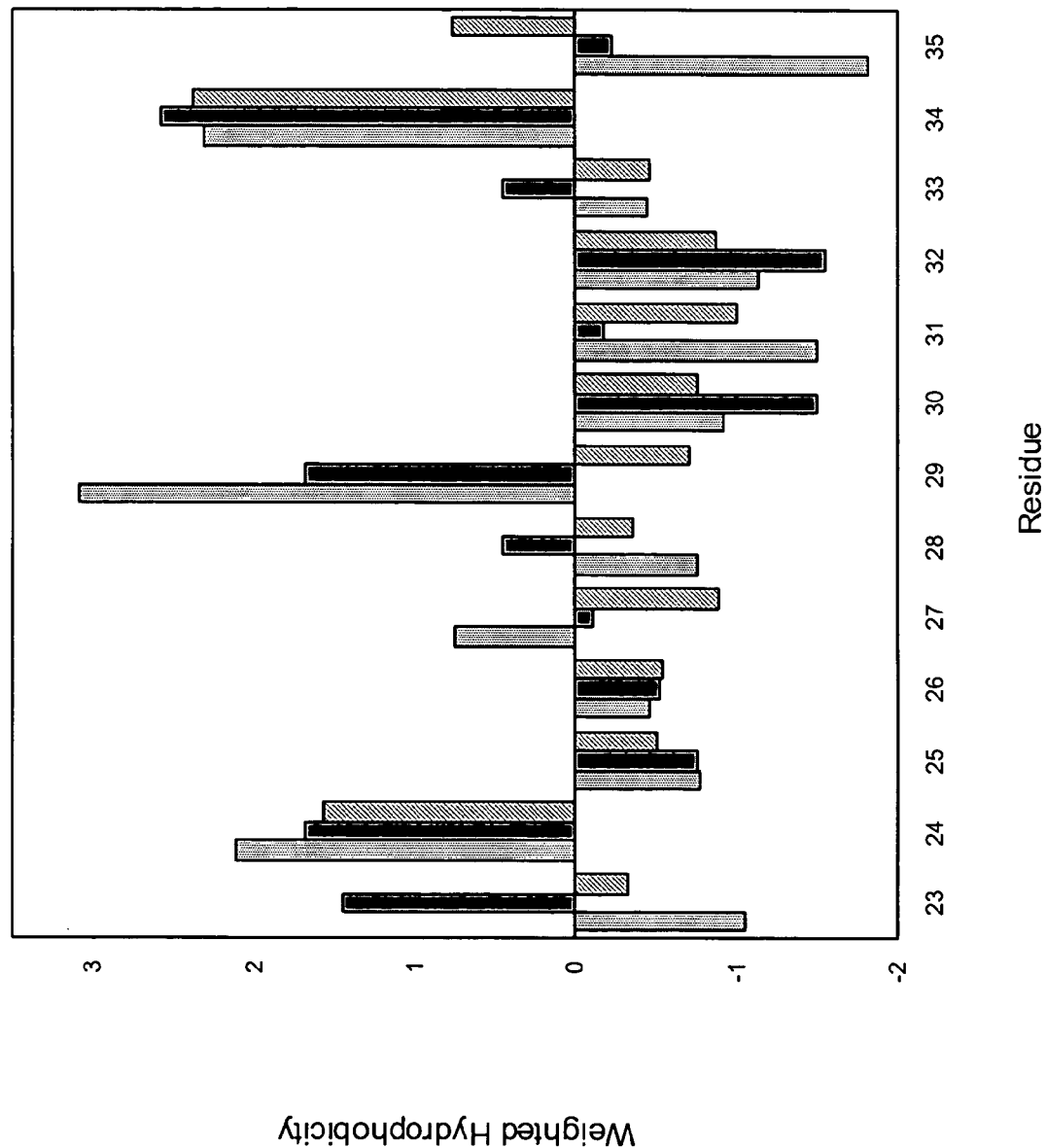
FIG. 2 shows the weighted Kyte-Doolittle hydrophobicity (Kyte & Doolittle, 1982, J. Mol. Biol., 157: 105-132) plot for CDRH1. Weighted hydrophobicities (y axis) were calculated for the distribution of amino acids observed at each position (x axis) in the structure-based database (Table 6 and FIG. 4; hatched (diagonal), the human/mouse VH domain database, and the camelid V.sub.HH domain database (Harmsen et al., 2000, Mol. Immunol., 37:579-590; dark gray). In the Kyte-Doolittle scale, the average hydrophobicity of the 20 natural amino acids is −0.5 and larger numbers indicate greater hydrophobicity.

*Mol. Biol.*, 332:643-655), and delineated four loops defining a continuous stretch of sequence that presents a large contiguous surface for potential antigen binding (FIG. 1). The four loops correspond to amino acid positions in CDRH1, CDRH2, CDRH3, and FRH3. Framework residues 71-78 (FRH3) form a loop that is part of the framework region between CDRH2 and CDRH3. FRH3 is not considered a natural hypervariable loop, however, it is structurally positioned to make contacts with antigen (Franklin et al., 2004, Cancer Cell, in press) and affinity maturation studies have shown that mutations in FRH3 can modulate binding affinity (Carter et al., 1992, *Proc. Natl. Acad. Sci. USA*, 89:4285-4289; Baca et al., 1997, *J. Biol. Chem.*, 272:10678-10684).

A database of VHH domain diversity was compiled to determine whether FRH3, similar to CDRH1, CDRH2, and CDRH3, is tolerant to variation and therefore useful in the design of synthetic antibody libraries. VHH domains do not require a light chain for expression. The absence of a light chain allowed for testing of sequence variation at each of the CDR and framework loops without the complication of light chain. To determine how tolerant each of the CDR loops and FRH3 loop are to variation, we constructed antibody libraries in which the sequence defining each of the CDR and FRH3 loops was replaced by a random sequence of equal length. The antibody libraries were based on the VHH-RIG scaffold, a previously described variable domain monobody (Bond et al., 2003, J. Mol. Biol., 332: 643-655). This scaffold is a heavy chain variable domain where the CDR3 region is positioned between amino acid positions 95 and 101. Amino acid positions 96 and 97 are fixed and have amino acids arginine and isoleucine, respectively. A randomized loop of amino acids varying in size can be inserted after amino acid position 97. The C terminal amino acids are in positions 100i, 100j, 100k, and 100l and have amino acids WVTW, respectively.

Methods and Materials

Construction of a phagemid for phage display of VHH-RIG scaffold. Vectors encoding fusion polypeptides comprising CDRH1, CDRH2, CDRH3, or FRH3 were constructed by modifying the phagemid pS1602. pS1602, which has the IPTG-inducible pTac promoter sequence and malE secretion signal sequence, contained a sequence of human growth hormone (hGH) fused to the C-terminal domain of the gene-3 minor coat protein (P3C). The sequence encoding hGH was removed, and the synthetic gene encoding llama anti HCG heavy chain monobody with RIG scaffold in CDRH3 (RIG) was substituted. The sequence of the llama anti-HCG monobody is provided in Table 2 and the sequence of the CDRH3 in the RIG scaffold is shown in Table 3. The resulting phagemid (pCB36624) encoded the following fusion product under the control of the IPTG-inducible $P_{tac}$ promoter: the maltose binding protein signal peptide, followed by RIG, followed by a FLAG epitope, followed by a Gly/Ser-rich linker peptide, followed by P3C.

Construction of phage-displayed libraries. Libraries were constructed as described in Bond et al., 2003, J. Mol. Biol., 332-643-655 and Sidhu et al., 2000, Methods Enzymol., 328: 333-363. For each of the four loops, we constructed a library in which the loop sequence was replaced with a random sequence of equal length. The loop boundaries for CDRH1, CDRH2, CDRH3, and FRH4 were derived from the Kabat (Kabat et al., Sequences of Proteins of Immunological Interest (National Institutes of Health, Bethesda, Md., 1987 and 1991)) and Chothia (Chothia and Lesk, 1987, J. Mol. Biol., 196:901-917) definitions of CDR boundaries. The CDRH1 region was fixed at the N-terminus at amino acid residue 23 and at the C-terminus at amino acid residue 35. The loop sequence of CDRH1 was 9 amino acids long and varied randomly. The CDRH2 region was fixed at the N-terminus at amino acid residue 51 and at the C-terminus at amino acid residue 56. The loop sequence of CDRH2 was 5 amino acids long and varied randomly. The CDRH3 region was fixed at the N-terminus at amino acid residues R1 (positions 96 and 97) and at the C-terminus with amino acid residues WVTW (positions 100i, 100j, 100k and 100l). The loop sequence of CDRH3 ranged from 7 to 15 amino acid residues in length and the loop sequence varied randomly and corresponded to amino acid positions 98 to 100h. The FRH3 region was fixed at the N-terminus at amino acid residue 71 and at the C-terminus at amino acid residue 78. The loop sequence of FRH3 was 6 amino acids long and varied randomly.

The random sequence was generated by a NNK degenerate codon (N=A/G/C/T, K=G/T) that contains 32 unique codons that together encode for all natural amino acids. Each library contained at least $5 \times 10^{10}$ unique members. Phage from the libraries were propagated in *Escherichia coli* XL1-Blue (Stratagene, San Diego, Calif.) with the addition of M13-KO7 helper phage (New England Biolabs, Beverly Mass.). After overnight growth in 2YT media at 37° C., phage were concentrated by precipitation with PEG/NaCl and resuspended in phosphate-buffered saline (PBS), 0.5% bovine serum albumin (BSA), 0.1% Tween®-20 (Sigma), as described in Sidhu et al., 2000, supra.

Sorting of phage-displayed libraries. Each library was separately cycled through two rounds of in vitro selection for binding to protein A, a ligand that binds to the VHH domain through contacts that do not involve any of the positions randomized in the libraries (Graille et al., 2000, *Proc. Natl. Acad. Sci. USA*, 97:5399-5404). Protein A binding was used to select for correctly folded VHH domains in vitro (de Wildt et al., 2000, *Nature Biotechnol.*, 18:989-994; Bond et al., 2003, *J. Mol. Biol.*, 332:643-655). In vitro selection with protein A allowed us to rapidly enrich each library population for members that displayed stable, correctly folded VHH domains.

NUNC 96-well Maxisorp™ immunoplates were coated overnight at 4° C. with protein A (5 μg/ml) (Sigma) and blocked for 1 h with BSA (Sigma, St. Louis, Mo.). Phage were quantitated by spectrophotometry at 268 nm (1 OD=$1.13 \times 10^{13}$/ml), and phage solutions (~$10^{12}$ phage/ml) were added to the coated immunoplates. Following a 2 h incubation to allow for phage binding, the plates were washed 12 times with PBS, 0.05% Tween®-20. Bound phage were eluted with 0.1 M HCl for 10 min and the eluant was neutralized with 1.0 M Tris base. Eluted phage were amplified in *E. coli* XL1-blue and used for an additional round of selection.

EXAMPLE 2

Construction of Structural Database and Analysis of Amino Acid Distributions

We sequenced several hundred unique clones from each library following selection with protein A. The sequences were aligned, the occurrence of each amino acid type at each position was tabulated, the data were corrected for codon bias, and the distribution of the 20 natural amino acids at each position was calculated to produce the structure-based database of VHH domain diversity (Table 6) and FIG. 4.

Materials and Methods

DNA sequencing and analysis. Individual clones from each round of selection were grown overnight at 37° C., in a 96-well format, in 500 μl of 2YT broth supplemented with carbenicillin and M13-KO7 helper phage. Culture supernatants containing phage particles were used as templates for PCRs that amplified the DNA fragment encoding the VHH domain. The PCR primers were designed to add M13(-21) and M13R universal sequencing primers at either end of the amplified fragment, thus facilitating the use of these primers in sequencing reactions. Amplified DNA fragments were sequenced using Big-Dye terminator sequencing reactions, which were analyzed on an ABI Prism 3700 96-capillary DNA analyzer (PE Biosystems, Foster City, Calif.). All reactions were performed in a 96-well format.

The sequences were analyzed with the program SGCOUNT as described in Weiss et al., 2000, *Proc. Natl. Acad. Sci. USA*, 97: 8950-8954. Amino acid distributions for CDRH1 were determined from the CDRH1 sequences of 252 unique clones. Amino acid distributions for CDRH2 were determined from the CDRH2 sequences of 247 unique clones. Amino acid distributions for CDRH3 were determined from the CDRH3 sequences of 148 unique clones. Amino acid distributions for FRH3 were determined from the FRH3 sequences of 211 unique clones.

SGCOUNT aligned each DNA sequence against the wild-type DNA sequence by using a Needleman-Wunch pairwise alignment algorithm, translated each aligned sequence of acceptable quality, and tabulated the occurrence of each natural amino acid at each position. Additionally, SGCOUNT reported the presence of any sequences containing identical amino acids at all mutated positions. The tabulated data were normalized for codon bias in the NNK degenerate codon (N=A/G/C/T, K=G/T) used for randomization (e.g. the NNK codon contains three unique codons for Arg, and thus, the occurrence of Arg was divided by three). The normalized data were used to construct the structure-based database that recorded the percent occurrence of each amino acid at each position.

Analysis of Amino Acid Distributions. To determine the diversity in the structure-based database, we compared the Kyte-Doolittle hydrophobicity and Shannon entropy of each amino acid residue of in vitro selected CDRH1, CDRH2, CDRH3 and FRH3 to the Kyte-Doolittle hydrophobicity and Shannon entropy of each amino acid residue in the corresponding CDR or framework regions from human/mouse VH domain or natural camelid VHH domain (Harmsen et al., 1997, Mol. Immunol., 37: 579-590) (Tables 1 and 2).

Murine and human VH domain sequences from the Kabat database were aligned with camelid VHH domains using the ClustalW sequence alignment program (Thompson et al., 1994, *Nucleic Acids Res.*, 22: 4673-4680). The per residue variation for each library was estimated using Shannon Entropy as a measure of diversity (Stewart et al., 1997, *Mol. Immunol.*, 34:1067-1082) (Table 6). Shannon entropy is a metric that has been used to quantify diversity in immunoglobulins, T-cell receptors, and MHC class II promoters (Stewart et al., 1997, *Mol. Immunol.*, 34:1067-1082; Cowell et al., 1987, *J. Mol. Biol.*, 196:901-917. Shannon Entropy is defined for protein sites by the formula $$H = -\Sigma_{i=1-20} p_i \log_2 p_i$$

where $p_i$ is the fraction of residues at site that are of type i. Shannon entropy ranges from a minimum of zero (completely conserved sequence) to a maximum of 4.32 (equal occurrence of all 20 amino acids).

Amino acid distributions were also used to calculate the weighted hydrophobicity for each position. Using the Kyte-Doolittle scale for hydrophobicity (Kyte & Doolittle, 1982, *J. Mol. Biol.*, 157: 105-132) the fractional occurrence of each amino acid was multiplied by its hydrophobicity value, and all 20 weighted hydrophobicities were then summed for each position (Table 5).

Results

Hydrophobicity and Shannon Entropy analyses (Table 5, Table 6 and FIG. 4) revealed the diversity of CDRH1, CDRH2, and FRH3 in the structure-based database is significantly greater than that observed in natural antibodies (e.g., human/mouse VH domain or natural camelid VHH domain (Harmsen et al., 1997, Mol. Immunol., 37: 579-590)). Table 5 shows the diversity and hydrophobicity in VH domains in the human/mouse databases and in VHH domains in the structure-based and camelid databases. The standard deviations are shown in parentheses.

Table 6 and FIG. 4 show the structure-based database of VHH domain diversity. The fractional occurrence of each amino acid type at each position in CDRH1, CDRH2, and FRH3 was calculated after normalization for codon bias. At each position the number of occurrences of the amino acids was divided by the number of codons for that residue type in NNK. The normalized residue occurrence is divided by the normalized total to get the fractional occurrence. In FIG. 4, dark gray shaded residues are the residue types that together account for 50% of the sequence in the structure based database. The medium gray shaded residue are the residue types that account for 50% of the sequence in the human/mouse database. The light gray shaded residues are those residue types that are common in both the structure based database and human/mouse (naturally occurring sequence) database.

As described above, the data were used to determine Kyte-Doolittle hydrophobicity and Shannon entropy values of amino acid residues in the structure-based database which were compared to the Kyte-Doolittle hydrophobicities and Shannon entropies for human/mouse VH domains and Camelid VHH domains (Harmsen et al., 2000, Mol. Immunol., 37:579-590).

In each heavy chain CDR and in the FRH3, the average Shannon entropy for the in vitro structure-based database was greater than in the natural antibody databases, and the average weighted hydrophobicity was close to the average hydrophobicity of the 20 natural amino acids (−0.5), indicating the amino acid distribution was close to totally random.

Overall, the distributions of amino acids tolerated in each of the four loops tended to be less hydrophilic than in naturally evolved heavy chains. In the native distributions, CDRH2, CDRH3, and FRH3 had weighted hydrophobicities in the range of −0.5 to −2.2. For comparison, in the Kyte-Doolittle scale serine has a hydrophobicity value of −0.8 and histidine has a value of −3.2. In the in vitro selected database, the values ranged from slightly hydrophobic, 0.22 for CDRH2, to hydrophilic, −0.36 for CDRH3. CDRH1 tended to be more hydrophilic in the structure-based database: −0.73 for in vitro selected VHH domain vs. −0.25 for in vivo evolved VHH domains and −0.13 for classical human and murine VH domains.

A. CDRH1

Figure 3:
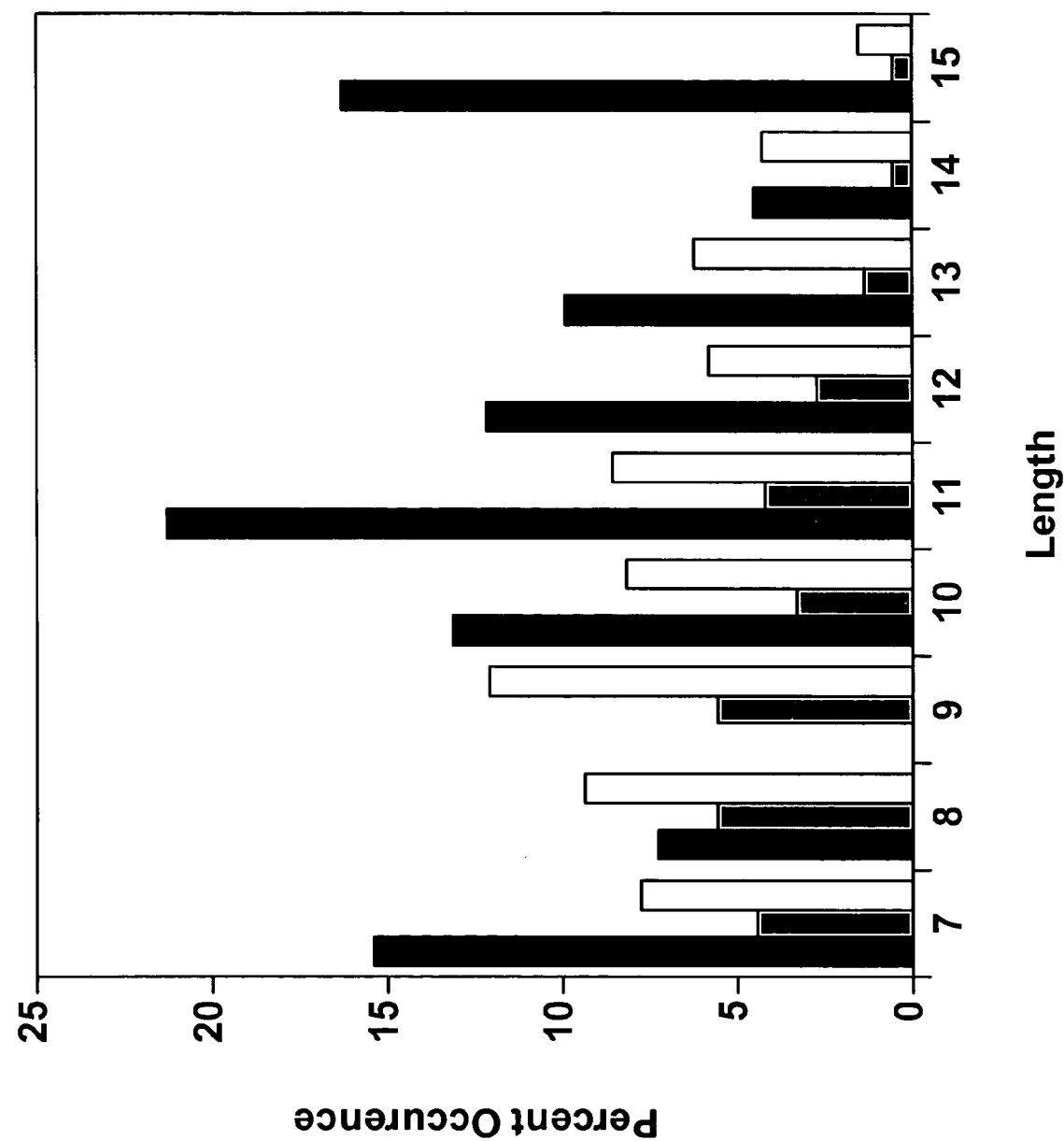
FIG. 3 shows calculated length distributions for CDRH3. The percent occurrence of each CDR3 length was calculated in the structure-based database (black bars), the human/mouse VH domain databases (light gray), and the camelid VHH domain database (white bars). The length distributions were calculated for sequences at positions 98 to 100h as this was the region replaced with different loop lengths. The distribution for the structure-based database was derived from the analysis of 211 unique clones from a library that contained CDRH3 loops of all lengths shown, with the exception of 9-residue lengths that were absent due to problems with library construction.

The pattern of hydrophobicity in CDRH1 was similar in both the natural and in vitro-derived databases according to the Chothia definition (positions 26 to 32) (Chothia & Lesk, 1987) with the exception of position 29, which was highly hydrophobic in natural antibodies but not in in vitro sequences (FIG. 3). In a number of VH domain structures, hydrophobic amino acids at position 29 face inward toward the core of the protein (Eigenbrot et al., 1993, J. Mol. Biol., 229: 969-95; Spinelli et al., 1996, Nat. Struct. Biol., 3: 752-7). Insertion of residue 29 into the core structurally constrains CDRH1 and limits the number of conformations the CDRH1 loop can adopt. Several studies have described a limited number of canonical conformations accessible to CDRH1, and each of these canonical conformations depends upon the nature and orientation of the residue at position 29 (Chothia et al., 1992, J. Mol. Biol., 227: 799-817). The in vitro selected CDRH1 loops showed no such dependence on hydrophobic residues at position 29. Six amino acids accounted for 50% of the amino acids observed, the only hydrophobic residue being Phe (Table 6, FIG. 4).

Positions on either side of the Chothia definition of CDRH1 were randomized. The in vitro database indicated the CDRH1 loop tolerated significantly greater diversity than CDRH1 loops found in nature. Shannon entropy indicated the entire stretch between positions 23 and 35 was highly diverse in the in vitro derived database (Table 6, FIG. 4). The hydrophobicity analysis showed a strong preference for hydrophobic residues at positions 24 and 34 (FIG. 3). This bias was also observed in the databases of natural human/mouse VH domains and camelid VHH domains. In VH and VHH domain structures, the side chains at positions 24 and 34 pointed directly into the core and were completely buried. Hydrophobic residues at positions 24 and 34 apparently acted as buried anchor points in both the natural and in vitro selected sequences. The natural domains, however, contained an additional buried anchor point at position 29 which was not observed amongst the domains selected purely for structural stability. In contrast, the structure-based database indicated residues 25-33 in in vitro selected VHH domains constituted a continuous hypervariable loop that runs along the top of the VH domain and is solvent accessible. This data indicated in vitro selected CDRH1s were highly accessible for making contacts with antigen.

B. CDR H2

Shannon entropies indicated high diversity in CDRH2 (Table 5). Position 51, however, was highly biased towards hydrophobic residues. This finding was reasonable in view of the Chothia definition of CDRH2 (Chothia & Lesk, 1987), which does not include this position. An Ile residue in natural VH domains almost invariably occupied position 51. Residue 51 plays a structural role as it is buried and points into the protein core (Eigenbrot et al., 1993). Residue 51 in the structure-based database was dominated by Phe, Ile and Leu. The bias for hydrophobic residues suggested residue 51 plays a conserved structural role both in natural and in vitro-selected VH domains. Positions 52 to 56 exhibited high Shannon entropies in both the natural and in vitro-derived databases. The overall diversity of the in vitro-selected CDRH2 sequences, however, was greater than that of the natural sequences. In particular, there was a greater abundance of hydrophobic residues in the structure-based database. As a result, the average hydrophobicity of the in vitro-selected CDRH2 sequences was significantly greater than that observed in natural antibodies (Table 5).

C. CDR H3

The structural stability of the VHH-RIG domain depends on certain residues at either end of the CDRH3 boundary (Bond et al., 2003, J. Mol. Biol., 332:643-655). A continuous stretch of amino acid sequence within the structural boundaries of CDRH3, extending from positions 98 to 100h, was randomized. Because of considerable bias near the boundaries of CDRH3 sequences in the Kabat database, we only analyzed positions 98 to 100h in the natural database to ensure only sequences with minimal biases imposed by structural constraints were included in our analysis. Within this region we investigated diversity in terms of both amino acid composition and length.

To investigate amino acid composition, we replaced the eleven amino acid loop of CDRH3 in the VHH-RIG domain with a random sequence of equal length. Shannon entropies of the loop sequence indicated high diversity and significant representation of all 20 amino acids throughout the loop (FIG. 4). There was slight bias for some amino acid types. Most notably, Phe was over-represented throughout the loop. As expected, the diversity of natural CDRH3 sequences was similar to that observed in the in vitro-derived database. Both the structure-based and natural databases indicated CDRH3 was capable of supporting unbiased diversity.

To investigate length diversity, we constructed libraries in which the eleven amino acid loop was replaced by random sequence loops ranging from 7 to 15 residues in length. All possible lengths were included with the exception of a 9-residue loop due to a problem in library construction. The libraries were pooled and subjected to two rounds of protein A selection. Following selection, the length distribution within the pool was determined from the sequences of 221 unique clones (FIG. 3). Although there was some variation in the frequencies of the different lengths, variation was not correlated with loop length. For example, the longest loop was amongst the most abundant. In contrast, both natural human/mouse and camelid antibodies exhibited a decrease in frequency as loop length increased. These results suggest the VHH domain fold can support extreme variations in CDRH3 length, provided the residues near the boundaries of the loop which contribute to structural stability are held constant.

D. FRH3/VFR

The structure-based database indicated FRH3 (amino acids 71-78) can accommodate diversities comparable to those observed in the CDRs. In the natural human/mouse antibody database, FRH3 exhibited Shannon entropies comparable to that of CDRH1 (Table 6, FIG. 4). Thus, FRH3 may play an auxiliary role for antigen binding in many natural antibodies. Our results suggested this role could be expanded in synthetic antibody repertoires. There appear to be no significant structural constraints on the diversity within the central portion of the FRH3 loop.

There are, however, apparent structural constraints at the boundaries of FRH3. Positions 71 and 78 show a high prevalence of Cys residues that frequently occurred in tandem; 30 out of 211 unique sequences had Cys at both positions while only 6 sequence had Cys at only one position. The simultaneous occurrence of Cys residues at both positions was strongly suggestive of an intramolecular disulfide bond that contributed to the overall stability of the VHH domain fold. Phenylalanine and other hydrophobic amino acids were also abundant at these positions, suggesting that stabilization can also be achieved through hydrophobic side chain packing interactions. A strong bias also existed at position 72 where Asp was highly prevalent. This position is highly conserved as an Asp in natural VH domains, and indeed, the wild type VHH-RIG domain also contains an Asp at this position. In the VHH-RIG domain structure (FIG. 1), Asp72 is the last residue in a β-strand, and the side chain carbonyl oxygen makes a hydrogen bond with the amide hydrogen of Lys75. Thus, it appeared diversity at the boundaries of FRH3 was restricted by structural constraints, but within the boundaries, the loop supported diversities comparable to those observed in the CDRs.

Our results demonstrated the immunoglobulin fold can tolerate significantly greater sequences diversity than is observed in natural antibodies. Thus, most of the sequence biases in natural databases likely arise from factors other than structural constraints. Bypassing these biases in vitro allows for the development of synthetic antibodies with structures and functions beyond the scope of the natural repertoire. On the other hand, it has been noted that some sequence biases may be indicative of selective pressure for certain residue types that are especially well suited for productive binding interactions with antigen.

TABLE 5

| Database | Residues | Average Shannon Entropy | Average Hydrophobicity |
|---|---|---|---|
| Human/Mouse | All | 1.75 (1.07) | −0.34 (2.14) |
| Camelid | | 1.49 (1.35) | −0.41 (2.24) |
| Human/Mouse | Framework[a] | 1.32 (0.81) | −0.16 (2.43) |
| Camelid | | 0.79 (0.78) | −0.28 (2.57) |
| Human/Mouse | 26-32 | 1.64 (0.50) | −0.13 (1.59) |
| Camelid | (CDR1) | 2.63 (0.82) | −0.25 (1.13) |

TABLE 5-continued

| Database | Residues | Average Shannon Entropy | Average Hydrophobicity |
|---|---|---|---|
| Structure-based | | 4.12 (0.07) | −0.73 (1.04) |
| Human/Mouse | 52-56 | 2.88 (0.46) | −1.37 (0.39) |
| Camelid | (CDR2) | 2.97 (0.58) | −1.05 (0.32) |
| Structure-based | | 3.99 (0.04) | −0.13 (0.30) |
| Human/Mouse | 71-78 | 1.84 (0.61) | −1.80 (1.01) |
| Camelid | (FRH3) | 1.27 (0.33) | −2.24 (2.01) |
| Structure-based | | 3.32 (0.60) | −0.36 (1.91) |
| Human/Mouse | 98-100 h | 3.23 (0.90) | −0.53 (0.96) |
| Camelid | (CDR3) | 3.76 (0.48) | −0.75 (0.48) |
| Structure-based | | 4.07 (0.06) | −0.12 (0.40) |

[a]The framework was defined as all residues not included in the above defined CDRH1, CDRH2, CDRH3, and FRH3 boundaries.

TABLE 6

| CDR | Residue | Human-Mouse Most Common AA | Fractional Occurrence | Shannon Entropy | Camelid Most Common AA | Fractional Occurance | Shannon Entropy | RIG Most Common AA | Fractional Occurance | Shannon Entropy |
|---|---|---|---|---|---|---|---|---|---|---|
| H1 | 26 | G | 0.97 | 0.28 | G | 0.87 | 0.94 | D, G, N, S, T, V | 0.09, 0.11, 0.08, 0.08, 0.07 | 4.11 |
| | 27 | F, Y | 0.50, 0.35 | 1.90 | F, R, S | 0.27, 0.18, 0.18 | 3.23 | A, D, H, N, S, W | 0.10, 0.11, 0.08, 0.07, 0.07, 0.06 | 4.15 |
| | 28 | S, T | 0.31, 0.60 | 1.76 | T, I | 0.49, 0.17 | 2.60 | D, L, N, P, S, T, V | 0.07, 0.06, 0.10, 0.07, 0.07, 0.06, 0.06 | 4.21 |
| | 29 | F | 0.70 | 1.45 | F | 0.53 | 2.58 | D, F, G, N, P, Y | 0.12, 0.09, 0.09, 0.06, 0.082, 0.09 | 4.09 |
| | 30 | S, T | 0.51, 0.40 | 1.76 | S, D | 0.48, 0.11 | 2.74 | A, D, F, H, I, P, Q, S, W | 0.05, 0.06, 0.09, 0.08, 0.05, 0.05, 0.07, 0.08, 0.05 | 4.21 |
| | 31 | S | 0.52 | 2.32 | D, I, S | 0.14, 0.18, 0.18 | 3.52 | D, F, H, N, P, V | 0.12, 0.07, 0.06, 0.13, 0.09, 0.06 | 4.04 |
| | 32 | Y | 0.67 | 1.98 | Y, S | 0.45, 0.05 | 2.77 | D, E, F, H, L, S, T | 0.15, 0.05, 0.06, 0.06, 0.06, 0.06, 0.07 | 4.06 |
| | 33 | A, W, Y | 0.15, 0.21, 0.22 | 3.11 | A, C, Y | 0.34, 0.09, 0.08 | 3.38 | A, D, I, N, T, V, Y | 0.06, 0.09, 0.07, 0.09, 0.08, 0.07, 0.12 | 3.97 |
| H2 | 52 | N, S, Y | 0.22, 0.19, 0.19 | 3.23 | N, S, T | 0.21, 0.24, 0.19 | 3.21 | F, L, S, T, V, Y | 0.09, 0.1, 0.17, 0.08, 0.08, 0.08 | 3.93 |
| | 52a | P | 0.47 | 2.81 | S, T, W | 0.25, 0.13, 0.16 | 3.38 | A, D, F, G, H, N, S, V, W | 0.05, 0.05, 0.16, 0.10, 0.05, 0.05, 0.12, 0.05, 0.05, 0.06 | 3.99 |
| | 53 | D, G, N, S | 0.12, 0.18, 0.16, 0.21 | 3.28 | D, G, S | 0.16, 0.26, 0.24 | 3.09 | D, F, G, S, V, Y | 0.08, 0.14, 0.06, 0.12, 0.06, 0.08 | 4.01 |
| | 54 | G, S | 0.30, 0.27 | 2.70 | D, G | 0.11, 0.68 | 1.81 | D, F, G, P, S | 0.09, 0.08, 0.08, 0.11, 0.16 | 4.00 |
| | 55 | G | 0.61 | 2.08 | D, G, S, T | 0.11, 0.29, 0.17, 0.11 | 3.22 | D, F, G, N, S | 0.09, 0.09, 0.13, 0.07, 0.13 | 3.95 |
| | 56 | G, S, N | 0.12, 0.11, 0.27 | 3.20 | S, T | 0.22, 0.35 | 3.10 | F, H, M, Q, S, T | 0.14, 0.08, 0.06, 0.07, 0.11, 0.06 | 4.03 |
| FRH3 | 71 | R, V | 0.45, 0.25 | 2.32 | R | 0.72 | 1.69 | C, F, Y | 0.19, 0.28, 0.14 | 3.21 |
| | 72 | D | 0.89 | 0.75 | D | 0.91 | 0.71 | D | 0.62 | 2.14 |

TABLE 6-continued

| | | Human-Mouse | | | Camelid | | | RIG | | |
|---|---|---|---|---|---|---|---|---|---|---|
| CDR | Residue | Most Common AA | Fractional urrence | Shannon Entropy | Most Common AA | Fractional Occurance | Shannon Entropy | Most Common AA | Fractional Occurance | Shannon Entropy |
| | 73 | K, N | 0.24, 0.30 | 2.28 | N | 0.76 | 1.58 | A, D, P, R, S | 0.07, 0.07, 0.24, 0.08, 0.10 | 3.76 |
| | 74 | S | 0.71 | 1.59 | A | 0.81 | 1.27 | A, D, S | 0.07, 0.29, 0.12 | 3.63 |
| | 75 | K, S | 0.42, 0.27 | 2.54 | K | 0.82 | 1.19 | D, G, R, S, T | 0.09, 0.11, 0.09, 0.16, 0.08 | 3.88 |
| | 76 | N, S | 0.49, 0.43 | 1.55 | N | 0.78 | 1.40 | G, K, R, S | 0.16, 0.10, 0.12, 0.13 | 3.62 |
| | 77 | T | 0.60 | 1.85 | T | 0.83 | 1.05 | I, T, V | 0.13, 0.13, 0.25 | 3.60 |
| | 78 | A, L | 0.40, 0.30 | 2.18 | V | 0.70 | 1.51 | C, F, L | 0.21, 0.22, 0.17 | 2.88 |

EXAMPLE 3

Design of a Heavy Chain VEGF Antibody

The VHH-RIG scaffold is useful as a starting template in the design of a naïve antibody library. A library of VHH domains is generated using a RIG scaffold. VFR and one or more of CDRH1, CDRH2, and CDRH3 is randomized as described in Example 1. The resulting library is sorted against human VEGF. Clones are selected by in vitro panning for binding to VEGF using the method described in Example 1. After three rounds of sorting, the clones are sequenced and analyzed for bias for a particular amino acid at any position in the randomized loop(s) as described in Example 2. If the distribution analysis reveals a strong preference for cysteine at two positions that implies the formation of a disulfide constrained loop, a subsequent library is made where the identified cysteine residues are fixed and the amino acid sequence between the fixed cysteine residues is randomized as described above. Clones from the subsequent library are selected by panning for binding to VEGF as described above.

Individual clones of the library are screened for binding to VEGF by competition ELISA. Soluble VEGF concentrations in the screening ELISA are 2 µM and 20 µM. Clones that demonstrate appreciable binding activity that is attenuated in a dose dependent manner by the two concentrations of soluble VEGF are selected for further characterization. The IC50 of the selected clones for the VEGF is determined by a multipoint competition ELISA in which the concentration of soluble VEGF ranges from 0.1-100 µM.

EXAMPLE 4

Generation of an ErbB2 Antibody Library

Pertuzumab, also known as 2C4 or Omnitarg™, is an anti-ErbB2 monoclonal antibody (Genentech, Inc.). A library is generated using pertuzumab as a scaffold. VFR, alone or in combination with one or more of CDRH1, CDRH2, and CDRH3, is randomized as described in Example 1. Clones are selected by in vitro panning for binding to ErbB2 using the method described in Example 1. After three rounds of sorting, the clones are sequenced and analyzed for bias for a particular amino acid at any position in the randomized loop(s) as described in Example 2. If the distribution analysis reveals a strong preference for cysteine at two positions that implies the formation of a disulfide constrained loop, a subsequent library is made where the identified cysteine residues are fixed and the amino acid sequence between the fixed cysteine residues is randomized as described above. Clones from the subsequent library are selected by panning for binding to ErbB2 as described above.

Individual clones of the library are screened for binding to ErbB2 by competition ELISA with pertuzumab. ErbB2 concentrations in the screening ELISA are 2 µM and 20 µM. Clones that demonstrate appreciable binding activity that is attenuated in a dose dependent manner by the two concentrations of soluble ErbB2 are selected for further characterization. The IC50 of the selected clones for ErbB2 is determined by a multipoint competition ELISA in which the concentration of ErbB2 ranges from 0.1-100 µM. The IC50 of the selected clones is than compared to the IC50 of pertuzumab.

We claim:

1. A polypeptide library comprising a plurality of monobody variable heavy chain domains, wherein each monobody variable heavy chain domain comprises a variant variable framework region (VFR), wherein the amino acid positions of the VFR form a loop in an antigen binding pocket, wherein the amino acid positions are according to the Kabat numbering system, wherein the VFR comprises:
   a) a N-terminal portion that comprises at least one structural amino acid position comprising one or both of the first two amino acid positions of the N-terminal portion of the VFR, wherein said structural amino acid position has a variant amino acid selected from the group consisting of up to six different amino acids, wherein the first amino acid position of the N-terminal portion corresponds to position 71 of a variable heavy chain domain and is C, F, Y, W, M, or L;
   b) a central portion that comprises at least one nonstructural amino acid position, wherein the nonstructural amino acid position has a variant amino acid comprising any of the naturally occurring amino acids; and
   c) a C-terminal portion that comprises at least one structural amino acid position, wherein said structural amino acid position has a variant amino acid selected from the group consisting of up to six different amino acids.

2. The polypeptide library of claim 1, wherein said at least one structural amino acid position of the C-terminal portion of the VFR is the last amino acid position of the C-terminal portion.

3. The polypeptide library of 1, wherein said at least one structural amino acid position of the N-terminal portion corresponds to position 71 of a variable heavy chain domain and the variant amino acid is C, F, or Y, and wherein the amino acid position is according to the Kabat numbering system.

4. The polypeptide library of claim 1, wherein said at least one structural amino acid position of the N-terminal portion comprises both of the first two amino acid positions of the N-terminal portion, and wherein the first amino acid position corresponds to position 71 of a variable heavy chain domain and is C, F, or Y, and the second amino acid position corresponds to position 72 of a variable heavy chain domain and is D or E, and wherein the amino acid positions are according to the Kabat numbering system.

5. The polypeptide library of claim 2 or claim 4, wherein said at least one structural amino acid position of the C-terminal portion corresponds to position 78 of a variable heavy chain domain and is C or F, and wherein the amino acid position is according to the Kabat numbering system.

6. The polypeptide library of claim 1, wherein the central portion is no more than 20 amino acids.

7. The polypeptide library of claim 6, wherein said at least one nonstructural position has a variant amino acid encoded by a non-random codon set.

8. The polypeptide library of claim 1, wherein said at least one structural amino acid position of the C-terminal portion corresponds to position 78 of a variable heavy chain domain and the variant amino acid is M, C, F, V, or I.

9. The polypeptide library of claim 8, wherein position 71 is a cysteine and position 78 is a cysteine.

10. The polypeptide library of claim 1 wherein each monobody variable heavy chain domain is a fusion polypeptide.

11. The polypeptide library of claim 10 wherein each fusion polypeptide is fused to at least a portion of a viral coat protein.

12. The polypeptide library of claim 11, wherein the viral coat protein is selected from the group consisting of pIII, pvIII, Soc, Hoc, 9pD, pV1 and variants thereof.

13. The polypeptide library of claim 1, wherein each monobody variable heavy chain domain further comprises a variant complementarity determining region 1 (CDR1) comprising:
   a) a N-terminal portion that comprises at least one structural amino acid position, wherein said structural amino acid position has a variant amino acid selected from the group consisting of up to six different amino acids;
   b) a central portion that comprises at least one nonstructural amino acid position, wherein the nonstructural amino acid position has a variant amino acid comprising any of the naturally occurring amino acids; and
   c) a C-terminal portion that comprises at least one structural amino acid position, wherein said structural amino acid position has a variant amino acid selected from the group consisting up to six different amino acids, and wherein the amino acid positions in the CDR1 region form a loop of the antigen binding pocket.

14. The polypeptide library of claim 13, wherein the structural amino acid position of the N-terminal portion of CDR1 corresponds to amino acid position 24 of a monobody variable heavy chain domain; the structural amino acid position of the C-terminal portion of CDR1 corresponds to amino acid position 34 of a monobody variable heavy chain domain; and the central portion amino acid positions of CDR1 correspond to amino acids positions 25 to 33 of a monobody variable heavy chain domain; and wherein the amino acid positions are according to the Kabat numbering system.

15. The polypeptide library of claim 14, wherein the structural amino acid position at position 24 is F, Y, V, or I and at position 34 is F, V, or I.

16. The polypeptide library of claim 1, wherein each monobody variable heavy chain domain further comprises a variant complementarity determining region 2 (CDR2) comprising:
   a) a N-terminal portion that comprises at least one structural amino acid position, wherein said structural amino acid position has a variant amino acid selected from the group consisting of up to six different amino acids; and
   b) a central portion that comprises at least one nonstructural amino acid position, wherein the nonstructural amino acid position has a variant amino acid comprises any of the naturally occurring amino acids; and wherein the amino acid positions of the CDR2 form a loop of the antigen binding pocket.

17. The polypeptide library of claim 16, wherein the structural amino acid position of the N-terminal portion of CDR2 corresponds to amino acid position 51 of a variable heavy chain domain and the central portion amino acid positions of CDR2 correspond to amino acid positions 52 to 56 of a variable heavy chain domain and can be any of the naturally occurring amino acids; and wherein the amino acid positions are according to the Kabat numbering system.

18. The polypeptide library of claim 17, wherein the structural amino acid position at position 51 is F or L.

19. The polypeptide library of claim 1, wherein each monobody variable heavy chain domain further comprises a variant complementarity determining region 3 (CDR3) comprising:
   a) a N-terminal portion that comprises at least one structural amino acid position, wherein said structural amino acid position has a variant amino acid that is selected from the group consisting of up to six different amino acids;
   b) a central portion that comprises at least one nonstructural amino acid position, wherein the nonstructural amino acid position has a variant amino acid that comprises any of the naturally occurring amino acids; and
   c) a C-terminal portion that comprises at least one structural amino acid position, wherein said structural amino acid position has a variant amino acid that is selected from the group consisting of up to six different amino acids, and wherein the amino acid positions in the CDR3 region form a loop of the antigen binding pocket.

20. The polypeptide library of claim 19, wherein the structural amino acid positions of the N-terminal portion of CDR3 correspond to amino acid positions 96 and 97 of a variable heavy chain domain; the structural amino acid positions of the C-terminal portion of CDR3 correspond to amino acid positions 100i, 100j, 100k and 100l of a variable heavy chain domain; and the central portion amino acid positions of CDR3 correspond to amino acid positions 98 to 100h of a variable heavy chain domain; and wherein the amino acid positions are according to the Kabat numbering system.

21. The polypeptide library of claim 20, wherein amino acid position 96 is R, amino acid position 97 is I, amino acid position 100i is W, amino acid position 100j is V, amino acid position 100k is T, and amino acid position 100l is W.

22. A method of generating a plurality of monobody variable heavy chain domains, each monobody variable heavy chain domain comprising a variable framework region (VFR), wherein the amino acid positions of the VFR form a loop in an antigen binding pocket and, wherein the amino acid positions are according to the Kabat numbering system, said method comprising:
   a) replacing an amino acid in at least one structural amino acid position comprising one or both of the first two amino acid positions of the N-terminal portion of the VFR, with up to six different amino acids, wherein the first amino acid position of the N-terminal portion corresponds to position 71 of a variable heavy chain domain and is C, F, Y, W, M, or L;
   b) replacing an amino acid in at least one nonstructural amino acid position with any naturally occurring amino acid, wherein the nonstructural amino acids comprise about 1 to 20 contiguous amino acids; and
   c) replacing an amino acid in at least one structural amino acid position at the C terminus of the VFR with up to six different amino acids.

23. The method according to claim 22, wherein the monobody variable domain is a variable heavy chain domain is a variable domain of a camelid monobody.

* * * * *